(12) United States Patent
Christianson et al.

(10) Patent No.: US 11,185,409 B2
(45) Date of Patent: Nov. 30, 2021

(54) COLLAPSIBLE INNER FLOW CONTROL COMPONENT FOR SIDE-DELIVERED TRANSCATHETER HEART VALVE PROSTHESIS

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US); Chad Perrin, Andover, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 16/455,740

(22) Filed: Jun. 27, 2019

(65) Prior Publication Data

US 2020/0237506 A1     Jul. 30, 2020

Related U.S. Application Data

(60) Provisional application No. 62/797,201, filed on Jan. 26, 2019.

(51) Int. Cl.
*A61F 2/24* (2006.01)
*B33Y 80/00* (2015.01)

(52) U.S. Cl.
CPC .......... *A61F 2/2418* (2013.01); *A61F 2/2439* (2013.01); *B33Y 80/00* (2014.12);
(Continued)

(58) Field of Classification Search
CPC ......... A61F 2/24; A61F 2/2418; A61F 2/2439
See application file for complete search history.

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |

(Continued)

FOREIGN PATENT DOCUMENTS

| | | |
|---|---|---|
| AU | 2006203686 B2 | 11/2008 |
| AU | 2006203686 B2 | 11/2008 |

(Continued)

OTHER PUBLICATIONS

Office Action for U.S. Appl. No. 17/154,227, dated Jun. 18, 2021, 8 pages.

(Continued)

*Primary Examiner* — Matthew W Schall

(57) ABSTRACT

The invention relates to a transcatheter heart valve replacement (A61F2/2412), and in particular a side delivered transcatheter prosthetic heart valve having a collapsible inner flow control component, and an outer annular support frame having compressible wire cells that facilitate folding flat along the z-axis and compressing the valve vertically along the y-axis, or orthogonally to the central axis of the flow control component, allowing a very large diameter valve to be delivered and deployed to the tricuspid valve from the inferior vena cava or superior vena cava, or trans-atrially to the mitral valve, the valve having a height of about 5-60 mm and a diameter of about 25-80 mm, without requiring an oversized diameter catheter and without requiring delivery and deployment from a catheter at an acute angle of approach.

15 Claims, 30 Drawing Sheets

(52) U.S. Cl.
CPC ............... *A61F 2210/0014* (2013.01); *A61F 2220/0008* (2013.01); *A61F 2230/0008* (2013.01); *A61F 2230/0017* (2013.01); *A61F 2230/0069* (2013.01); *A61F 2240/001* (2013.01)

(56) References Cited

U.S. PATENT DOCUMENTS

| | | | |
|---|---|---|---|
| 6,006,134 A | 12/1999 | Hill et al. | |
| 6,197,013 B1 | 3/2001 | Reed et al. | |
| 6,290,719 B1 | 9/2001 | Garberoglio | |
| 6,449,507 B1 | 9/2002 | Hill et al. | |
| 6,532,388 B1 | 3/2003 | Hill et al. | |
| 6,582,467 B1 | 6/2003 | Teitelbaum | |
| 6,628,987 B1 | 9/2003 | Hill et al. | |
| 6,718,208 B2 | 4/2004 | Hill et al. | |
| 6,769,434 B2 | 8/2004 | Liddicoat et al. | |
| 6,890,330 B2 | 5/2005 | Streeter et al. | |
| 6,896,690 B1 | 5/2005 | Lambrecht et al. | |
| 6,904,318 B2 | 6/2005 | Hill et al. | |
| 6,929,653 B2 | 8/2005 | Strecter | |
| 7,074,189 B1 | 7/2006 | Montegrande | |
| 7,125,418 B2 | 10/2006 | Duran | |
| 7,175,660 B2 | 2/2007 | Cartledge et al. | |
| 7,201,761 B2 | 4/2007 | Woolfson et al. | |
| 7,225,019 B2 | 5/2007 | Jahns et al. | |
| 7,269,457 B2 | 9/2007 | Shafer et al. | |
| 7,331,991 B2 | 2/2008 | Kheradvar et al. | |
| 7,374,571 B2 | 5/2008 | Pease et al. | |
| 7,449,027 B2 | 11/2008 | Hunt et al. | |
| 7,621,948 B2 | 11/2009 | Herrmann et al. | |
| 7,717,952 B2 | 5/2010 | Case et al. | |
| 7,749,245 B2 | 7/2010 | Cohn et al. | |
| 7,753,949 B2 | 7/2010 | Lamphere et al. | |
| 7,828,840 B2 | 11/2010 | Biggs et al. | |
| 7,846,199 B2 | 12/2010 | Paul, Jr. et al. | |
| 8,303,648 B2 | 11/2012 | Grewe et al. | |
| 8,366,768 B2 | 2/2013 | Zhang | |
| 8,491,650 B2 | 7/2013 | Wiemeyer et al. | |
| 8,568,474 B2 | 10/2013 | Yeung | |
| 8,641,752 B1 | 2/2014 | Holm et al. | |
| 8,696,743 B2 | 4/2014 | Holecek et al. | |
| 8,728,153 B2 | 5/2014 | Bishop et al. | |
| 8,758,395 B2 | 6/2014 | Kleshinski et al. | |
| 8,846,390 B2 | 9/2014 | Dove et al. | |
| 8,876,892 B2 | 11/2014 | Tran et al. | |
| 8,900,295 B2 | 12/2014 | Migliazza et al. | |
| 8,915,958 B2 | 12/2014 | Braido | |
| 8,926,690 B2 | 1/2015 | Kovalsky | |
| 8,926,692 B2 | 1/2015 | Dwork | |
| 8,926,694 B2 | 1/2015 | Costello | |
| 8,940,044 B2 | 1/2015 | Hammer et al. | |
| 8,956,404 B2 | 2/2015 | Bortlein et al. | |
| 8,986,370 B2 | 3/2015 | Annest et al. | |
| 9,011,524 B2 | 4/2015 | Eberhardt | |
| 9,017,399 B2 | 4/2015 | Gross et al. | |
| 9,050,188 B2 | 6/2015 | Schweich, Jr. et al. | |
| 9,072,604 B1 | 7/2015 | Melnick et al. | |
| 9,119,714 B2 | 9/2015 | Shandas et al. | |
| 9,216,076 B2 | 12/2015 | Mitra et al. | |
| 9,232,995 B2 | 1/2016 | Kovalsky et al. | |
| 9,241,792 B2 | 1/2016 | Benichou | |
| 9,248,016 B2 | 2/2016 | Oba | |
| 9,259,215 B2 | 2/2016 | Chou et al. | |
| 9,277,990 B2 | 3/2016 | Klima et al. | |
| 9,289,282 B2 | 3/2016 | Olson | |
| 9,289,296 B2 | 3/2016 | Braido | |
| 9,295,547 B2 | 3/2016 | Costello | |
| 9,301,839 B2 | 4/2016 | Stante et al. | |
| 9,308,086 B2 | 4/2016 | Ho | |
| 9,339,367 B2 | 5/2016 | Carpenter et al. | |
| 9,370,418 B2 | 6/2016 | Pintor et al. | |
| 9,381,083 B2 | 7/2016 | Costello | |
| 9,387,075 B2 | 7/2016 | Bortlein et al. | |
| 9,393,111 B2 | 7/2016 | Ma et al. | |
| 9,414,915 B2 | 8/2016 | Lombardi et al. | |
| 9,433,500 B2 | 9/2016 | Chau | |
| 9,440,054 B2 | 9/2016 | Bishop et al. | |
| 9,456,899 B2 | 10/2016 | Yeung et al. | |
| 9,468,525 B2 | 10/2016 | Kovalsky et al. | |
| 9,474,604 B2 | 10/2016 | Centola | |
| 9,486,306 B2 | 11/2016 | Tegels et al. | |
| 9,510,941 B2 | 12/2016 | Bishop et al. | |
| 9,554,902 B2 | 1/2017 | Braido et al. | |
| 9,579,196 B2 | 2/2017 | Morriss et al. | |
| 9,579,200 B2 | 2/2017 | Lederman et al. | |
| 9,610,159 B2 | 4/2017 | Christianson et al. | |
| 9,615,925 B2 | 4/2017 | Subramanian et al. | |
| 9,629,719 B2 | 4/2017 | Rothstein | |
| 9,636,222 B2 | 5/2017 | Oslund | |
| 9,649,191 B2 | 5/2017 | Savage et al. | |
| 9,662,202 B2 | 5/2017 | Quill et al. | |
| 9,662,203 B2 | 5/2017 | Sheahan | |
| 9,662,209 B2 | 5/2017 | Gross et al. | |
| 9,675,454 B2 | 6/2017 | Vidlund et al. | |
| 9,675,485 B2 | 6/2017 | Essinger et al. | |
| 9,687,343 B2 | 6/2017 | Börtlein | |
| 9,707,076 B2 | 7/2017 | Stack et al. | |
| 9,713,530 B2 | 7/2017 | Cabiri et al. | |
| 9,750,607 B2 | 9/2017 | Ganesan et al. | |
| 9,763,778 B2 | 9/2017 | Eidenschink et al. | |
| 9,763,779 B2 | 9/2017 | Börtlein | |
| 9,788,946 B2 | 10/2017 | Bobo, Jr. et al. | |
| 9,839,511 B2 | 12/2017 | Ma et al. | |
| 9,849,011 B2 | 12/2017 | Zimmerman et al. | |
| 9,855,384 B2 | 1/2018 | Cohen et al. | |
| 9,861,464 B2 | 1/2018 | Azimpour et al. | |
| 9,895,219 B2 | 2/2018 | Costello | |
| 9,901,330 B2 | 2/2018 | Akpinar | |
| 9,918,838 B2 | 3/2018 | Ring | |
| 9,943,409 B2 | 4/2018 | Kim et al. | |
| 9,949,825 B2 | 4/2018 | Braido et al. | |
| 9,968,444 B2 | 5/2018 | Millwee et al. | |
| 9,968,445 B2 | 5/2018 | Kheradvar | |
| 9,980,815 B2 | 5/2018 | Nitzan et al. | |
| 9,987,121 B2 | 6/2018 | Blanzy | |
| 10,010,411 B2 | 7/2018 | Peter | |
| 10,010,412 B2 | 7/2018 | Taft et al. | |
| 10,022,054 B2 | 7/2018 | Najafi et al. | |
| 10,022,222 B2 | 7/2018 | Groothuis et al. | |
| 10,022,223 B2 | 7/2018 | Bruchman | |
| 10,028,821 B2 | 7/2018 | Centola | |
| 10,028,831 B2 | 7/2018 | Morin et al. | |
| 10,034,667 B2 | 7/2018 | Morris et al. | |
| 10,034,747 B2 | 7/2018 | Harewood | |
| 10,039,638 B2 | 8/2018 | Bruchman et al. | |
| 10,058,315 B2 | 8/2018 | Rafiee et al. | |
| 10,058,411 B2 | 8/2018 | Fifer et al. | |
| 10,058,421 B2 | 8/2018 | Eberhardt et al. | |
| 10,058,426 B2 | 8/2018 | Barbarino | |
| 10,064,405 B2 | 9/2018 | Dale et al. | |
| 10,080,653 B2 | 9/2018 | Conklin et al. | |
| 10,085,835 B2 | 10/2018 | Thambar et al. | |
| 10,105,224 B2 | 10/2018 | Buchbinder et al. | |
| 10,117,741 B2 | 11/2018 | Schweich, Jr. et al. | |
| 10,123,874 B2 | 11/2018 | Khairkhahan et al. | |
| 10,130,331 B2 | 11/2018 | Stigall et al. | |
| 10,130,467 B2 | 11/2018 | Braido et al. | |
| 10,149,685 B2 | 12/2018 | Kizuka | |
| 10,154,905 B2 | 12/2018 | Duffy | |
| 10,179,043 B2 | 1/2019 | Cohen-Tzemach et al. | |
| 10,182,908 B2 | 1/2019 | Tubishevitz et al. | |
| 10,182,911 B2 | 1/2019 | Hillukka | |
| 10,206,775 B2 | 2/2019 | Kovalsky | |
| 10,219,895 B2 | 3/2019 | Wagner et al. | |
| 10,219,896 B2 | 3/2019 | Sandstrom | |
| 10,220,192 B2 | 3/2019 | Drasler et al. | |
| 10,226,178 B2 | 3/2019 | Cohen et al. | |
| 10,226,335 B2 | 3/2019 | Cartledge | |
| 10,245,142 B2 | 4/2019 | Bonhoeffer | |
| 10,258,467 B2 | 4/2019 | Hou et al. | |
| 10,265,173 B2 | 4/2019 | Griffin et al. | |
| 10,321,987 B2 | 6/2019 | Wang et al. | |
| 10,321,995 B1 * | 6/2019 | Christianson | ......... A61F 2/2418 |

(56) References Cited

U.S. PATENT DOCUMENTS

| | | |
|---|---|---|
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy |
| 10,398,550 B2 | 9/2019 | Chalekian et al. |
| 10,426,611 B2 | 10/2019 | Hariton et al. |
| 10,433,957 B2 | 10/2019 | Khouengboua |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 2003/0040772 A1 | 2/2003 | Hyodoh et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0088047 A1 | 5/2004 | Spence et al. |
| 2004/0116996 A1 | 6/2004 | Freitag |
| 2004/0199209 A1 | 10/2004 | Hill et al. |
| 2005/0010246 A1 | 1/2005 | Streeter et al. |
| 2005/0107811 A1 | 5/2005 | Starksen et al. |
| 2005/0137686 A1 | 6/2005 | Salahieh et al. |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0094189 A1 | 4/2009 | Stephens |
| 2009/0192586 A1 | 7/2009 | Tabor |
| 2009/0254174 A1 | 10/2009 | Case et al. |
| 2009/0264991 A1 | 10/2009 | Paul, Jr. et al. |
| 2009/0287290 A1 | 11/2009 | Macaulay |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0305685 A1 | 12/2010 | Millwee et al. |
| 2011/0029071 A1 | 2/2011 | Zlotnick et al. |
| 2011/0071613 A1 | 3/2011 | Wood et al. |
| 2011/0098804 A1 | 4/2011 | Yeung |
| 2011/0125145 A1 | 5/2011 | Mody |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross |
| 2012/0022644 A1 | 1/2012 | Reich et al. |
| 2012/0035701 A1 | 2/2012 | To |
| 2012/0065723 A1 | 3/2012 | Drasler et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim |
| 2012/0277853 A1 | 11/2012 | Rothstein |
| 2012/0310327 A1 | 12/2012 | McHugo |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0331929 A1 | 12/2013 | Mitra et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0081383 A1 | 3/2014 | Eberhardt et al. |
| 2014/0088680 A1 | 3/2014 | Costello |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |

(56) References Cited

U.S. PATENT DOCUMENTS

| | | |
|---|---|---|
| 2014/0324161 A1 | 10/2014 | Tegels et al. |
| 2014/0350662 A1 | 11/2014 | Vaturi |
| 2014/0371789 A1 | 12/2014 | Hariton et al. |
| 2014/0379076 A1 | 12/2014 | Vidlund |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust |
| 2017/0112620 A1 | 4/2017 | Curley et al. |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0196690 A1 | 7/2017 | Racchini et al. |
| 2017/0209266 A1 | 7/2017 | Lane |
| 2017/0209268 A1 | 7/2017 | Cunningham et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson |
| 2017/0348100 A1 | 12/2017 | Lane |
| 2017/0360558 A1 | 12/2017 | Ma |
| 2017/0360561 A1 | 12/2017 | Bell et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |

(56) References Cited

U.S. PATENT DOCUMENTS

| | | |
|---|---|---|
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296335 A1 | 10/2018 | Miyashiro |
| 2018/0296337 A1 | 10/2018 | Duhay et al. |
| 2018/0303488 A1 | 10/2018 | Hill |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |

FOREIGN PATENT DOCUMENTS

| | | |
|---|---|---|
| AU | 2009219415 A1 | 9/2009 |
| AU | 2009219415 A1 | 9/2009 |
| AU | 2011238752 A1 | 10/2012 |
| AU | 2011238752 A1 | 10/2012 |
| AU | 2011240940 A1 | 10/2012 |
| AU | 2011240940 A1 | 10/2012 |
| AU | 2012272855 A1 | 1/2014 |
| AU | 2012272855 A1 | 1/2014 |
| AU | 2011236036 B2 | 6/2014 |
| AU | 2011236036 B2 | 6/2014 |
| AU | 2011248657 B2 | 12/2014 |
| AU | 2011248657 B2 | 12/2014 |
| AU | 2016228261 A1 | 4/2017 |
| AU | 2016228261 A1 | 4/2017 |
| AU | 2017210659 A1 | 8/2017 |
| AU | 2017210659 A1 | 8/2017 |
| AU | 2013245201 B2 | 10/2017 |
| AU | 2013245201 B2 | 10/2017 |
| AU | 2014360294 B2 | 10/2017 |
| AU | 2014360294 B2 | 10/2017 |
| AU | 2016249819 A1 | 11/2017 |
| AU | 2016249819 A1 | 11/2017 |
| AU | 2016371525 A1 | 5/2018 |
| AU | 2016371525 A1 | 5/2018 |
| AU | 2016366783 A1 | 6/2018 |

(56) References Cited

FOREIGN PATENT DOCUMENTS

| | | | |
|---|---|---|---|
| AU | 2016366783 A1 | 6/2018 |
| AU | 2017214672 B2 | 10/2018 |
| AU | 2017214672 B2 | 10/2018 |
| AU | 2017285993 A1 | 1/2019 |
| AU | 2017285993 A1 | 1/2019 |
| AU | 2014201920 B2 | 2/2019 |
| AU | 2014201920 B2 | 2/2019 |
| AU | 2015411406 B2 | 2/2019 |
| AU | 2015411406 B2 | 2/2019 |
| AU | 2019202290 A1 | 4/2019 |
| AU | 2019202290 A1 | 4/2019 |
| AU | 2017388857 A1 | 8/2019 |
| AU | 2017388857 A1 | 8/2019 |
| BR | PI0909379 B1 | 9/2019 |
| BR | PI0909379 B1 | 9/2019 |
| CA | 2531528 A1 | 1/2005 |
| CA | 2531528 A1 | 1/2005 |
| CA | 2609800 A1 | 1/2007 |
| CA | 2609800 A1 | 1/2007 |
| CA | 2822636 A1 | 10/2008 |
| CA | 2822636 A1 | 10/2008 |
| CA | 2398948 C | 8/2009 |
| CA | 2398948 C | 8/2009 |
| CA | 2813419 A1 | 4/2012 |
| CA | 2813419 A1 | 4/2012 |
| CA | 2856088 A1 | 5/2013 |
| CA | 2856088 A1 | 5/2013 |
| CA | 2866315 A1 | 9/2013 |
| CA | 2866315 A1 | 9/2013 |
| CA | 2922123 A1 | 4/2015 |
| CA | 2922123 A1 | 4/2015 |
| CA | 2504258 C | 6/2015 |
| CA | 2504258 C | 6/2015 |
| CA | 2677648 C | 10/2015 |
| CA | 2677648 C | 10/2015 |
| CA | 2815331 C | 10/2015 |
| CA | 2815331 C | 10/2015 |
| CA | 2986584 A1 | 11/2015 |
| CA | 2986584 A1 | 11/2015 |
| CA | 2975294 A1 | 8/2016 |
| CA | 2975294 A1 | 8/2016 |
| CA | 2995603 A1 | 2/2017 |
| CA | 2995603 A1 | 2/2017 |
| CA | 2753853 C | 4/2017 |
| CA | 2702615 C | 6/2017 |
| CA | 2702615 C | 6/2017 |
| CA | 2744395 C | 8/2017 |
| CA | 2744395 C | 8/2017 |
| CA | 2753853 A1 | 9/2017 |
| CA | 3020238 A1 | 11/2017 |
| CA | 3020238 A1 | 11/2017 |
| CA | 3033666 A1 | 2/2018 |
| CA | 3033666 A1 | 2/2018 |
| CA | 3031572 A1 | 3/2018 |
| CA | 3031572 A1 | 3/2018 |
| CA | 3022641 A1 | 5/2018 |
| CA | 3022641 A1 | 5/2018 |
| CA | 3044062 A1 | 6/2018 |
| CA | 3044062 A1 | 6/2018 |
| CA | 3048893 A1 | 7/2018 |
| CA | 3048893 A1 | 7/2018 |
| CA | 3049792 A1 | 7/2018 |
| CA | 3049792 A1 | 7/2018 |
| CA | 3046693 A1 | 8/2018 |
| CA | 3046693 A1 | 8/2018 |
| CA | 2778944 C | 8/2019 |
| CA | 2778944 C | 8/2019 |
| CN | 2855366 Y | 1/2007 |
| CN | 2855366 Y | 1/2007 |
| CN | 100584292 C | 1/2010 |
| CN | 100584292 C | 1/2010 |
| CN | 101677820 A | 3/2010 |
| CN | 101677820 A | 3/2010 |
| CN | 101677851 A | 3/2010 |
| CN | 101677851 A | 3/2010 |
| CN | 102858272 A | 1/2013 |
| CN | 102858272 A | 1/2013 |
| CN | 102869320 A | 1/2013 |
| CN | 102869320 A | 1/2013 |
| CN | 102892384 A | 1/2013 |
| CN | 102892384 A | 1/2013 |
| CN | 103118630 A | 5/2013 |
| CN | 103118630 A | 5/2013 |
| CN | 103189015 A | 7/2013 |
| CN | 103189015 A | 7/2013 |
| CN | 103228231 A | 7/2013 |
| CN | 103228231 A | 7/2013 |
| CN | 103298426 A | 9/2013 |
| CN | 103298426 A | 9/2013 |
| CN | 103370035 A | 10/2013 |
| CN | 103370035 A | 10/2013 |
| CN | 103391756 A | 11/2013 |
| CN | 103391756 A | 11/2013 |
| CN | 102245120 B | 8/2014 |
| CN | 102245120 B | 8/2014 |
| CN | 104220027 A | 12/2014 |
| CN | 104220027 A | 12/2014 |
| CN | 102917668 B | 1/2015 |
| CN | 102917668 B | 1/2015 |
| CN | 104394803 A | 3/2015 |
| CN | 104394803 A | 3/2015 |
| CN | 104582637 A | 4/2015 |
| CN | 104582637 A | 4/2015 |
| CN | 102905647 B | 7/2015 |
| CN | 102905647 B | 7/2015 |
| CN | 103648570 B | 9/2015 |
| CN | 103648570 B | 9/2015 |
| CN | 104884000 A | 9/2015 |
| CN | 104884000 A | 9/2015 |
| CN | 104160076 B | 12/2015 |
| CN | 104160076 B | 12/2015 |
| CN | 105380730 A | 3/2016 |
| CN | 105380730 A | 3/2016 |
| CN | 105451687 A | 3/2016 |
| CN | 105451687 A | 3/2016 |
| CN | 105520792 A | 4/2016 |
| CN | 105520792 A | 4/2016 |
| CN | 105530893 A | 4/2016 |
| CN | 105530893 A | 4/2016 |
| CN | 102458309 B | 5/2016 |
| CN | 102458309 B | 5/2016 |
| CN | 103200900 B | 5/2016 |
| CN | 103200900 B | 5/2016 |
| CN | 105555232 A | 5/2016 |
| CN | 105555232 A | 5/2016 |
| CN | 105578992 A | 5/2016 |
| CN | 105578992 A | 5/2016 |
| CN | 103338709 B | 6/2016 |
| CN | 103338709 B | 6/2016 |
| CN | 105658178 A | 6/2016 |
| CN | 105658178 A | 6/2016 |
| CN | 105792780 A | 7/2016 |
| CN | 105792780 A | 7/2016 |
| CN | 103347467 B | 8/2016 |
| CN | 103347467 B | 8/2016 |
| CN | 103648439 B | 8/2016 |
| CN | 103648439 B | 8/2016 |
| CN | 103889472 B | 8/2016 |
| CN | 103889472 B | 8/2016 |
| CN | 105899150 A | 8/2016 |
| CN | 105899150 A | 8/2016 |
| CN | 103153232 B | 9/2016 |
| CN | 103153232 B | 9/2016 |
| CN | 106061437 A | 10/2016 |
| CN | 106061437 A | 10/2016 |
| CN | 106068109 A | 11/2016 |
| CN | 106068109 A | 11/2016 |
| CN | 106073946 A | 11/2016 |
| CN | 106073946 A | 11/2016 |
| CN | 106255475 A | 12/2016 |
| CN | 106255475 A | 12/2016 |
| CN | 103917194 B | 2/2017 |
| CN | 103917194 B | 2/2017 |
| CN | 106456324 A | 2/2017 |

(56) References Cited

FOREIGN PATENT DOCUMENTS

| | | |
|---|---|---|
| CN | 106456324 A | 2/2017 |
| CN | 106456325 A | 2/2017 |
| CN | 106456325 A | 2/2017 |
| CN | 105073068 B | 3/2017 |
| CN | 105073068 B | 3/2017 |
| CN | 106470641 A | 3/2017 |
| CN | 106470641 A | 3/2017 |
| CN | 105451684 B | 4/2017 |
| CN | 105451684 B | 4/2017 |
| CN | 106573129 A | 4/2017 |
| CN | 106573129 A | 4/2017 |
| CN | 103945792 B | 5/2017 |
| CN | 103945792 B | 5/2017 |
| CN | 106659394 A | 5/2017 |
| CN | 106659394 A | 5/2017 |
| CN | 106716098 A | 5/2017 |
| CN | 106716098 A | 5/2017 |
| CN | 106794063 A | 5/2017 |
| CN | 106794063 A | 5/2017 |
| CN | 106890035 A | 6/2017 |
| CN | 106890035 A | 6/2017 |
| CN | 106943207 A | 7/2017 |
| CN | 106943207 A | 7/2017 |
| CN | 106999054 A | 8/2017 |
| CN | 106999054 A | 8/2017 |
| CN | 106999281 A | 8/2017 |
| CN | 106999281 A | 8/2017 |
| CN | 104114127 B | 9/2017 |
| CN | 104114127 B | 9/2017 |
| CN | 107115161 A | 9/2017 |
| CN | 107115161 A | 9/2017 |
| CN | 107249482 A | 10/2017 |
| CN | 107249482 A | 10/2017 |
| CN | 107260366 A | 10/2017 |
| CN | 107260366 A | 10/2017 |
| CN | 104918582 B | 11/2017 |
| CN | 104918582 B | 11/2017 |
| CN | 107374783 A | 11/2017 |
| CN | 107374783 A | 11/2017 |
| CN | 107427364 A | 12/2017 |
| CN | 107427364 A | 12/2017 |
| CN | 106255476 B | 1/2018 |
| CN | 106255476 B | 1/2018 |
| CN | 107530157 A | 1/2018 |
| CN | 107530157 A | 1/2018 |
| CN | 107530167 A | 1/2018 |
| CN | 107530167 A | 1/2018 |
| CN | 107530177 A | 1/2018 |
| CN | 107530177 A | 1/2018 |
| CN | 107613908 A | 1/2018 |
| CN | 107613908 A | 1/2018 |
| CN | 104869948 B | 2/2018 |
| CN | 104869948 B | 2/2018 |
| CN | 107714240 A | 2/2018 |
| CN | 107714240 A | 2/2018 |
| CN | 107920897 A | 4/2018 |
| CN | 107920897 A | 4/2018 |
| CN | 104853696 B | 6/2018 |
| CN | 104853696 B | 6/2018 |
| CN | 108135696 A | 6/2018 |
| CN | 108135696 A | 6/2018 |
| CN | 108430392 A | 8/2018 |
| CN | 108430392 A | 8/2018 |
| CN | 108472142 A | 8/2018 |
| CN | 108472142 A | 8/2018 |
| CN | 106726007 B | 11/2018 |
| CN | 106726007 B | 11/2018 |
| CN | 109124829 A | 1/2019 |
| CN | 109124829 A | 1/2019 |
| CN | 109199641 A | 1/2019 |
| CN | 109199641 A | 1/2019 |
| CN | 109561962 A | 4/2019 |
| CN | 109561962 A | 4/2019 |
| CN | 109567991 A | 4/2019 |
| CN | 109567991 A | 4/2019 |
| CN | 109862835 A | 6/2019 |
| CN | 109862835 A | 6/2019 |
| CN | 109906063 A | 6/2019 |
| CN | 109906063 A | 6/2019 |
| CN | 109996581 A | 7/2019 |
| CN | 109996581 A | 7/2019 |
| CN | 110013358 A | 7/2019 |
| CN | 110013358 A | 7/2019 |
| CN | 110290764 A | 9/2019 |
| CN | 110290764 A | 9/2019 |
| DE | 102014102648 A1 | 9/2015 |
| DE | 102014102648 A1 | 9/2015 |
| DE | 102014102650 A1 | 9/2015 |
| DE | 102014102650 A1 | 9/2015 |
| DE | 102014102718 A1 | 9/2015 |
| DE | 102014102718 A1 | 9/2015 |
| DE | 102014102722 A1 | 9/2015 |
| DE | 102014102722 A1 | 9/2015 |
| DE | 202017104793 U1 | 11/2018 |
| DE | 202017104793 U1 | 11/2018 |
| DE | 202016008737 U1 | 4/2019 |
| DE | 202016008737 U1 | 4/2019 |
| DK | 2549953 T3 | 2/2017 |
| DK | 2549953 T3 | 2/2017 |
| DK | 2254514 T3 | 12/2018 |
| DK | 2254514 T3 | 12/2018 |
| EA | 027348 B1 | 7/2017 |
| EA | 027348 B1 | 7/2017 |
| EP | 0902704 A1 | 3/1999 |
| EP | 0902704 A4 | 3/1999 |
| EP | 1301225 A2 | 4/2003 |
| EP | 1684666 A2 | 8/2006 |
| EP | 1684666 A2 | 8/2006 |
| EP | 1996246 A2 | 12/2008 |
| EP | 1996246 A2 | 12/2008 |
| EP | 2211779 A1 | 8/2010 |
| EP | 2211779 A1 | 8/2010 |
| EP | 2254513 A1 | 12/2010 |
| EP | 2254513 A1 | 12/2010 |
| EP | 2263605 A1 | 12/2010 |
| EP | 2263605 A1 | 12/2010 |
| EP | 2273947 A1 | 1/2011 |
| EP | 2273947 A1 | 1/2011 |
| EP | 2296744 A1 | 3/2011 |
| EP | 2296744 A1 | 3/2011 |
| EP | 2379008 A2 | 10/2011 |
| EP | 2379008 A2 | 10/2011 |
| EP | 2400926 A2 | 1/2012 |
| EP | 2400926 A2 | 1/2012 |
| EP | 2427145 A2 | 3/2012 |
| EP | 2427145 A2 | 3/2012 |
| EP | 1582178 B1 | 9/2012 |
| EP | 1582178 B1 | 9/2012 |
| EP | 2542186 A2 | 1/2013 |
| EP | 2542186 A2 | 1/2013 |
| EP | 2558030 A1 | 2/2013 |
| EP | 2558030 A1 | 2/2013 |
| EP | 2560579 A1 | 2/2013 |
| EP | 2560579 A1 | 2/2013 |
| EP | 2575681 A1 | 4/2013 |
| EP | 2575681 A1 | 4/2013 |
| EP | 2603172 A2 | 6/2013 |
| EP | 2603172 A2 | 6/2013 |
| EP | 2637607 A1 | 9/2013 |
| EP | 2637607 A1 | 9/2013 |
| EP | 2651337 A2 | 10/2013 |
| EP | 2651337 A2 | 10/2013 |
| EP | 2658476 A1 | 11/2013 |
| EP | 2658476 A1 | 11/2013 |
| EP | 2699201 A1 | 2/2014 |
| EP | 2699201 A1 | 2/2014 |
| EP | 2405966 B1 | 4/2014 |
| EP | 2405966 B1 | 4/2014 |
| EP | 2055263 B1 | 6/2014 |
| EP | 2055263 B1 | 6/2014 |
| EP | 2741711 A2 | 6/2014 |
| EP | 2741711 A2 | 6/2014 |
| EP | 2793763 A1 | 10/2014 |
| EP | 2793763 A1 | 10/2014 |

(56) References Cited

FOREIGN PATENT DOCUMENTS

| | | | |
|---|---|---|---|
| EP | 2822503 A2 | 1/2015 |
| EP | 2822503 A2 | 1/2015 |
| EP | 2538879 B1 | 4/2015 |
| EP | 2538879 B1 | 4/2015 |
| EP | 2444031 B1 | 7/2015 |
| EP | 2444031 B1 | 7/2015 |
| EP | 1702247 B1 | 8/2015 |
| EP | 1702247 B1 | 8/2015 |
| EP | 2772228 B1 | 11/2015 |
| EP | 2772228 B1 | 11/2015 |
| EP | 2943160 A2 | 11/2015 |
| EP | 2943160 A2 | 11/2015 |
| EP | 2470098 B1 | 12/2015 |
| EP | 2470098 B1 | 12/2015 |
| EP | 1991168 B1 | 1/2016 |
| EP | 1991168 B1 | 1/2016 |
| EP | 2254512 B1 | 1/2016 |
| EP | 2254512 B1 | 1/2016 |
| EP | 2964152 A1 | 1/2016 |
| EP | 2964152 A1 | 1/2016 |
| EP | 2967853 A1 | 1/2016 |
| EP | 2967853 A1 | 1/2016 |
| EP | 2967860 A1 | 1/2016 |
| EP | 2967860 A1 | 1/2016 |
| EP | 2994073 A1 | 3/2016 |
| EP | 2994073 A1 | 3/2016 |
| EP | 3001978 A1 | 4/2016 |
| EP | 3001978 A1 | 4/2016 |
| EP | 3003187 A1 | 4/2016 |
| EP | 3003187 A1 | 4/2016 |
| EP | 3007649 A1 | 4/2016 |
| EP | 3007649 A1 | 4/2016 |
| EP | 3010447 A1 | 4/2016 |
| EP | 3010447 A1 | 4/2016 |
| EP | 3017792 A1 | 5/2016 |
| EP | 3017792 A1 | 5/2016 |
| EP | 3019092 A1 | 5/2016 |
| EP | 3019092 A1 | 5/2016 |
| EP | 2563236 B1 | 6/2016 |
| EP | 2563236 B1 | 6/2016 |
| EP | 3027143 A1 | 6/2016 |
| EP | 3027143 A1 | 6/2016 |
| EP | 3037064 A1 | 6/2016 |
| EP | 3037064 A1 | 6/2016 |
| EP | 2211758 B1 | 7/2016 |
| EP | 2211758 B1 | 7/2016 |
| EP | 3052053 A1 | 8/2016 |
| EP | 3052053 A1 | 8/2016 |
| EP | 3060140 A1 | 8/2016 |
| EP | 3060140 A1 | 8/2016 |
| EP | 3062745 A1 | 9/2016 |
| EP | 3062745 A1 | 9/2016 |
| EP | 3071149 A1 | 9/2016 |
| EP | 3071149 A1 | 9/2016 |
| EP | 2282700 B1 | 11/2016 |
| EP | 2282700 B1 | 11/2016 |
| EP | 2967854 B1 | 11/2016 |
| EP | 2967854 B1 | 11/2016 |
| EP | 1998713 B1 | 12/2016 |
| EP | 1998713 B1 | 12/2016 |
| EP | 3099271 A1 | 12/2016 |
| EP | 3099271 A1 | 12/2016 |
| EP | 3100701 A1 | 12/2016 |
| EP | 3100701 A1 | 12/2016 |
| EP | 3141219 A1 | 3/2017 |
| EP | 3141219 A1 | 3/2017 |
| EP | 3157469 A1 | 4/2017 |
| EP | 3157469 A1 | 4/2017 |
| EP | 2538880 B1 | 5/2017 |
| EP | 2538880 B1 | 5/2017 |
| EP | 2967852 B1 | 6/2017 |
| EP | 2967852 B1 | 6/2017 |
| EP | 3174503 A1 | 6/2017 |
| EP | 3174503 A1 | 6/2017 |
| EP | 3182931 A1 | 6/2017 |
| EP | 3182931 A1 | 6/2017 |
| EP | 2830536 B1 | 8/2017 |
| EP | 2830536 B1 | 8/2017 |
| EP | 2830537 B1 | 9/2017 |
| EP | 2830537 B1 | 9/2017 |
| EP | 2720642 B1 | 10/2017 |
| EP | 2720642 B1 | 10/2017 |
| EP | 3232941 A1 | 10/2017 |
| EP | 3232941 A1 | 10/2017 |
| EP | 3256076 A1 | 12/2017 |
| EP | 3256076 A1 | 12/2017 |
| EP | 3281608 A1 | 2/2018 |
| EP | 3281608 A1 | 2/2018 |
| EP | 2608815 B1 | 3/2018 |
| EP | 2608815 B1 | 3/2018 |
| EP | 3310302 A1 | 4/2018 |
| EP | 3310302 A1 | 4/2018 |
| EP | 3311778 A1 | 4/2018 |
| EP | 3311778 A1 | 4/2018 |
| EP | 3337412 A1 | 6/2018 |
| EP | 3337412 A1 | 6/2018 |
| EP | 3340931 A1 | 7/2018 |
| EP | 3340931 A1 | 7/2018 |
| EP | 3344188 A1 | 7/2018 |
| EP | 3344188 A1 | 7/2018 |
| EP | 3344197 A1 | 7/2018 |
| EP | 3344197 A1 | 7/2018 |
| EP | 3345573 A1 | 7/2018 |
| EP | 3345573 A1 | 7/2018 |
| EP | 2822473 B1 | 8/2018 |
| EP | 2822473 B1 | 8/2018 |
| EP | 3354208 A1 | 8/2018 |
| EP | 3354208 A1 | 8/2018 |
| EP | 3370649 A1 | 9/2018 |
| EP | 3370649 A1 | 9/2018 |
| EP | 3372198 A1 | 9/2018 |
| EP | 3372198 A1 | 9/2018 |
| EP | 3372199 A1 | 9/2018 |
| EP | 3372199 A1 | 9/2018 |
| EP | 3375411 A1 | 9/2018 |
| EP | 3375411 A1 | 9/2018 |
| EP | 2928538 B1 | 11/2018 |
| EP | 2928538 B1 | 11/2018 |
| EP | 3399947 A1 | 11/2018 |
| EP | 3399947 A1 | 11/2018 |
| EP | 3400913 A1 | 11/2018 |
| EP | 3400913 A1 | 11/2018 |
| EP | 3406224 A1 | 11/2018 |
| EP | 3406224 A1 | 11/2018 |
| EP | 2555709 B1 | 12/2018 |
| EP | 2555709 B1 | 12/2018 |
| EP | 3417813 A1 | 12/2018 |
| EP | 3417813 A1 | 12/2018 |
| EP | 3426188 A1 | 1/2019 |
| EP | 3426188 A1 | 1/2019 |
| EP | 3429507 A1 | 1/2019 |
| EP | 3429507 A1 | 1/2019 |
| EP | 3431040 A1 | 1/2019 |
| EP | 3431040 A1 | 1/2019 |
| EP | 3432825 A1 | 1/2019 |
| EP | 3432825 A1 | 1/2019 |
| EP | 3432834 A1 | 1/2019 |
| EP | 3432834 A1 | 1/2019 |
| EP | 3437669 A1 | 2/2019 |
| EP | 3437669 A1 | 2/2019 |
| EP | 3448312 A1 | 3/2019 |
| EP | 3448312 A1 | 3/2019 |
| EP | 3454787 A1 | 3/2019 |
| EP | 3454787 A1 | 3/2019 |
| EP | 2663259 B1 | 5/2019 |
| EP | 2663259 B1 | 5/2019 |
| EP | 3302364 B1 | 5/2019 |
| EP | 3302364 B1 | 5/2019 |
| EP | 3478224 A1 | 5/2019 |
| EP | 3478224 A1 | 5/2019 |
| EP | 3484411 A1 | 5/2019 |
| EP | 3484411 A1 | 5/2019 |
| EP | 3487420 A1 | 5/2019 |
| EP | 3487420 A1 | 5/2019 |

(56) References Cited

FOREIGN PATENT DOCUMENTS

| | | | |
|---|---|---|---|
| EP | 2560580 B1 | 6/2019 |
| EP | 2560580 B1 | 6/2019 |
| EP | 3508113 A1 | 7/2019 |
| EP | 3508113 A1 | 7/2019 |
| EP | 1301225 A4 | 8/2019 |
| EP | 3518748 A1 | 8/2019 |
| EP | 3518748 A1 | 8/2019 |
| EP | 3522830 A1 | 8/2019 |
| EP | 3522830 A1 | 8/2019 |
| EP | 3528749 A1 | 8/2019 |
| EP | 3528749 A1 | 8/2019 |
| EP | 3288495 B1 | 9/2019 |
| EP | 3288495 B1 | 9/2019 |
| EP | 3538024 A1 | 9/2019 |
| EP | 3538024 A1 | 9/2019 |
| EP | 3538025 A1 | 9/2019 |
| EP | 3538025 A1 | 9/2019 |
| EP | 3019123 B1 | 10/2019 |
| EP | 3019123 B1 | 10/2019 |
| EP | 3508113 A1 | 10/2019 |
| EP | 3552584 A1 | 10/2019 |
| EP | 3552584 A1 | 10/2019 |
| EP | 3552655 A1 | 10/2019 |
| EP | 3552655 A1 | 10/2019 |
| ES | 2369241 T3 | 11/2011 |
| ES | 2369241 T3 | 11/2011 |
| ES | 2647777 T3 | 12/2017 |
| ES | 2647777 T3 | 12/2017 |
| ES | 2664243 T3 | 4/2018 |
| ES | 2664243 T3 | 4/2018 |
| ES | 2675726 T3 | 7/2018 |
| ES | 2675726 T3 | 7/2018 |
| GB | 2539444 A | 12/2016 |
| GB | 2539444 A | 12/2016 |
| JP | 2003530956 A | 10/2003 |
| JP | 2003530956 A | 10/2003 |
| JP | 2005521513 A | 7/2005 |
| JP | 2005521513 A | 7/2005 |
| JP | 2008506459 A | 3/2008 |
| JP | 2008506459 A | 3/2008 |
| JP | 2008512211 A | 4/2008 |
| JP | 2008512211 A | 4/2008 |
| JP | 2009148579 A | 7/2009 |
| JP | 2009148579 A | 7/2009 |
| JP | 2009525138 A | 7/2009 |
| JP | 2009525138 A | 7/2009 |
| JP | 2009527316 A | 7/2009 |
| JP | 2009527316 A | 7/2009 |
| JP | 2009254864 A | 11/2009 |
| JP | 2009254864 A | 11/2009 |
| JP | 4426182 B2 | 3/2010 |
| JP | 4426182 B2 | 3/2010 |
| JP | 2010518947 A | 6/2010 |
| JP | 2010518947 A | 6/2010 |
| JP | 2010537680 A | 12/2010 |
| JP | 2010537680 A | 12/2010 |
| JP | 2011510797 A | 4/2011 |
| JP | 2011510797 A | 4/2011 |
| JP | 2013503009 A | 1/2013 |
| JP | 2013503009 A | 1/2013 |
| JP | 2013505082 A | 2/2013 |
| JP | 2013505082 A | 2/2013 |
| JP | 2013508027 A | 3/2013 |
| JP | 2013508027 A | 3/2013 |
| JP | 2013512765 A | 4/2013 |
| JP | 2013512765 A | 4/2013 |
| JP | 2013523261 A | 6/2013 |
| JP | 2013523261 A | 6/2013 |
| JP | 2013527010 A | 6/2013 |
| JP | 2013527010 A | 6/2013 |
| JP | 2013543399 A | 12/2013 |
| JP | 2013543399 A | 12/2013 |
| JP | 2014501563 A | 1/2014 |
| JP | 2014501563 A | 1/2014 |
| JP | 2014505537 A | 3/2014 |
| JP | 2014505537 A | 3/2014 |
| JP | 5527850 B2 | 6/2014 |
| JP | 5527850 B2 | 6/2014 |
| JP | 2014518697 A | 8/2014 |
| JP | 2014518697 A | 8/2014 |
| JP | 201422678 A | 9/2014 |
| JP | 2014522678 A | 9/2014 |
| JP | 2015503948 A | 2/2015 |
| JP | 2015503948 A | 2/2015 |
| JP | 2015510819 A | 4/2015 |
| JP | 2015510819 A | 4/2015 |
| JP | 2015517854 A | 6/2015 |
| JP | 2015517854 A | 6/2015 |
| JP | 5767764 B2 | 8/2015 |
| JP | 5767764 B2 | 8/2015 |
| JP | 5803010 B2 | 11/2015 |
| JP | 5803010 B2 | 11/2015 |
| JP | 2015531283 A | 11/2015 |
| JP | 2015531283 A | 11/2015 |
| JP | 2015534887 A | 12/2015 |
| JP | 2015534887 A | 12/2015 |
| JP | 2016503710 A | 2/2016 |
| JP | 2016503710 A | 2/2016 |
| JP | 2016506794 A | 3/2016 |
| JP | 2016506794 A | 3/2016 |
| JP | 2016508858 A | 3/2016 |
| JP | 2016508858 A | 3/2016 |
| JP | 2016517748 A | 6/2016 |
| JP | 2016517748 A | 6/2016 |
| JP | 2016520391 A | 7/2016 |
| JP | 2016520391 A | 7/2016 |
| JP | 2016526438 A | 9/2016 |
| JP | 2016526438 A | 9/2016 |
| JP | 2016530046 A | 9/2016 |
| JP | 2016530046 A | 9/2016 |
| JP | 2016533787 A | 11/2016 |
| JP | 2016533787 A | 11/2016 |
| JP | 2016540617 A | 12/2016 |
| JP | 2016540617 A | 12/2016 |
| JP | 2017000729 A | 1/2017 |
| JP | 2017000729 A | 1/2017 |
| JP | 2017504410 A | 2/2017 |
| JP | 2017504410 A | 2/2017 |
| JP | 2017515609 A | 6/2017 |
| JP | 2017515609 A | 6/2017 |
| JP | 2017516536 A | 6/2017 |
| JP | 2017516536 A | 6/2017 |
| JP | 2017516609 A | 6/2017 |
| JP | 2017516609 A | 6/2017 |
| JP | 2017131738 A | 8/2017 |
| JP | 2017131738 A | 8/2017 |
| JP | 2017159055 A | 9/2017 |
| JP | 2017159055 A | 9/2017 |
| JP | 2017529908 A | 10/2017 |
| JP | 2017529908 A | 10/2017 |
| JP | 2018501001 A | 1/2018 |
| JP | 2018501001 A | 1/2018 |
| JP | 2018501901 A | 1/2018 |
| JP | 2018501901 A | 1/2018 |
| JP | 2018506412 A | 3/2018 |
| JP | 2018506412 A | 3/2018 |
| JP | 6329570 B2 | 5/2018 |
| JP | 6329570 B2 | 5/2018 |
| JP | 2019134972 A | 5/2018 |
| JP | 2018515306 A | 6/2018 |
| JP | 2018515306 A | 6/2018 |
| JP | 2018118136 A | 8/2018 |
| JP | 2018118136 A | 8/2018 |
| JP | 2018532556 A | 11/2018 |
| JP | 2018532556 A | 11/2018 |
| JP | 2018535074 A | 11/2018 |
| JP | 2018535074 A | 11/2018 |
| JP | 2019500952 A | 1/2019 |
| JP | 2019500952 A | 1/2019 |
| JP | 2019501696 A | 1/2019 |
| JP | 2019501696 A | 1/2019 |
| JP | 2019501712 A | 1/2019 |
| JP | 2019501712 A | 1/2019 |
| JP | 6466853 B2 | 2/2019 |

(56) References Cited

FOREIGN PATENT DOCUMENTS

| | | | |
|---|---|---|---|
| JP | 6466853 B2 | 2/2019 |
| JP | 6480343 B2 | 3/2019 |
| JP | 6480343 B2 | 3/2019 |
| JP | 2019507664 A | 3/2019 |
| JP | 2019507664 A | 3/2019 |
| JP | 6506813 B2 | 4/2019 |
| JP | 6506813 B2 | 4/2019 |
| JP | 6526043 B2 | 6/2019 |
| JP | 6526043 B2 | 6/2019 |
| JP | 2019103821 A | 6/2019 |
| JP | 2019103821 A | 6/2019 |
| JP | 2019514490 A | 6/2019 |
| JP | 2019514490 A | 6/2019 |
| JP | 2019516527 A | 6/2019 |
| JP | 2019516527 A | 6/2019 |
| JP | 2019517346 A | 6/2019 |
| JP | 2019517346 A | 6/2019 |
| JP | 6568213 B2 | 8/2019 |
| JP | 6568213 B2 | 8/2019 |
| JP | 2019134972 A | 8/2019 |
| JP | 2019523090 A | 8/2019 |
| JP | 2019523090 A | 8/2019 |
| JP | 2019155178 A | 9/2019 |
| JP | 2019155178 A | 9/2019 |
| JP | 2019526303 A | 9/2019 |
| JP | 2019526303 A | 9/2019 |
| KR | 20010013991 A | 2/2001 |
| KR | 20010013991 A | 2/2001 |
| KR | 20120101625 A | 9/2012 |
| KR | 20120101625 A | 9/2012 |
| KR | 101223313 B1 | 1/2013 |
| KR | 101223313 B1 | 1/2013 |
| KR | 101354189 B1 | 1/2014 |
| KR | 101354189 B1 | 1/2014 |
| KR | 20140139060 A | 12/2014 |
| KR | 20140139060 A | 12/2014 |
| KR | 20150097757 A | 8/2015 |
| KR | 20150097757 A | 8/2015 |
| KR | 20160024992 A | 3/2016 |
| KR | 20160024992 A | 3/2016 |
| RU | 177405 U1 | 2/2018 |
| RU | 177405 U1 | 2/2018 |
| WO | 0044308 A2 | 8/2000 |
| WO | WO-0044308 A2 | 8/2000 |
| WO | 03072287 A1 | 9/2003 |
| WO | WO-03072287 A1 | 9/2003 |
| WO | 2004093728 A2 | 11/2004 |
| WO | WO-2004093728 A2 | 11/2004 |
| WO | 2006029062 A1 | 3/2006 |
| WO | WO-2006029062 A1 | 3/2006 |
| WO | 2006066150 A2 | 6/2006 |
| WO | WO-2006066150 A2 | 6/2006 |
| WO | 2007047945 A2 | 4/2007 |
| WO | WO-2007047945 A2 | 4/2007 |
| WO | 2007054015 A1 | 5/2007 |
| WO | WO-2007054015 A1 | 5/2007 |
| WO | 2007095233 A2 | 8/2007 |
| WO | WO-2007095233 A2 | 8/2007 |
| WO | 2007129220 A2 | 11/2007 |
| WO | WO-2007129220 A2 | 11/2007 |
| WO | 2008013915 A2 | 1/2008 |
| WO | WO-2008013915 A2 | 1/2008 |
| WO | 2008091925 A2 | 7/2008 |
| WO | WO-2008091925 A2 | 7/2008 |
| WO | 2008103280 A2 | 8/2008 |
| WO | WO-2008103280 A2 | 8/2008 |
| WO | WO-2019131148 A1 | 10/2008 |
| WO | 2009081396 A2 | 7/2009 |
| WO | 2009094188 A2 | 7/2009 |
| WO | 2009094189 A1 | 7/2009 |
| WO | 2009094197 A1 | 7/2009 |
| WO | 2009094501 A1 | 7/2009 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | 2009100242 A2 | 8/2009 |
| WO | WO-2009100242 A2 | 8/2009 |
| WO | 2010029190 A1 | 3/2010 |
| WO | WO-2010029190 A1 | 3/2010 |
| WO | WO-2018008019 A2 | 9/2010 |
| WO | 2010119110 A1 | 10/2010 |
| WO | WO-2010119110 A1 | 10/2010 |
| WO | 2011112706 A2 | 9/2011 |
| WO | WO-2011112706 A2 | 9/2011 |
| WO | 2011137531 A1 | 11/2011 |
| WO | WO-2011137531 A1 | 11/2011 |
| WO | 2012009558 A2 | 1/2012 |
| WO | WO-2012009558 A2 | 1/2012 |
| WO | WO 2012/035279 | 3/2012 |
| WO | 2012063228 A1 | 5/2012 |
| WO | 2012063242 A1 | 5/2012 |
| WO | WO-2012063228 A1 | 5/2012 |
| WO | WO-2012063242 A1 | 5/2012 |
| WO | 2012112469 A2 | 8/2012 |
| WO | WO-2012112469 A2 | 8/2012 |
| WO | 2012145545 A1 | 10/2012 |
| WO | WO-2012145545 A1 | 10/2012 |
| WO | 2012161786 A1 | 11/2012 |
| WO | WO-2012161786 A1 | 11/2012 |
| WO | 2012175483 A1 | 12/2012 |
| WO | 2012178115 A2 | 12/2012 |
| WO | WO-2012175483 A1 | 12/2012 |
| WO | WO-2012178115 A2 | 12/2012 |
| WO | 2013021375 A2 | 2/2013 |
| WO | WO-2013021375 A2 | 2/2013 |
| WO | 2013085719 A1 | 6/2013 |
| WO | WO-2013085719 A1 | 6/2013 |
| WO | 2013103612 A1 | 7/2013 |
| WO | WO-2013103612 A1 | 7/2013 |
| WO | 2013116785 A1 | 8/2013 |
| WO | WO-2013116785 A1 | 8/2013 |
| WO | 2013128436 A1 | 9/2013 |
| WO | WO-2013128436 A1 | 9/2013 |
| WO | 2013148019 A1 | 10/2013 |
| WO | WO-2013148019 A1 | 10/2013 |
| WO | 2013166356 A2 | 11/2013 |
| WO | WO-2013166356 A2 | 11/2013 |
| WO | 2013177684 A1 | 12/2013 |
| WO | 2013184945 A1 | 12/2013 |
| WO | WO-2013177684 A1 | 12/2013 |
| WO | WO-2013184945 A1 | 12/2013 |
| WO | 2014011330 A1 | 1/2014 |
| WO | WO-2014011330 A1 | 1/2014 |
| WO | 2014064695 A2 | 5/2014 |
| WO | WO-2014064695 A2 | 5/2014 |
| WO | 2014121042 A1 | 8/2014 |
| WO | WO-2014121042 A1 | 8/2014 |
| WO | 2014133667 A1 | 9/2014 |
| WO | 2014137805 A1 | 9/2014 |
| WO | 2014140230 A1 | 9/2014 |
| WO | WO-2014133667 A1 | 9/2014 |
| WO | WO-2014137805 A1 | 9/2014 |
| WO | WO-2014140230 A1 | 9/2014 |
| WO | 2014162306 A2 | 10/2014 |
| WO | 2014164151 A1 | 10/2014 |
| WO | 2014168655 A1 | 10/2014 |
| WO | WO-2014162306 A2 | 10/2014 |
| WO | WO-2014164151 A1 | 10/2014 |
| WO | WO-2014168655 A1 | 10/2014 |
| WO | 2015004173 A1 | 1/2015 |
| WO | WO-2015004173 A1 | 1/2015 |
| WO | 2015014960 A1 | 2/2015 |
| WO | 2015017075 A1 | 2/2015 |
| WO | WO-2015014960 A1 | 2/2015 |
| WO | WO-2015017075 A1 | 2/2015 |
| WO | 2015055605 A1 | 4/2015 |
| WO | 2015057735 A1 | 4/2015 |
| WO | 2015058039 A1 | 4/2015 |
| WO | 2015061021 A1 | 4/2015 |
| WO | WO-2015055605 A1 | 4/2015 |
| WO | WO-2015057735 A1 | 4/2015 |
| WO | WO-2015058039 A1 | 4/2015 |

(56) References Cited

FOREIGN PATENT DOCUMENTS

| | | |
|---|---|---|
| WO | WO-2015061021 A1 | 4/2015 |
| WO | 2015117025 A1 | 8/2015 |
| WO | 2015120122 A2 | 8/2015 |
| WO | 2015123607 A2 | 8/2015 |
| WO | 2015127264 A1 | 8/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | 2015142834 A1 | 9/2015 |
| WO | WO-2015142834 A1 | 9/2015 |
| WO | 2015153755 A2 | 10/2015 |
| WO | WO-2015153755 A2 | 10/2015 |
| WO | 2016011267 A1 | 1/2016 |
| WO | WO-2016011267 A1 | 1/2016 |
| WO | 2016025733 A1 | 2/2016 |
| WO | WO-2016025733 A1 | 2/2016 |
| WO | 2016083351 A1 | 6/2016 |
| WO | 2016097337 A1 | 6/2016 |
| WO | 2016100799 A1 | 6/2016 |
| WO | WO-2016083351 A1 | 6/2016 |
| WO | WO-2016097337 A1 | 6/2016 |
| WO | WO-2016100799 A1 | 6/2016 |
| WO | 2016118851 A1 | 7/2016 |
| WO | WO-2016118851 A1 | 7/2016 |
| WO | 2016130913 A1 | 8/2016 |
| WO | WO-2016130913 A1 | 8/2016 |
| WO | 2016148777 A1 | 9/2016 |
| WO | 2016149083 A1 | 9/2016 |
| WO | 2016150806 A1 | 9/2016 |
| WO | WO-2016149083 A1 | 9/2016 |
| WO | WO-2016150806 A1 | 9/2016 |
| WO | 2016189391 A2 | 12/2016 |
| WO | WO-2016189391 A2 | 12/2016 |
| WO | 2017040684 A1 | 3/2017 |
| WO | WO-2017040684 A1 | 3/2017 |
| WO | 2017096157 A1 | 6/2017 |
| WO | WO-2017096157 A1 | 6/2017 |
| WO | 2017114928 A1 | 7/2017 |
| WO | 2017120404 A1 | 7/2017 |
| WO | 2017121193 A1 | 7/2017 |
| WO | 2017121194 A1 | 7/2017 |
| WO | 2017121195 A1 | 7/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | 2017136596 A1 | 8/2017 |
| WO | WO-2017136596 A1 | 8/2017 |
| WO | 2017151292 A1 | 9/2017 |
| WO | 2017155892 A1 | 9/2017 |
| WO | 2017156352 A1 | 9/2017 |
| WO | 2017161204 A1 | 9/2017 |
| WO | 2017165842 A1 | 9/2017 |
| WO | WO-2016148777 A1 | 9/2017 |
| WO | WO-2017151292 A1 | 9/2017 |
| WO | WO-2017155892 A1 | 9/2017 |
| WO | WO-2017156352 A1 | 9/2017 |
| WO | WO-2017165842 A1 | 9/2017 |
| WO | 2017196511 A1 | 11/2017 |
| WO | 2017201082 A1 | 11/2017 |
| WO | 2017202042 A1 | 11/2017 |
| WO | WO-2017196511 A1 | 11/2017 |
| WO | WO-2017201082 A1 | 11/2017 |
| WO | WO-2017202042 A1 | 11/2017 |
| WO | 2017210356 A1 | 12/2017 |
| WO | 2017218375 A1 | 12/2017 |
| WO | WO-2017210356 A1 | 12/2017 |
| WO | WO-2017218375 A1 | 12/2017 |
| WO | 2018008019 A2 | 1/2018 |
| WO | WO-2019006383 A2 | 1/2018 |
| WO | 2018026445 A1 | 2/2018 |
| WO | 2018026904 A1 | 2/2018 |
| WO | 2018035105 A1 | 2/2018 |
| WO | WO-2018026445 A1 | 2/2018 |
| WO | WO-2018026904 A1 | 2/2018 |
| WO | WO-2018035105 A1 | 2/2018 |
| WO | 2018040244 A1 | 3/2018 |
| WO | 2018042439 A1 | 3/2018 |
| WO | 2018045156 A2 | 3/2018 |
| WO | WO-2018040244 A1 | 3/2018 |
| WO | WO-2018042439 A1 | 3/2018 |
| WO | WO-2018045156 A2 | 3/2018 |
| WO | 2018071115 A1 | 4/2018 |
| WO | WO-2018071115 A1 | 4/2018 |
| WO | 2018077143 A1 | 5/2018 |
| WO | 2018077146 A1 | 5/2018 |
| WO | 2018080328 A1 | 5/2018 |
| WO | 2018083493 A1 | 5/2018 |
| WO | 2018090576 A1 | 5/2018 |
| WO | 2018098032 A1 | 5/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | 2018106460 A1 | 6/2018 |
| WO | 2018119304 A1 | 6/2018 |
| WO | WO-2018106460 A1 | 6/2018 |
| WO | WO-2018119304 A1 | 6/2018 |
| WO | 2018138658 A1 | 8/2018 |
| WO | 2018145055 A1 | 8/2018 |
| WO | 2018156767 A1 | 8/2018 |
| WO | 2018156922 A1 | 8/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | 2018158747 A1 | 9/2018 |
| WO | 2018160790 A1 | 9/2018 |
| WO | 2018165358 A1 | 9/2018 |
| WO | 2018170149 A1 | 9/2018 |
| WO | 2018175220 A1 | 9/2018 |
| WO | 2018175619 A1 | 9/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | 2018178208 A1 | 10/2018 |
| WO | 2018178977 A1 | 10/2018 |
| WO | 2018183832 A1 | 10/2018 |
| WO | 2018184225 A1 | 10/2018 |
| WO | 2018184226 A1 | 10/2018 |
| WO | 2018187495 A1 | 10/2018 |
| WO | 2018187753 A1 | 10/2018 |
| WO | 2018191681 A1 | 10/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | 2018200531 A1 | 11/2018 |
| WO | 2018200942 A2 | 11/2018 |
| WO | 2018201111 A2 | 11/2018 |
| WO | 2018201212 A1 | 11/2018 |
| WO | 2018204106 A1 | 11/2018 |
| WO | 2018209302 A1 | 11/2018 |
| WO | 2018213209 A1 | 11/2018 |
| WO | 2018217525 A1 | 11/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |

(56) References Cited

FOREIGN PATENT DOCUMENTS

| | | |
|---|---|---|
| WO | 2018222799 A1 | 12/2018 |
| WO | 2018226628 A1 | 12/2018 |
| WO | WO-2018222799 A1 | 12/2018 |
| WO | WO-2018226628 A1 | 12/2018 |
| WO | 2019003221 A1 | 1/2019 |
| WO | 2019006383 A2 | 1/2019 |
| WO | 2019010458 A1 | 1/2019 |
| WO | 2019014473 A1 | 1/2019 |
| WO | 2019018319 A1 | 1/2019 |
| WO | 2019023385 A1 | 1/2019 |
| WO | WO-2019003221 A1 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | 2019026059 A1 | 2/2019 |
| WO | 2019032992 A2 | 2/2019 |
| WO | 2019037579 A1 | 2/2019 |
| WO | 2019040357 A1 | 2/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | 2019042472 A1 | 3/2019 |
| WO | 2019046099 A1 | 3/2019 |
| WO | 2019046205 A1 | 3/2019 |
| WO | 2019051168 A2 | 3/2019 |
| WO | 2019051180 A2 | 3/2019 |
| WO | 2019051587 A1 | 3/2019 |
| WO | 2019055577 A1 | 3/2019 |
| WO | 2019058178 A1 | 3/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | 2019067219 A1 | 4/2019 |
| WO | WO-2019067219 A1 | 4/2019 |
| WO | 2019081689 A1 | 5/2019 |
| WO | 2019081985 A2 | 5/2019 |
| WO | 2019086958 A1 | 5/2019 |
| WO | 2019089136 A1 | 5/2019 |
| WO | 2019089821 A1 | 5/2019 |
| WO | 2019093387 A1 | 5/2019 |
| WO | 2019095049 A1 | 5/2019 |
| WO | 2019096033 A1 | 5/2019 |
| WO | 2019099722 A2 | 5/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | 2019116322 A1 | 6/2019 |
| WO | 2019119674 A1 | 6/2019 |
| WO | 2019126518 A1 | 6/2019 |
| WO | WO-2019116322 A1 | 6/2019 |
| WO | WO-2019119674 A1 | 6/2019 |
| WO | WO-2019126518 A1 | 6/2019 |
| WO | 2019131148 A1 | 7/2019 |
| WO | 2019136162 A1 | 7/2019 |
| WO | 2019140293 A1 | 7/2019 |
| WO | 2019143775 A1 | 7/2019 |
| WO | 2019144036 A1 | 7/2019 |
| WO | WO-2017161204 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | 2019147585 A1 | 8/2019 |
| WO | 2019165213 A1 | 8/2019 |
| WO | WO-2019147585 A1 | 8/2019 |
| WO | WO-2019165213 A1 | 8/2019 |
| WO | 2019173475 A1 | 9/2019 |
| WO | WO-2019173475 A1 | 9/2019 |
| WO | 2019190800 A1 | 10/2019 |
| WO | 2019191102 A1 | 10/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
Office Action for U.S. Appl. No. 16/445,210, dated Jan. 28, 2021, 7 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 17/154,227, dated Mar. 29, 2021, 6 pages.
Office Action for U.S. Appl. No. 17/193,936, dated May 27, 2021, 6 pages.
International Search Report and Written Opinion for International Application No. PCT/US2021/013570, dated Apr. 1, 2021, 9 pages.
International Search Report and Written Opinion for International Application No. PCT/US2019/028822, dated Oct. 24, 2019, 14 pages.
Office Action for U.S. Appl. No. 17/167,983, dated Apr. 13, 2021, 20 pages.
Office Action for U.S. Appl. No. 17/154,438, dated May 3, 2021, 16 pages.

(56) References Cited

OTHER PUBLICATIONS

Office Action for U.S. Appl. No. 16/449,420, dated Sep. 1, 2021, 16 pages.
Office Action for U.S. Appl. No. 17/167,988, dated Sep. 22, 2021, 19 pages.
Office Action for U.S. Appl. No. 17/221,547, dated Aug. 4, 2021, 11 pages.
Office Action for U.S. Appl. No. 17/222,182, dated Sep. 2, 2021, 23 pages.
Office Action for U.S. Appl. No. 17/236,219, dated Aug. 4, 2021, 17 pages.

* cited by examiner

COLLAPSIBLE INNER FLOW CONTROL COMPONENT FOR SIDE-DELIVERED TRANSCATHETER HEART VALVE PROSTHESIS

CROSS-REFERENCE TO RELATED APPLICATIONS

This application claims priority to and the benefit of U.S. Provisional Application No. 62/797,201, filed Jan. 26, 2019, entitled "Collapsible Inner Flow Control Component for Orthogonal Transcatheter Heart Valve Prosthesis," the contents of which is hereby incorporated in its entirety by reference.

BACKGROUND OF THE INVENTION

Field of the Invention

The invention relates to a transcatheter heart valve replacement (A61F2/2412).

Description of the Related Art

In 1952 surgeons implanted the first mechanical heart valve, a ball valve that could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting disc technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The present invention is directed to a collapsible inner flow control component for a transcatheter heart valve replacement (A61F2/2412), the collapsible inner flow control component having leaflet frame foldable along a horizontal axis (z-axis, axis parallel to central axis of delivery catheter) and compressible along a vertical axis (y-axis), the valve replacement also having a proximal sub-annular anchoring tab and a distal sub-annular anchoring tab, and in particular a side delivered (delivered length-wise, along z-axis; orthogonal to the central valve axis) delivered transcatheter prosthetic heart valve having a annular outer support frame having compressible wire cells that facilitate rolling, folding, compressing in height and/or width, the valve length-wise, or orthogonal, to the central axis of the inner flow control component, allowing a very large diameter valve to be delivered and deployed from the inferior vena cava directly into the tricuspid valve, e.g. has a height of about 5-60 mm and a diameter of about 25-80 mm, without requiring an oversized diameter catheter and without requiring delivery and deployment from a catheter at an acute angle of approach.

Collapsible Inner

Accordingly, the present invention is directed to an inner flow control component for a side delivered heart valve, comprising: a leaflet frame with 2-4 flexible leaflets mounted thereon, the leaflet frame comprising two or more panels of diamond- or eye-shaped wire cells made from heat-set Nitinol and configured to be foldable along a z-axis from a rounded or cylindrical configuration to a flattened cylinder configuration, and compressible along a vertical axis y-axis to a shortened configuration, wherein the 2-4 leaflets are configured to permit blood flow in a first direction through an inflow end of the flow control component and block blood flow in a second direction, opposite the first direction, through an outflow end of the flow control component.

In one preferred embodiment, the inner flow control component in an expanded configuration forms a shape selected from a funnel, cylinder, flat cone, or circular hyperboloid.

In another preferred embodiment, the inner flow control component has a leaflet frame comprised of a braided, wire, or laser-cut wire frame.

In another preferred embodiment, the inner flow control component has a leaflet frame that has a side profile of a flat cone shape having a diameter R of 20-60 mm, a diameter r of 10-500 mm, where diameter R is great than diameter r, and a height of 5-60 mm.

Orthogonally Delivered Valve

Accordingly, the present invention is directed to a side delivered transcatheter prosthetic heart valve having a collapsible flow control component, comprising:
 (i) a self-expanding annular support frame, said annular support frame having a central channel and an outer perimeter wall circumscribing a central vertical axis in an expanded configuration, said annular support frame having a distal side and a proximal side, (ii) a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a horizontal axis (z-axis, axis parallel to central axis of delivery catheter) and compressible along a vertical axis (y-axis), (iii) a distal anchoring tab mounted on the distal side of the annular support frame, (iv) a proximal anchoring tab mounted on the proximal side of the annular support frame, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a lengthwise cylindrical axis of the delivery catheter, wherein the valve has a height of about 5-60 mm and a diameter of about 25-80 mm.

In another preferred embodiment of the invention, there is provided a valve wherein the annular support frame is comprised of a plurality of compressible wire cells having an orientation and cell geometry substantially orthogonal to the central vertical axis to minimize wire cell strain when the annular support frame is configured in a vertical compressed configuration, a rolled compressed configuration, or a folded compressed configuration.

In another preferred embodiment of the invention, there is provided a valve wherein the annular support frame has a lower body portion and an upper collar portion, wherein the lower body portion in an expanded configuration forms a shape selected from a funnel, cylinder, flat cone, or circular hyperboloid.

In another preferred embodiment of the invention, there is provided a valve wherein said annular support frame is comprised of a braided, wire, or laser-cut wire frame, and said annular support frame is covered with a biocompatible material.

In another preferred embodiment of the invention, there is provided a valve wherein the annular support frame has a side profile of a flat cone shape having a diameter R of 40-80 mm, a diameter r of 20-60 mm, and a height of 5-60 mm.

In another preferred embodiment of the invention, there is provided a valve wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another preferred embodiment of the invention, there is provided a valve wherein the annular support frame has a side profile of an hourglass shape having a top diameter R1 of 40-80 mm, a bottom diameter R2 of 50-70 mm, an internal diameter r of 20-60 mm, and a height of 5-60 mm.

In another preferred embodiment of the invention, there is provided a valve wherein the valve in an expanded configuration has a central vertical y-axis that is substantially parallel to the first direction.

In another preferred embodiment of the invention, there is provided a valve wherein the flow control component has an internal diameter of 20-60 mm and a height of 10-40 mm, and a plurality of leaflets of pericardial material joined to form a rounded cylinder at an inflow end and having a flat closable aperture at an outflow end.

In another preferred embodiment of the invention, there is provided a valve wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battens, rigid or semi-rigid panels, and combinations thereof.

In another preferred embodiment of the invention, there is provided a valve wherein the distal anchoring tab is comprised of wire loop, a wire frame, a laser cut frame, an integrated frame section, or a stent, and the distal anchoring tab extends from about 10-40 mm away from the distal side of the annular support frame.

In another preferred embodiment of the invention, there is provided a valve wherein the proximal anchoring tab is comprised of wire loop, a wire frame, a laser cut frame, an integrated frame section, or a stent, and the distal anchoring tab extends from about 10-40 mm away from the proximal side of the annular support frame.

In another preferred embodiment of the invention, there is provided a valve, further comprising an upper distal anchoring tab attached to a distal upper edge of the annular support frame, the upper distal anchoring tab comprised of wire loop, a wire frame, a laser cut frame, an integrated frame section, or a stent, and extends from about 2-20 mm away from the annular support frame.

In another preferred embodiment of the invention, there is provided a valve, comprising at least one tissue anchor connected to the annular support frame for engaging native tissue.

In another preferred embodiment of the invention, there is provided a valve, wherein the outer perimeter wall comprises a front wall portion that is a first flat panel and a back wall portion that is a second flat panel, and wherein a proximal fold area and a distal fold area each comprise a sewn seam, a fabric panel, a rigid hinge, or a flexible fabric span without any wire cells.

In another preferred embodiment of the invention, there is provided a valve, wherein the annular outer support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

Process for Manufacturing

In another preferred embodiment of the invention, there is provided a process for manufacturing a side delivered transcatheter prosthetic heart valve frame, comprising:

(i) using additive or subtractive metal or metal-alloy manufacturing to produce a self-expanding annular support frame, said annular support frame having a central channel and an outer perimeter wall circumscribing a central vertical axis in an expanded configuration, said annular support frame having a distal side and a proximal side, a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab mounted on the distal side of the annular support frame, a proximal anchoring tab mounted on the proximal side of the annular support frame, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a length-wise cylindrical axis of the delivery catheter, wherein the valve has a height of about 5-60 mm and a diameter of about 25-80 mm, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In another preferred embodiment of the invention, there is provided a process of manufacturing further comprising the steps of: (ii) mounting a flow control component within the valve frame, said flow control component configured to permit blood flow along the central vertical axis through an inflow end of the flow control component and block blood flow through an outflow end of the valve, and (iii) covering an outer surface of the valve frame with a pericardium material or similar biocompatible material.

Method of Compressing

In another preferred embodiment of the invention, there is provided a method for compressing an implantable prosthetic heart valve for length-wise orthogonal release of the valve from a delivery catheter, comprising the steps: (i) flattening or folding the implantable prosthetic heart valve from a cylindrical configuration into a flattened cylinder configuration wherein the x-axis of the compressed configuration of the valve is substantially parallel to a length-wise cylindrical axis of the delivery catheter, and (ii) vertically compressing the valve along the y-axis to a shortened configuration, wherein the implantable prosthetic heart valve comprises an annular support frame having a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab mounted on a distal side of the annular support frame, a proximal anchoring tab mounted on a proximal side of the annular support frame, wherein the valve has a height of about 5-60 mm and a diameter of about 25-80 mm.

In another preferred embodiment of the invention, there is provided a method of compressing, wherein the implantable prosthetic heart valve is reduced along the vertical y-axis and the width z-axis to a dimension from 18-24 Fr, or 6-8 mm.

Method for Delivery

In another preferred embodiment of the invention, there is provided a method for orthogonal delivery of implantable prosthetic heart valve in the body, the method comprising the steps: (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricuspid valve to the pulmonary artery or extends from the right atrium across the atrial septum in a transeptal access through the mitral valve and into a left ventricle; (ii) advancing a delivery catheter over the guide wire to a target location, where the target location is a right atrium of the tricuspid valve or a left atrium of the mitral valve; (iii) advancing and delivering an orthogonally compressed (compressed specifically for side-delivery) self-expandable prosthetic heart valve to the target location in the body, wherein a compressed configuration of the valve has a long x-axis substantially parallel to a length-wise cylindrical axis of the delivery catheter, wherein the expanded configuration of the valve has a height of about 5-60 mm and a diameter of about 25-80 mm, wherein the valve comprises an annular support frame having a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab is mounted on a distal side of the annular support frame, the distal anchoring tab having a length of 10-40 mm and a width of 2-10 mm, wherein the guide wire is threaded through a threading aperture on or within the distal anchoring tab, at least one proximal anchoring tab is mounted on a proximal side of the annular support frame, the proximal anchoring tab having a length of 2-25 mm and a width of 2-10 mm, and a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab; (iv) partially releasing the valve from the delivery catheter by advancing the sheath over the guide wire, and positioning the distal anchoring tab at a desired anchoring area of the target location, wherein the desired anchoring area is selected from a right ventricular outflow tract (RVOT) of a right ventricle, and a sub-annular area below an A1-P1 antero-lateral commissure of a mitral valve, wherein positioning the distal anchoring tab holds the valve at a raised angle of at least 30 degrees to a localized annular plane relative to the horizontal axis of the valve and the delivery catheter, wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve; (v) completing release of the entire valve from the delivery catheter by advancing the sheath over the guide wire, seating the valve in the native annulus by applying a downward force in the direction of the ventricle; and (vi) seating the at least one proximal anchoring tab at a second desired anchoring area.

In another preferred embodiment of the invention, there is provided a method for orthogonal delivery of implantable prosthetic heart valve to a desired location in the body, including the tricuspid and the mitral valve locations, the method comprising the steps: advancing a delivery catheter to the desired location in the body and delivering an expandable prosthetic heart valve to the desired location in the body by releasing the valve from the delivery catheter, wherein the valve comprises an annular support frame having a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab mounted on a distal side of the annular support frame, and a proximal anchoring tab mounted on a proximal side of the annular support frame, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the compressed configuration, wherein the valve has a height of about 5-60 mm and a diameter of about 25-80 mm.

In another preferred embodiment of the invention, there is provided a method of delivery, wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In another preferred embodiment of the invention, there is provided a method of delivery, comprising the additional step of anchoring one or more tissue anchors attached to the valve into native tissue.

In another preferred embodiment of the invention, there is provided a method of delivery, comprising the additional step of positioning the distal anchoring tab of the heart valve prosthesis into the right ventricular outflow tract of the right ventricle.

In another preferred embodiment of the invention, there is provided a method of delivery, comprising the additional steps of positioning the distal anchoring tab of the heart valve prosthesis into the right ventricular outflow tract of the right ventricle, and positioning an upper distal anchoring tab into a supra-annular position, and the upper distal anchoring tab providing a supra-annular downward force in the direction of the ventricle and distal anchoring tab providing a sub-annular upward force in the direction of the atrium.

In another preferred embodiment of the invention, there is provided a method of delivery, comprising [[the]] the additional step of rotating the heart valve prosthesis using a steerable catheter along an axis parallel to the plane of the valve annulus.

Method for Loading

In another preferred embodiment of the invention, there is provided a method for orthogonally loading an implantable prosthetic heart valve into a delivery catheter, the method comprising the steps: loading an implantable prosthetic heart valve into a tapering fixture or funnel attached to a delivery catheter, wherein the valve comprises a annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein said loading is perpendicular or substantially orthogonal to the first direction, wherein the valve is compressible to a compressed configuration for introduction into the body using a delivery catheter for implanting at a desired location in the body, said compressed configuration having a long x-axis oriented at an intersecting angle of between 45-135 degrees to the first direction, and expandable to an expanded configuration having a long x-axis oriented at an intersecting angle of between 45-135 degrees to the first direction, wherein the long x-axis of the compressed configuration of the valve is substantially parallel to a length-wise cylindrical axis of the delivery catheter, wherein the valve has a height of about 5-60 mm and a diameter of about 25-80 mm.

In another preferred embodiment of the invention, there is provided a method for loading, wherein the step of loading includes attaching a loading accessory to a valve sidewall, to a valve cuff, to the distal anchoring tab, to the proximal anchoring tab, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve.

Method for Improving Flow

In another preferred embodiment of the invention, there is provided a method for improving hemodynamic flow during implantation of a transcatheter prosthetic heart valve, comprising: advancing a delivery catheter to the desired location in the body and delivering the valve of claim 1 to the desired location in the body; partially releasing the valve from the delivery catheter to establish blood flow around the partially released valve and establish blood flow through the flow control component; completely releasing the valve from the delivery catheter while maintaining attachment to the valve with a positioning catheter or wire to transition to increased blood flow through the flow control component and decreasing blood flow around the valve; and deploying the valve into a final mounted position to transition to complete blood flow through the flow control component and minimal or no blood flow around the valve, and disconnecting and withdrawing the positioning catheter or wire from the valve.

In another preferred embodiment of the invention, there is provided a method for improving flow, wherein the distal anchoring tab is an RVOT tab positioned in the RVOT during the transition from partial release of the valve to complete release of the valve.

BRIEF DESCRIPTION OF THE SEVERAL VIEWS OF DRAWING

FIG. 1 is an illustration of a SIDE PERSPECTIVE view of a side delivered transcatheter heart valve with a collapsible flow control component mounted within the annular outer support frame, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, and the valve having a superelastic wire loop distal tab and a superelastic wire loop proximal tab according to the invention.

FIG. 2 is an illustration of a SIDE PERSPECTIVE view of an exploded view of an embodiment having three leaflet cusp or pockets mounted within a foldable and compressible inner wire frame, the inner is mounted within an outer wire frame which has a collar component attached circumferentially at a top edge of the outer wire frame, a dual tab component, and a mesh component, according to the invention.

FIG. 3 is an illustration of a SIDE PERSPECTIVE view of a side delivered transcatheter heart valve with a collapsible flow control component mounted within the annular outer support frame, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, and the valve having a superelastic wire loop distal tab and a superelastic wire loop proximal tab according to the invention.

FIG. 4 is an illustration of a SIDE PERSPECTIVE view of an exploded view of an embodiment having three leaflet cusp or pockets mounted within a foldable and compressible inner wire frame, the inner is mounted within an outer wire frame which has a collar component attached circumferentially at a top edge of the outer wire frame, a pair of integrated, independent tab components, and a mesh component, according to the invention.

Figure 31:
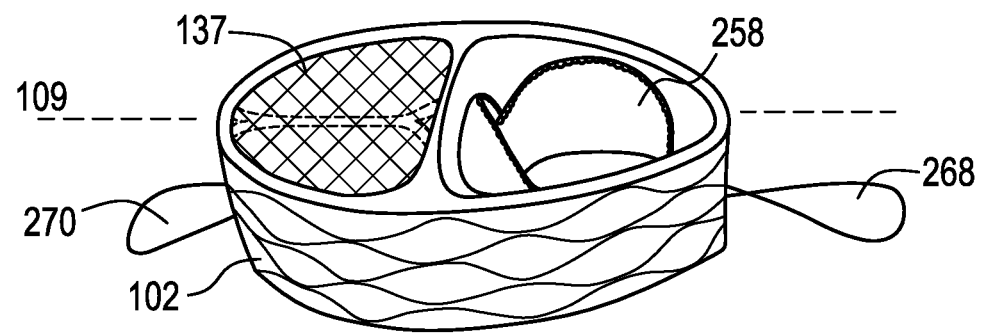

FIG. 31 is an illustration of a TOP PERSPECTIVE view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three sewn leaflet pockets/cusps, an inner spacer frame, and a mesh cover over the spacer frame, fold-line is shown as a dashed line on the mesh cover, according to the invention.

Figure 32:
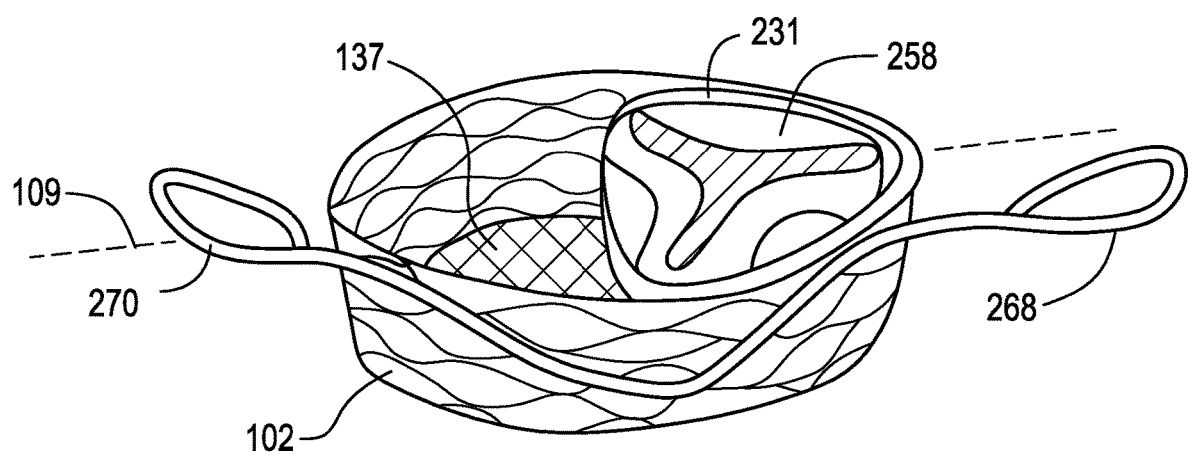

FIG. 32 is an illustration of a BOTTOM PERSPECTIVE view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three sewn leaflet pockets/cusps, an inner spacer frame and a mesh cover over the spacer frame, fold-line is shown as a dashed line on the mesh cover, and hemodynamic washing cavity is shown under the covered inner spacer frame, according to the invention.

Figure 33:
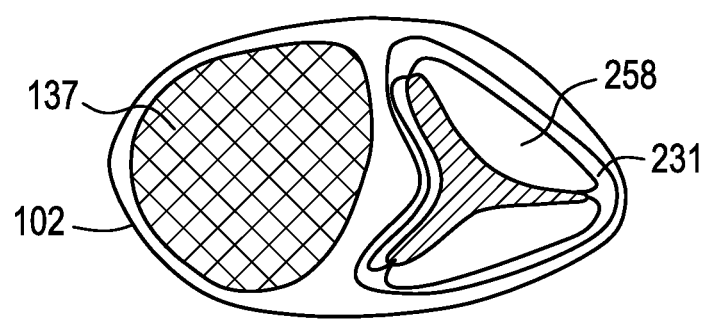

FIG. 33 is an illustration of a TOP view of an assembled valve with an outer frame, a flow control component having an inner leaflet frame and three sewn leaflet pockets/cusps, an inner spacer frame, and a mesh cover over the spacer frame, according to the invention.

Figure 34:
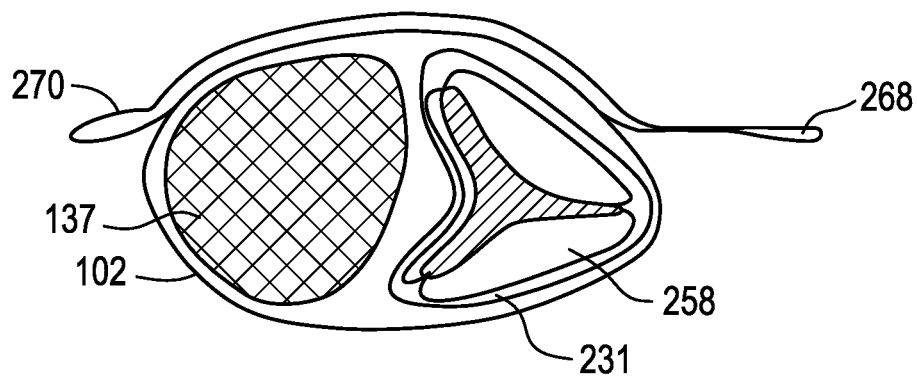

FIG. 34 is an illustration of a TOP view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three sewn leaflet pockets/cusps, an inner spacer frame, and a mesh cover over the spacer frame, according to the invention.

Figure 35:
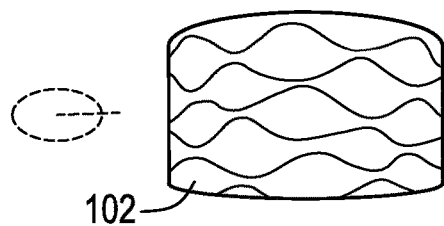

FIG. 35 is an illustration of a front PLAN view of a non-tabbed valve with foldable and compressible wireframe construction visible, according to the invention.

Figure 36:
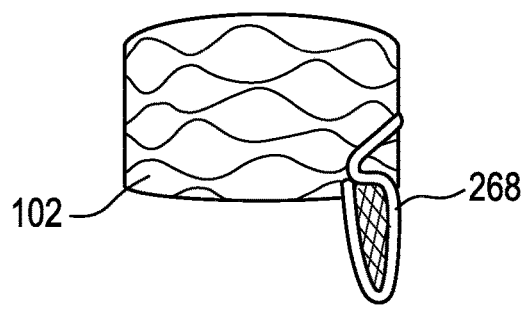

FIG. 36 is an illustration of a front PLAN view of a tabbed valve with sub-annular anchoring and/or positioning tab extending towards the viewer, and with foldable and compressible wireframe construction visible, according to the invention.

Figure 37:
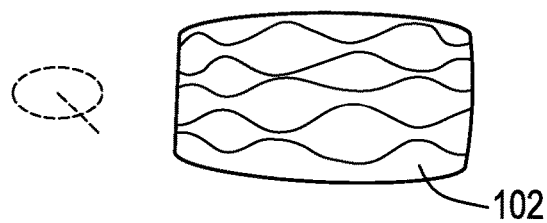

FIG. 37 is an illustration of a front anterior PLAN view of a non-tabbed valve with foldable and compressible wireframe construction visible, according to the invention.

Figure 38:
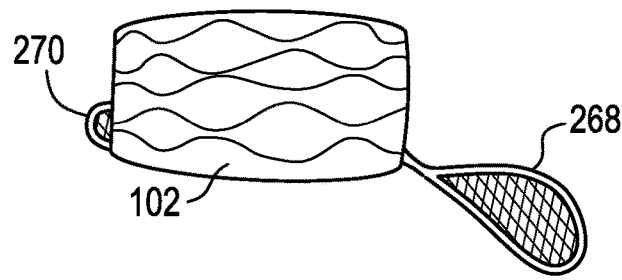

FIG. 38 is an illustration of a front anterior PLAN view of a tabbed valve with sub-annular anchoring and/or positioning tab extending towards the viewer, and second sub-annular tab extending away, and with foldable and compressible wireframe construction visible, according to the invention.

Figure 39:
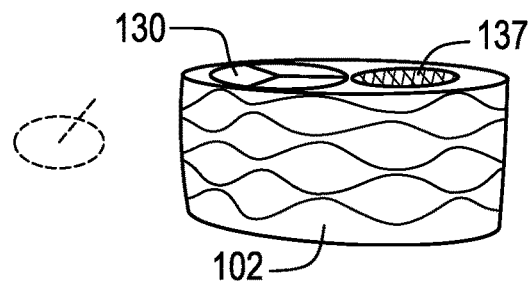

FIG. 39 is an illustration of a front septal PLAN view of a non-tabbed valve with foldable and compressible wireframe construction visible, according to the invention.

Figure 40:
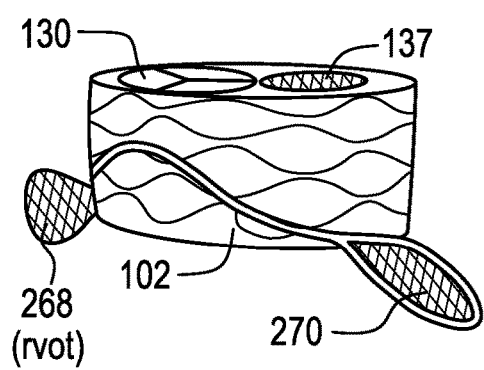

FIG. 40 is an illustration of a front septal PLAN view of a tabbed valve with sub-annular RVOT anchoring and/or positioning tab extending left, and second sub-annular proximal tab extending right, and with foldable and compressible wireframe construction visible, and with inner flow control component in a distal position and mesh-covered inner spacer frame in a proximal location, according to the invention.

Figure 41:
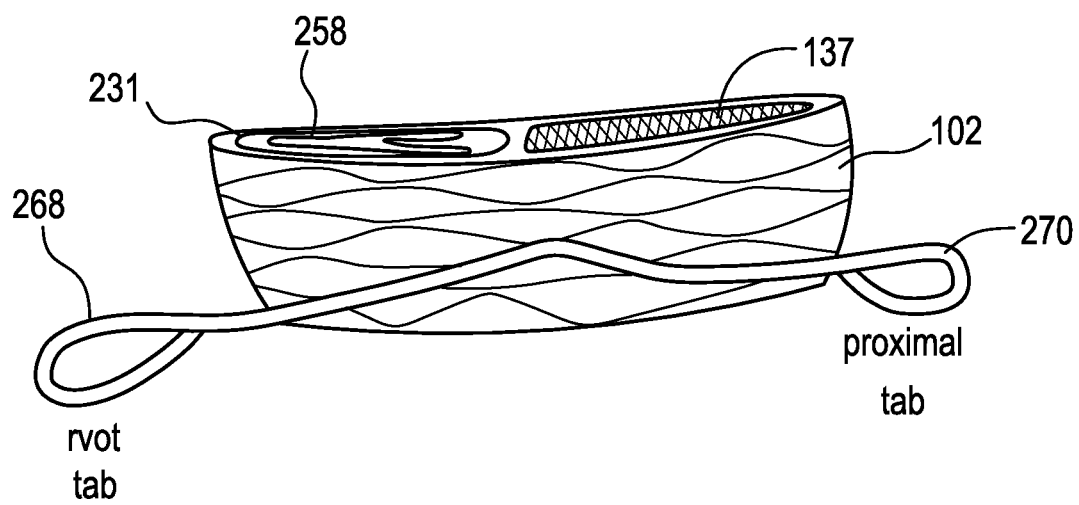

FIG. 41 is an illustration of a side septal PLAN view of a tabbed valve with sub-annular anchoring and/or positioning tab extending towards the viewer, and second sub-annular tab extending away, and with foldable and compressible wireframe construction visible, according to the invention.

Figure 42:
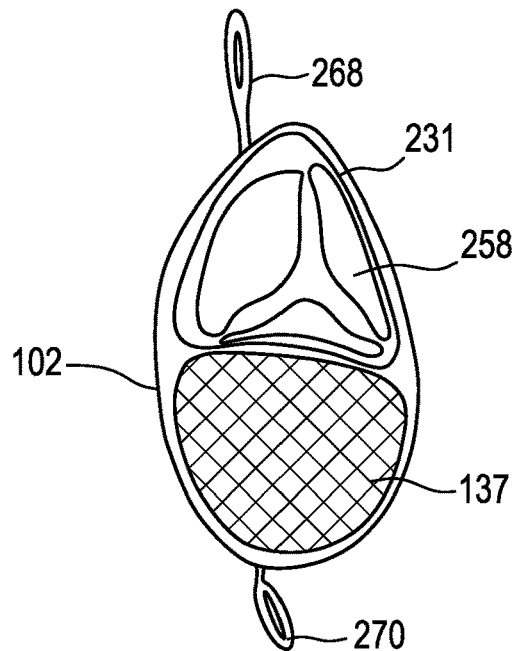

FIG. 42 is an illustration of a TOP view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three sewn leaflet pockets/cusps, an inner spacer frame, and a mesh cover over the spacer frame, according to the invention.

Figure 43:
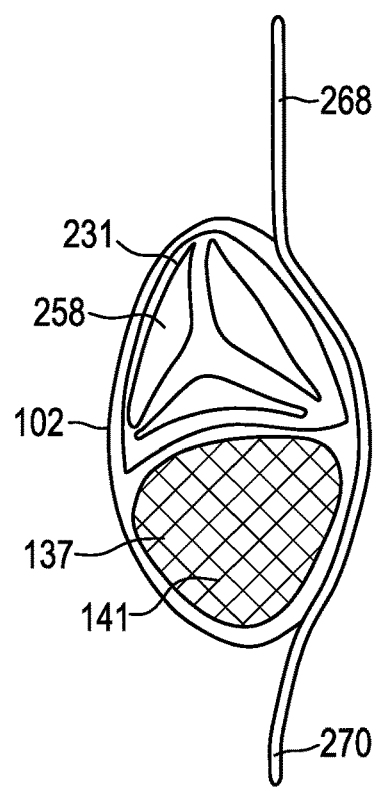

FIG. 43 is an illustration of a BOTTOM view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three sewn leaflet pockets/cusps, an inner spacer frame, and a mesh cover over the spacer frame, according to the invention.

Figure 44:
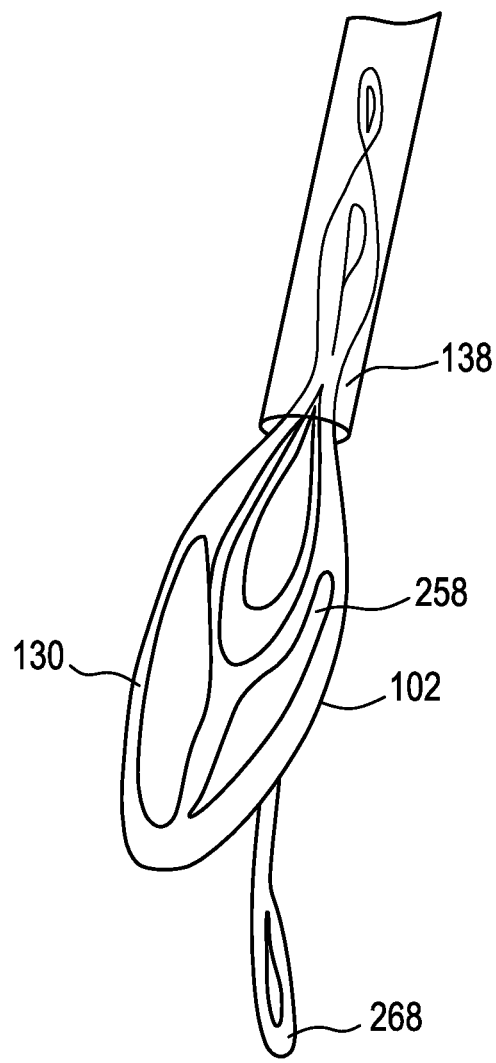

FIG. 44 is an illustration of a TOP view of a valve partially expelled from a delivery catheter, with a distal tab leading the valve (along guide wire not shown) to the deployment location, with distal flow control component beginning to open and showing two of three leaflets opening from a folded, lie-flat configuration with the third leaflet opening from a folded configuration where it is folded back on itself when in the delivery catheter, according to the invention.

Figure 45:
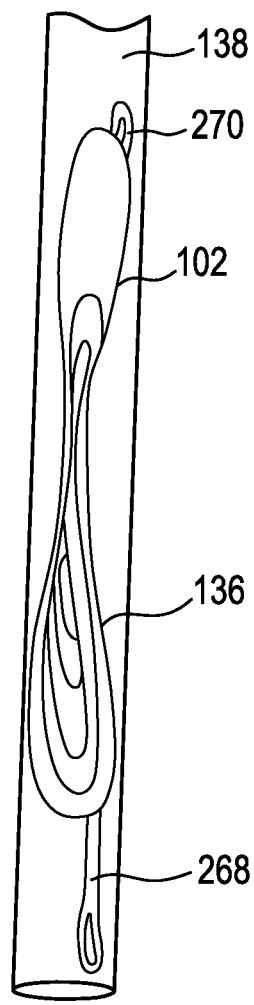

FIG. 45 is an illustration of a TOP view of a valve compressed (orthogonally loaded) within a delivery catheter with a first tab extending forward along a x-axis and a second trailing tab extending backwards along the x-axis, according to the invention.

Figure 46:
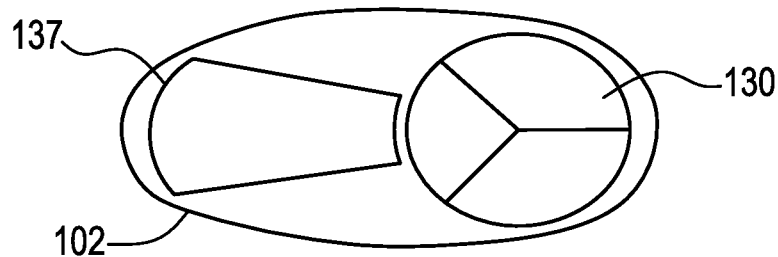

FIG. 46 is an illustration of a TOP view of a valve having an outer frame, an off-center inner flow control component (leaflet in frame) and an irregularly shaped spacer/support frame, according to the invention.

Figure 47:
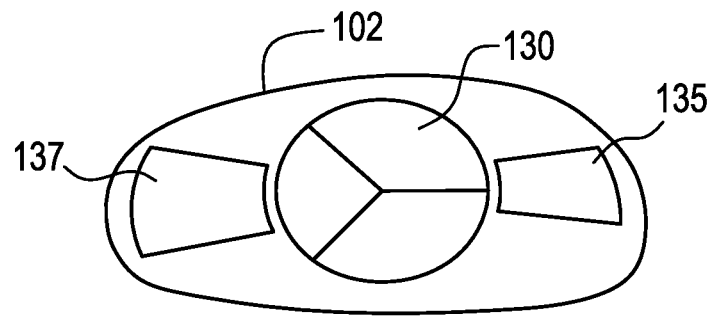

FIG. 47 is an illustration of a TOP view of a valve having an outer frame, a centrally located inner flow control component (leaflet in frame) and a pair of irregularly shaped spacer/support frames on opposing sides of the inner flow control component, according to the invention.

Figure 48:
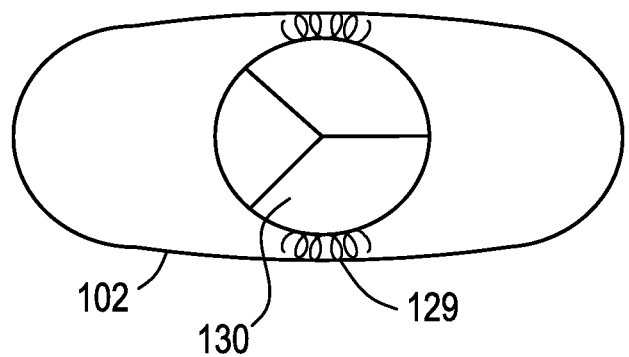

FIG. 48 is an illustration of a TOP view of a valve having an outer frame, and an inner flow control component (leaflet in frame) and a plurality of sewn attachment points where the inner is sewn to the outer, according to the invention.

Figure 49:
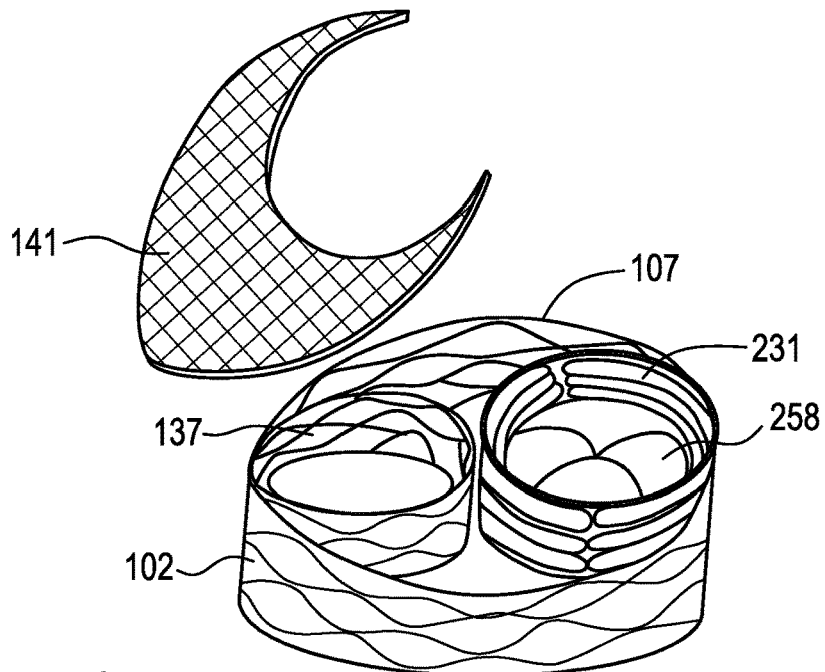

FIG. 49 is an illustration of a TOP PERSPECTIVE view of a valve with a minimal collar or without a collar having mesh spacer frame removed for viewing, an outer cylinder frame with a mesh sidewall cover, a flow control component made of an inner frame and leaflets sewn into the inner, and a cylindrical spacer that is foldable along the same x-axis as the flow control component and the outer frame, and where the spacer is also vertically compressible along the y-axis like the flow control device and the outer frame, according to the invention.

Figure 50:
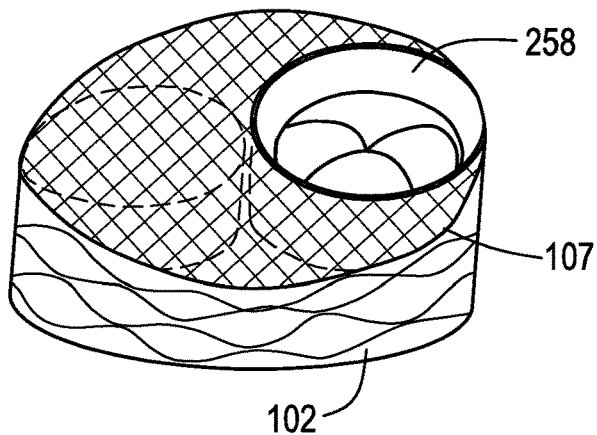

FIG. 50 is an illustration of a TOP PERSPECTIVE view of a valve without a collar having a mesh spacer frame covering the non-leaflet areas and mounted on the top edge of the outer cylinder frame, the outer frame also having a mesh sidewall cover, a flow control component made of an inner frame and leaflets sewn into the inner, and a cylindrical spacer that is foldable along the same x-axis as the flow control component and the outer frame, and where the spacer is also vertically compressible along the y-axis like the flow control device and the outer frame according to the invention.

Figure 51:
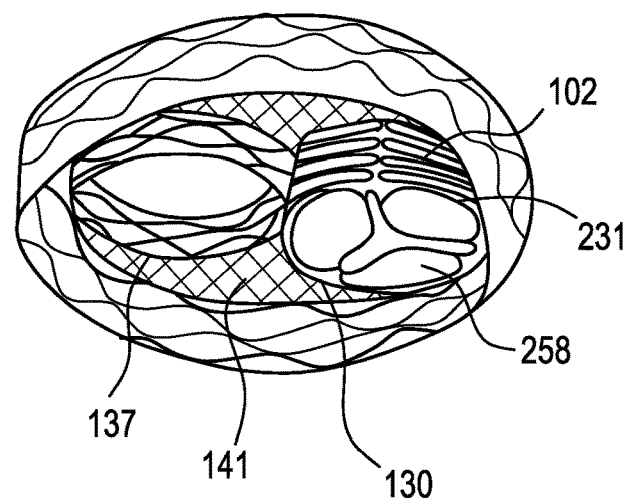

FIG. 51 is an illustration of a BOTTOM PERSPECTIVE view of a valve without a collar having a mesh spacer frame covering the non-leaflet areas and mounted on the top edge of the outer cylinder frame, the outer frame also having a mesh sidewall cover, a flow control component made of an inner frame and leaflets sewn into the inner, and a cylindrical spacer that is foldable along the same x-axis as the flow control component and the outer frame, and where the spacer is also vertically compressible along the y-axis like the flow control device and the outer frame, according to the invention.

Figure 52:
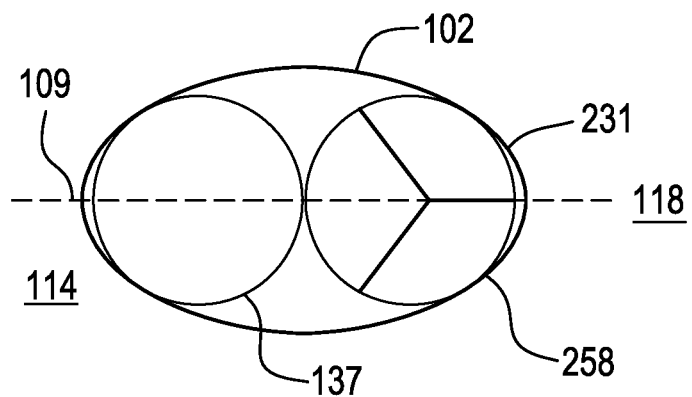

FIG. 52 is an illustration of a TOP view of a valve having an outer frame, an off-center inner flow control component, and an inner spacer frame, all three structures foldable along the same x-axis, according to the invention.

Figure 53:
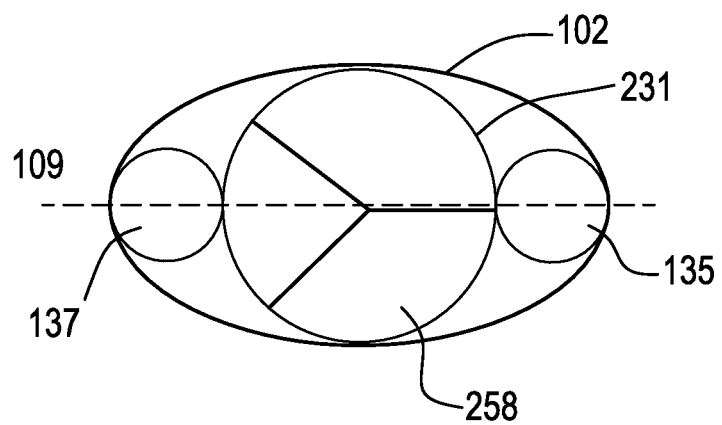

FIG. 53 is an illustration of a TOP view of a valve having an outer frame, a centrally positioned inner flow control component, and a pair of smaller cylindrical inner spacer frames mounted on opposing sides of the inner flow control component to provide support within the interior dimension of the outer frame, all four structures foldable along the same x-axis, according to the invention.

Figure 54:
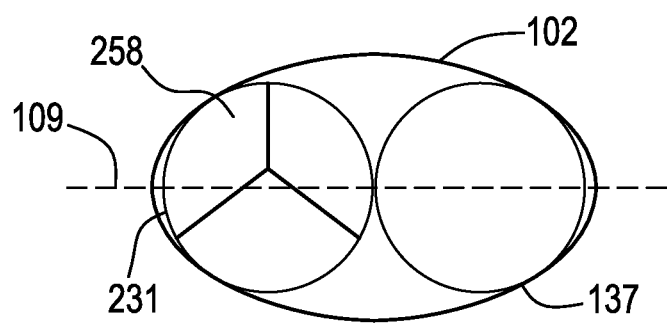

FIG. 54 is an illustration of a TOP view of a valve having an outer frame, a proximally located off-set inner flow control component, and a distal-side inner spacer frame, all three structures foldable along the same x-axis, according to the invention.

Figure 55:
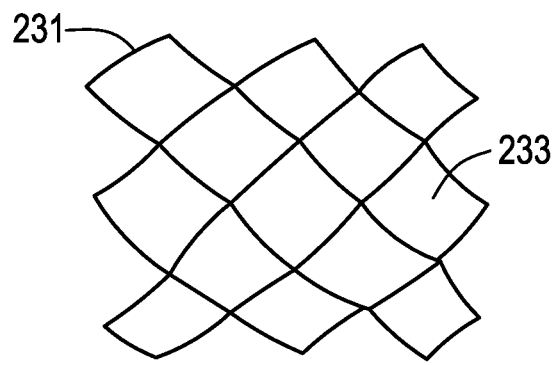

FIG. 55 is an illustration of a SIDE view of a section of wireframe showing that cell geometries can be variable from top to bottom and along the perimeter, with this figure showing a uniform configuration, according to the invention.

Figure 56:
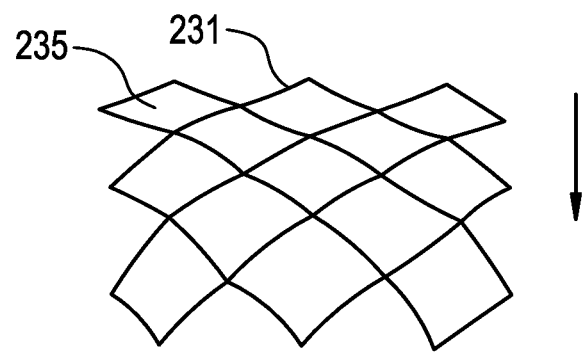

FIG. 56 is an illustration of a SIDE view of a section of wireframe showing that cell geometries can be variable from top to bottom and along the perimeter, with this figure showing a non-uniform configuration with wire cells having increasing cell height from top (least) to bottom (most), according to the invention.

Figure 57:
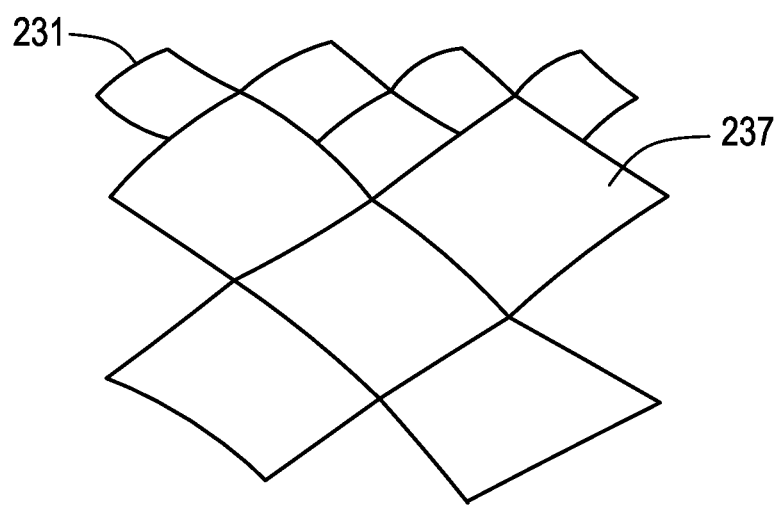

FIG. 57 is an illustration of a SIDE view of a section of wireframe showing that cell geometries can be variable from top to bottom and along the perimeter, with this figure showing a non-uniform configuration with non-uniform cell geometries where the individual cells are varying in size and shape, according to the invention.

Figure 58:
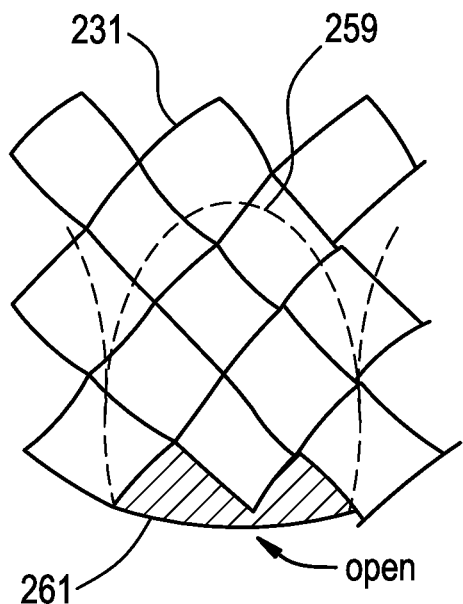

FIG. 58 is an illustration of a SIDE view of a section of wireframe showing that, during an elongation phase of a compressive cycle, e.g. when the valve is in deployed in a heart and subjected to compressive forces, the cell geometries can be tailored to work dynamically with leaflet structure to dampen the forces and to increase coaptation of the prosthetic leaflets, according to the invention.

Figure 59:
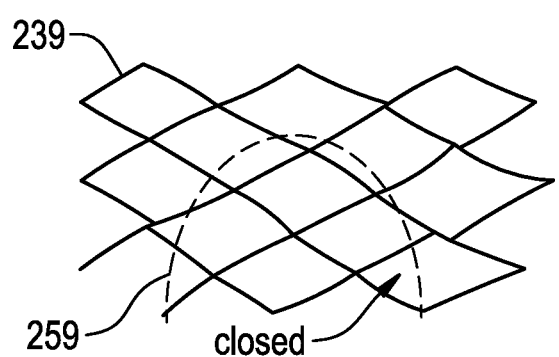

FIG. 59 is an illustration of a SIDE view of a section of wireframe showing that, during a compression phase of a compressive cycle, e.g. when the valve is in deployed in a heart and subjected to compressive forces, the cell geometries can be tailored to work dynamically with leaflet structure to dampen the forces and to increase coaptation of the prosthetic leaflets, according to the invention.

Figure 60:
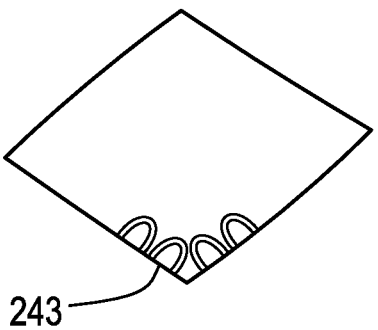

FIG. 60 is an illustration of a SIDE view of a wire frame cell features, such as eyelets at a lower part of the diamond cell, that allow for consistent commissure attachment and valve compressibility, according to the invention.

Figure 61:
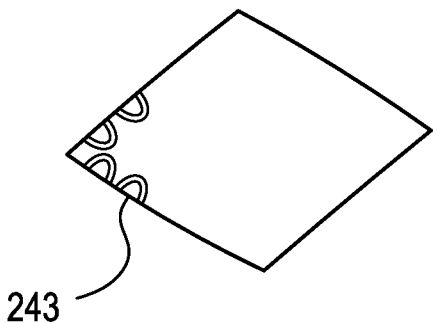

FIG. 61 is an illustration of a SIDE view of a wire frame cell features, such as eyelets at a lateral part of the diamond cell, that allow for consistent commissure attachment and valve compressibility, according to the invention.

Figure 62:
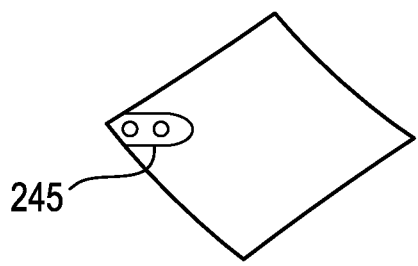

FIG. 62 is an illustration of a SIDE view of a wire frame cell features, such as laser-cut tabbed part of the diamond cell, that allow for consistent commissure attachment and valve compressibility, according to the invention.

Figure 63:
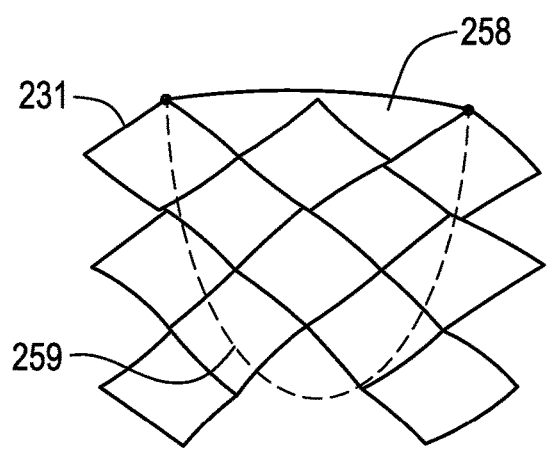

FIG. 63 is an illustration of a SIDE view of a section of wireframe showing that, during an elongation phase of a compressive cycle, e.g. when the valve is in deployed in a heart and subjected to compressive forces, the suture attachment line for mounting the leaflet on the inner frame can be tailored to work dynamically with leaflet structure to reduce damage to the prosthetic leaflets during valve delivery, according to the invention.

Figure 64:
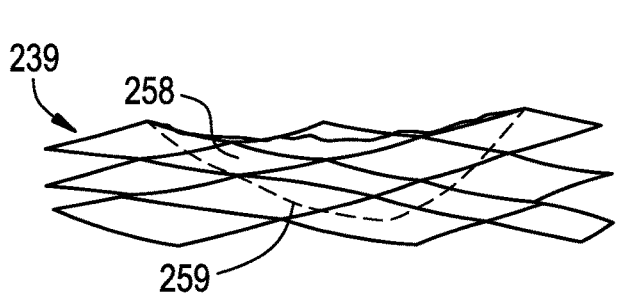

FIG. 64 is an illustration of a SIDE view of a section of wireframe showing that, during a compression phase of a compressive cycle, e.g. when the valve is in deployed in a heart and subjected to compressive forces, the suture attachment line for mounting the leaflet on the inner frame can be tailored to work dynamically with leaflet structure to reduce damage to the prosthetic leaflets during valve delivery, according to the invention.

Figure 65:
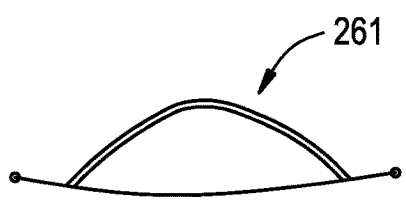

FIG. 65 is an illustration of a TOP view of a leaflet free edge bowing open during expansion, the edge that is not mounted on the inner wire frame, according to the invention.

Figure 66:

FIG. 66 is an illustration of a TOP view of a leaflet free edge laying flat during compression, the edge that is not mounted on the inner wire frame, according to the invention.

Figure 67:
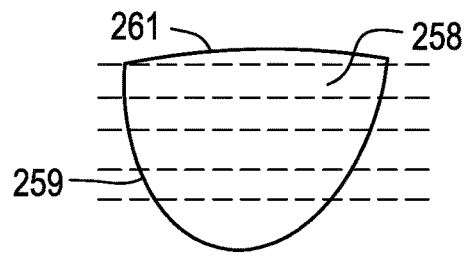

FIG. 67 is an illustration of a TOP view of a leaflet showing that leaflet shape is optimized at multiple planes between the free edge of the leaflet and the sewn, belly portion, and is based on the dynamic foreshortening of the inner wire frame, according to the invention.

Figure 68:
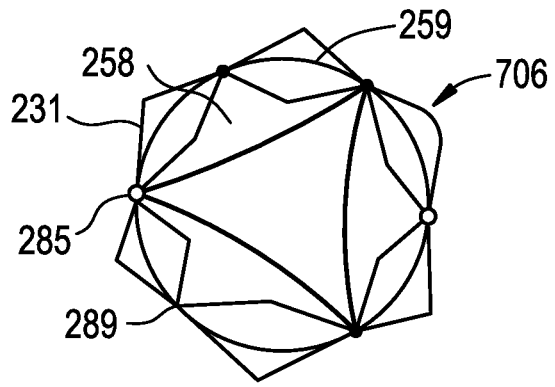

FIG. 68 is an illustration of a TOP view of a flow control component, and shows that the location of the commissures of the prosthetic leaflets are adjustable to allow for optimized leaflet shape and commissure attachment, according to the invention.

Figure 69:
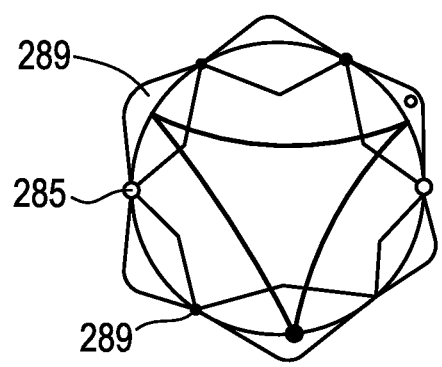

FIG. 69 is another illustration of a TOP view of a flow control component, and shows that the location of the commissures of the prosthetic leaflets are adjustable to allow for optimized leaflet shape and commissure attachment, according to the invention.

Figure 70:
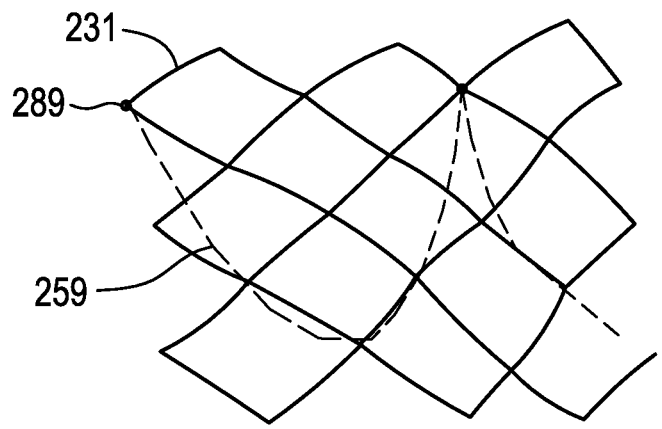

FIG. 70 is an illustration of a SIDE view of a part of a flow control component, and shows that the location of the commissures of the prosthetic leaflets are adjustable to allow for optimized leaflet shape and commissure attachment, according to the invention.

Figure 71:
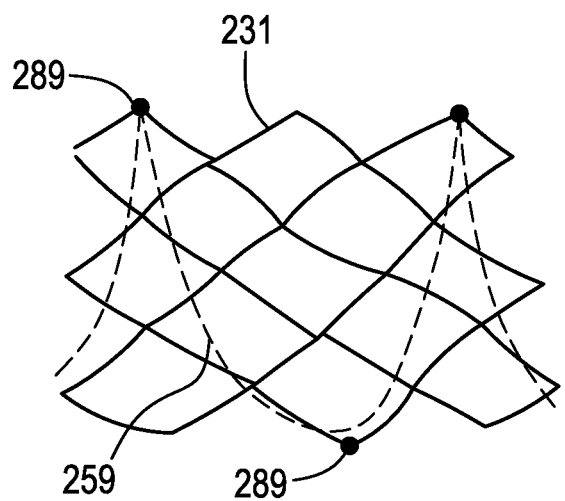

FIG. 71 is another illustration of a SIDE view of a part of a flow control component, and shows that the location of the commissures of the prosthetic leaflets are adjustable to allow for optimized leaflet shape and commissure attachment, according to the invention.

Figure 72:
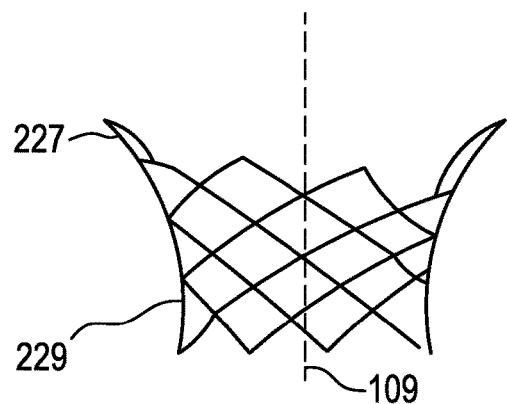

FIG. 72 is an illustration of a SIDE view of a non-cylindrical embodiment of an inner frame having a flared cuff-like portion in the atrial-facing section to allow for better blood flow and smooth transition from the outer frame component, according to the invention.

Figure 73:
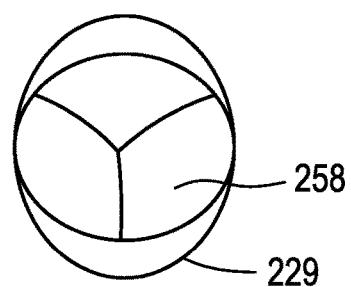

FIG. 73 is an illustration of a TOP view of a non-cylindrical embodiment of an inner frame with leaflet cusps mounted therein, according to the invention.

Figure 74:
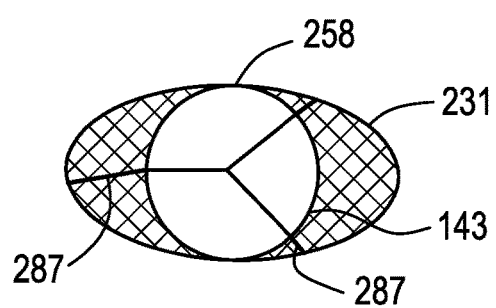

FIG. 74 is an illustration of a TOP view of a non-cylindrical embodiment of an inner frame having an oval shape with the leaflet cusps attached by additional support tabs or structures, and the non-leaflet areas of the interior aspect of the inner frame filled or covered with mesh, according to the invention.

Figure 75:
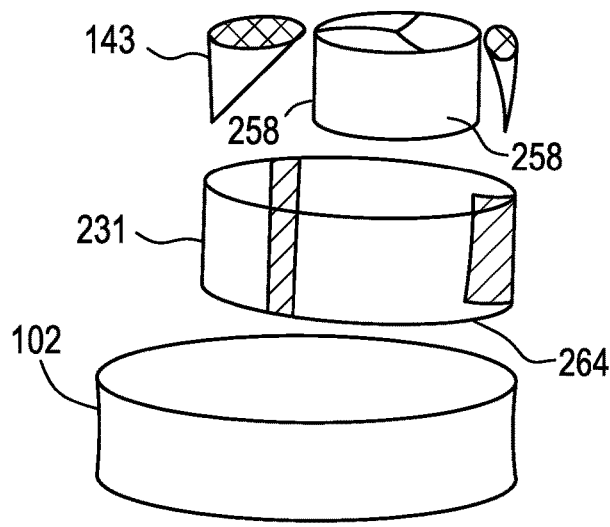

FIG. 75 is an illustration of a SIDE EXPLODED view of a valve having an oval outer frame, with a smaller oval inner frame, with tissue or polymer supports attached to a smaller tissue leaflet component, which is blocked in on opposing sides with mesh spacers, according to the invention.

Figure 76:
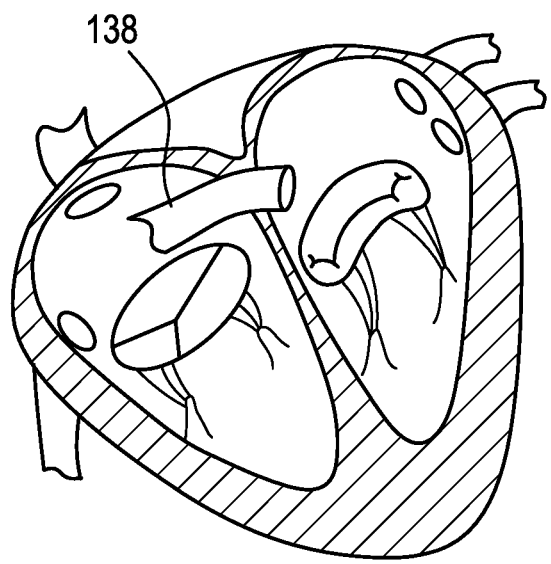

FIG. 76 is an illustration of a SIDE view of a human heart having a trans-septal (trans-femoral/IVC or SVC) delivery catheter crossing from the right atrium to the left atrium for access to the mitral valve, according to the invention.

Figure 77:
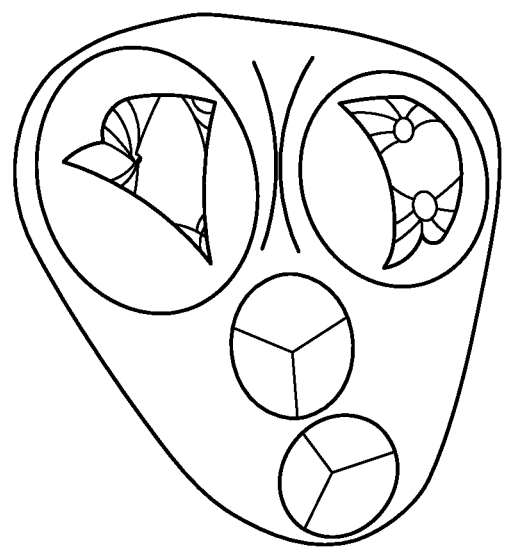

FIG. 77 is an illustration of a CROSS-SECTIONAL view of a human heart showing the relative locations of the mitral valve, the tricuspid valve, the aortic valve, and the pulmonary valve, according to the invention.

Figure 78:
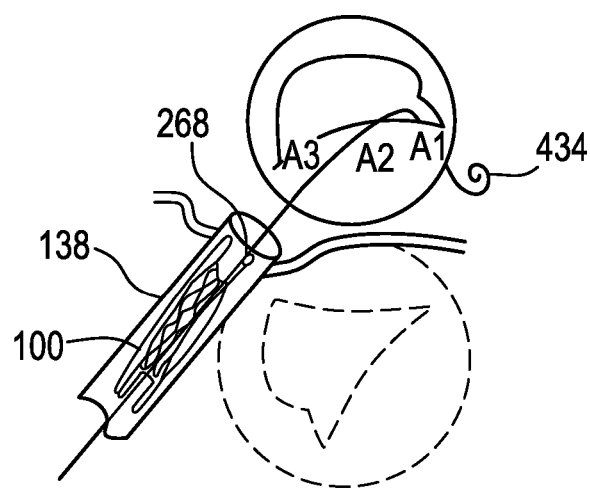

FIG. 78 is an illustration of a TOP view of a mitral valve and shows guide wire directing the replacement valve to the A1 leaflet with the valve in a compressed intra-catheter configuration, according to the invention.

Figure 79:
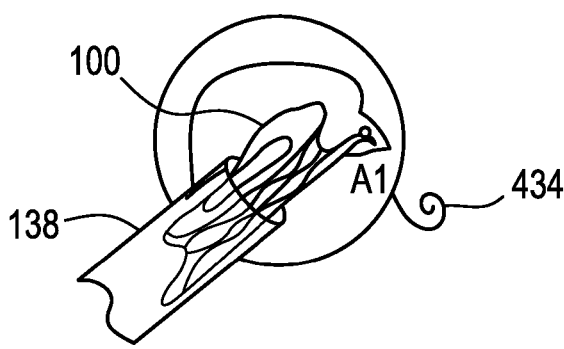

FIG. 79 is an illustration of a TOP view of a mitral valve and prosthetic valve with an overwire tab positioning the valve into the A1 area, and the valve in a partial deployment stage being partially expelled, according to the invention.

Figure 80:
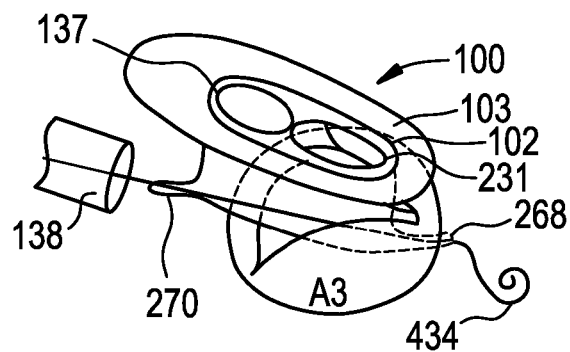

FIG. 80 is an illustration of a TOP PERSPECTIVE view of a prosthetic valve that is fully expelled and positioned temporarily at an upwards angle with a distal anchoring tab in the A1 area, and a proximal A3 anchoring tab above the mitral valve allowing for the new prosthetic valve to engage the blood flow while the native mitral valve continues to operate, just prior to the proximal side being shoe-horned into place with the A3 tab anchoring the proximal side of the valve, for a non-traumatic transition from native valve to prosthetic valve, according to the invention.

Figure 81:
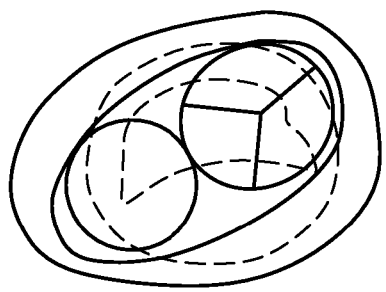

FIG. 81 is an illustration of a TOP view of a prosthetic valve deployed in the native annulus (not visible—in dashed line), according to the invention.

Figure 82:
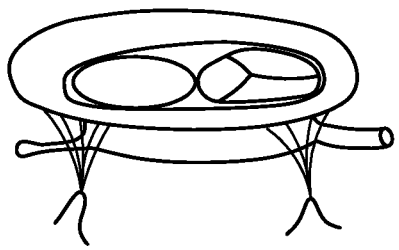

FIG. 82 is an illustration of a SIDE PERSPECTIVE view of a prosthetic valve deployed in the native annulus (not visible), according to the invention.

Figure 83:
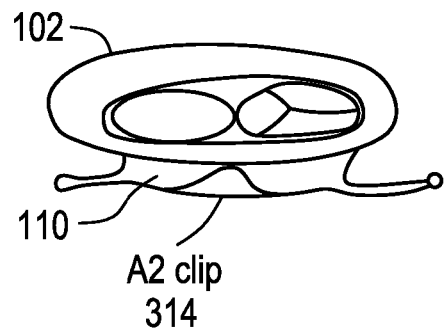

FIG. 83 is an illustration of a SIDE PERSPECTIVE view of an embodiment of a prosthetic valve having an A2 clip integrated into the sidewall of the A2 facing side of the outer frame of the valve, according to the invention.

Figure 84A:
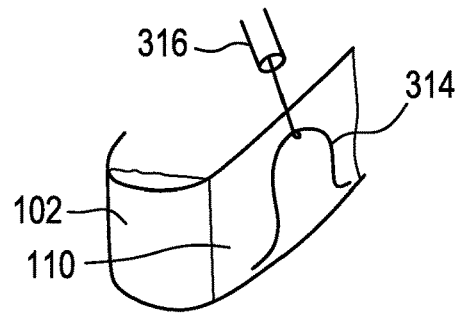
Figure 84B:
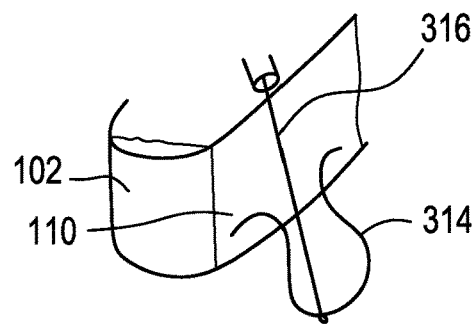
Figure 84C:
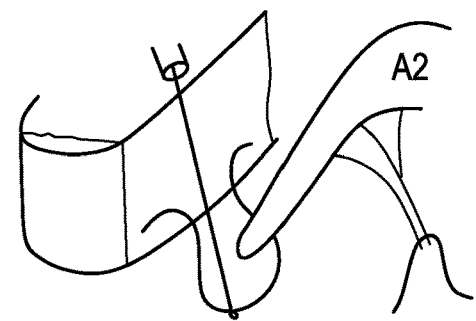
Figure 84D:
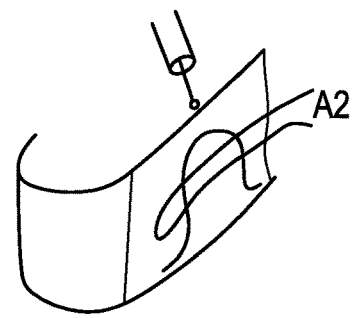

FIG. 84(*a*)-(*d*) is an illustration of a TOP PERSPECTIVE view of a close-up view of a sequence showing an A2 clip being actuated from FIG. 84A a stowed position against the sidewall of the prosthetic valve, to FIG. 84B an open tab-capture position by extending the A2 clip positioning tool, to FIG. 84C an open tab-A2 leaflet in capture range-position, to FIG. 84D a closed position with the A2 leaflet captured between the clip and the outer frame sidewall, according to the invention.

Figure 85:
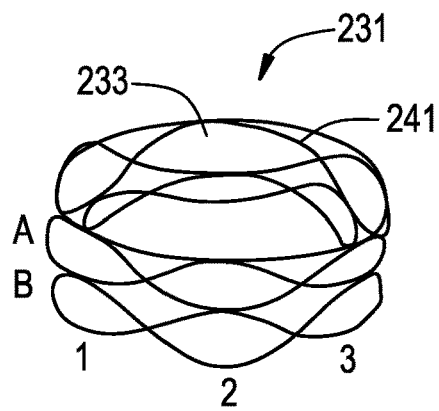

FIG. 85 is an illustration of a SIDE PERSPECTIVE view of an inner wire frame and shows 3 cells per side in two rows for a total of six cells per side and twelve (12) cells total as a preferred embodiment for mounting three (3) leaflet cusps.

Figure 86:
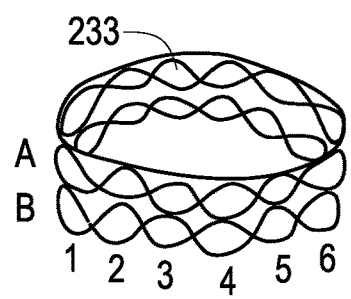

FIG. 86 is an illustration of a SIDE PERSPECTIVE view of an inner wire frame and shows 6 cells per side in two rows for a total of twelve cells per side and twenty-four (24) cells total as a preferred embodiment for mounting three (3) leaflet cusps.

Figure 87:
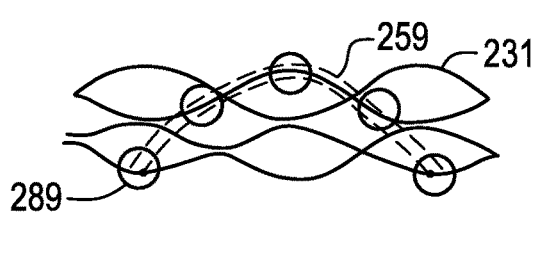

FIG. 87 is an illustration of a SIDE view of a detail of an inner wire frame during diastole (leaflet opening) showing how leaflet tissue is sutured and critical leaflet-frame attachment or connection points are positioned during (lateral) cell expansion.

Figure 88:
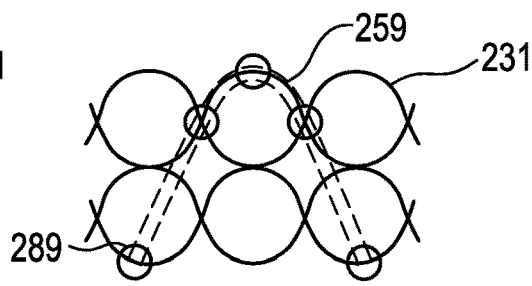

FIG. 88 is an illustration of a SIDE view of a detail of an inner wire frame during systole (leaflet closing) showing how leaflet tissue is sutured and critical leaflet-frame attachment or connection points are positioned during cell contraction, and how the cell geometry reduces leaflet failure at known commissure failure points.

Figure 89:
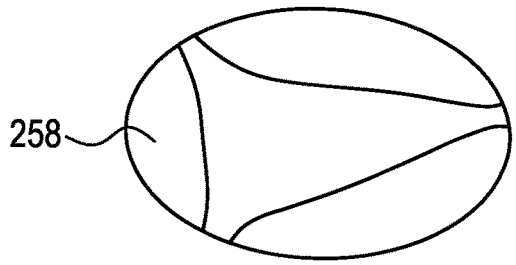

FIG. 89 is an illustration of a TOP view of valve leaflets during diastole.

Figure 90:
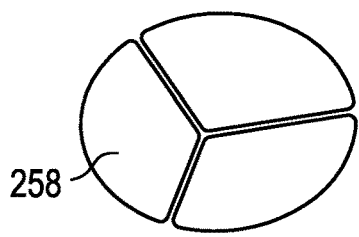

FIG. 90 is an illustration of a TOP view of valve leaflets during systole.

Figure 91:
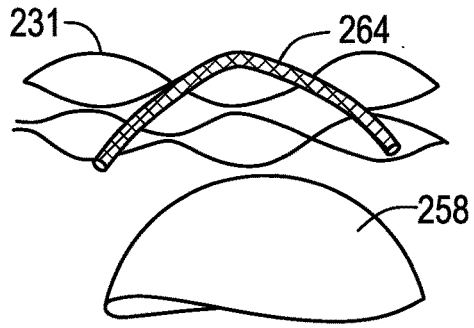

FIG. 91 is an illustration of a SIDE view of a detail of inner wire frame showing how a nitinol or other semi-rigid (semi-flexible) arch can be mounted on the inner wire frame to provide an additional surface for suturing the leaflet cusp to the wire frame.

DETAILED DESCRIPTION OF THE INVENTION

The invention is directed to a dual-tab transcatheter heart valve replacement that is a low profile, orthogonally delivered implantable prosthetic heart valve having an ring-shaped or annular support frame, an inner 2- or 3-panel sleeve, an elongated sub-annular distal anchoring tab extending into the right ventricular outflow tract, an elongated sub-annular proximal anchoring tab extending into the proximal sub-annular space, preferably between the anterior and the posterior leaflets.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side-Delivery or Orthogonal Delivery

In the description and claims herein, the terms "side-delivered", "side-delivery", "orthogonal", "orthogonally delivered" and so forth are used to describe that the valves of the present invention are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Traditional valves have a central cylinder axis that is parallel to the length-wise axis of the delivery catheter and are deployed from the end of the delivery catheter and expanded radially outward from the central annular axis, in a manner akin to pushing a closed spring-loaded umbrella out of a sleeve to make it spring open. However, the valves of the present invention are compressed and delivered in a sideways manner. To begin with the shape of the expanded valve is that of a large diameter shortened cylinder with an extended collar or cuff. The valves are compressed, in one preferred embodiment, where the central axis of the valve is roughly perpendicular to (orthogonal to) the length-wise axis of the delivery catheter. In one preferred embodiment, the valves are compressed vertically, similar to collapsing the height of a cylinder accordion-style from taller to shorter, and the valves are also compressed by folding a front panel against a back panel. In another preferred embodiment, the valves may be compressed by rolling.

Traditional valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, eg. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In preferred embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as Nitinol, the frame is compressible. Preferably, the frame is constructed of a plurality of compressible wire cells having a orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both.

In one preferred embodiment, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

In a preferred embodiment, the horizontal x-axis of the valve is orthogonal to (90 degrees), or substantially orthogonal to (75-105 degrees), or substantially oblique to (45-135 degrees) to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a compressed height (y-axis) and width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. It is contemplated in preferred embodiments that the length of the valve, x-axis, does not require compression since it can extend along the length of the central cylindrical axis of the delivery catheter.

In a preferred embodiment, the valve has an expanded diameter length and width of 25-80 mm, preferably 40-80 mm, and in certain embodiments length and/or width may vary and include lengths of 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In certain preferred embodiments, the valve is centric, or radially symmetrical. In other preferred embodiments, the valve is eccentric, or radially (y-axis) asymmetrical. In some eccentric embodiments, the outer frame may have a D-shape (viewed from the top) so the flat portion can be matched to the mitral annulus near the anterior leaflet.

In certain preferred embodiments, the inner frame holding the leaflet tissue is 25-29 mm in diameter, the outer frame is 50-70 mm in diameter, and the collar structure extends beyond the top edge of the outer frame by 10-30 mm to provide a seal on the atrial floor against perivalvular leaks (PVLs).

The atrial collar is shaped to conform to the native deployment location. In a mitral replacement, the atrial collar will be configured with varying portions to conform to the native valve. In one preferred embodiment, the collar will have a distal and proximal upper collar portion. The distal collar portion can be larger than the proximal upper collar portion to account for annular or subannular geometries.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron (R).

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to [[the]] the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of—, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution.

Ejection fraction is a measurement of the percentage of blood leaving your heart each time it contracts. During each heartbeat pumping cycle, the heart contracts and relaxes. When your heart contracts, it ejects blood from the two pumping chambers (ventricles).

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers—

The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines-Anchors-Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic heart valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316L stainless steel wire frame as base for the drug Tacrolimus and utilizing integrated turbostratic carbofilm as the drug carrier. VESTA sync (MIV Therapeutics) using GenX stainless steel (316L) as base utilizing microporous hydroxyapatite coating as carrier for the drug Sirolimus. YUKON choice (Translumina) used 316L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316L stainless steel coated with polyethylene vinyl acetate (PEVA) and poly-butyl methacrylate (PBMA) for carrying the drug Sirolimus. *Taxus* (Boston Scientific) utilizes 316L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Manufacturing Process

In a preferred embodiment the invention includes a process for manufacturing an orthogonally delivered transcatheter prosthetic heart valve frame, comprising:
(i) using additive or subtractive metal or metal-alloy manufacturing to produce
a self-expanding annular support frame,
wherein the additive metal or metal-alloy manufacturing is 3D printing or direct metal laser sintering (powder melt), and
wherein the subtractive metal or metal-alloy manufacturing is photolithography, laser sintering/cutting, CNC machining, electrical discharge machining.

In another preferred embodiment, there is provided a process for manufacturing an orthogonally delivered transcatheter prosthetic heart valve frame, further comprising the steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Example—Compression Methods

In another preferred embodiment, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.

Drawings

Figure 1:
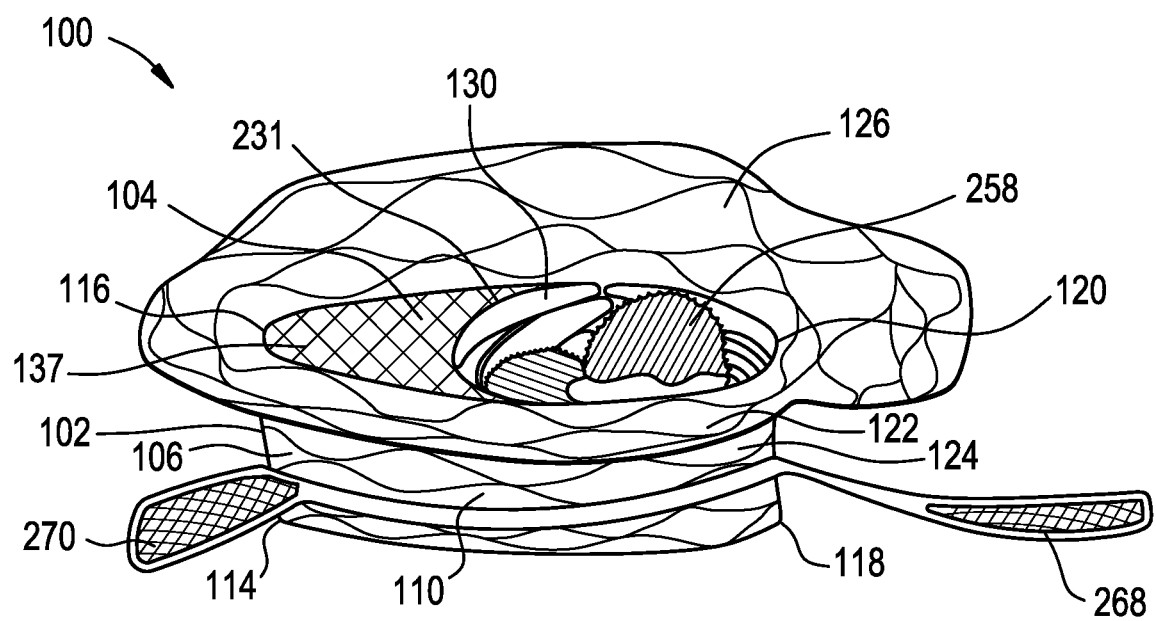
Figure 1:
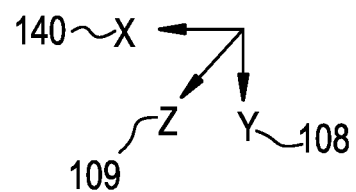

Referring now to the drawings, FIG. 1 is an illustration of a SIDE PERSPECTIVE view of a side delivered transcatheter heart valve 100 with a collapsible flow control component 130 mounted within the annular outer support frame 104, the collapsible (inner) flow control component 130 having leaflet frame 231 with 2-4 flexible leaflets 258 mounted thereon, the leaflet frame 231 foldable along a z-axis 109 from a cylindrical configuration to a flattened cylinder configuration and compressible along a vertical axis 108 (y-axis) to a shortened configuration, and the valve 100 having a superelastic wire loop distal tab 268 and a superelastic wire loop proximal tab 270 according to the invention.

The annular outer support frame 104 is made from a shape-memory material such as Nickel-Titanium alloy, for example NiTiNOL, and is therefore a self-expanding structure starting from a compressed configuration. The annular (outer) support frame 104 has a central (interior) channel 104 and an outer perimeter wall 106 circumscribing a central vertical axis 108, when in an expanded configuration, and said annular outer support frame 104 having a distal side 118 and a proximal side 114.

The flow control component 130 is mounted within the annular outer support frame 104 and is configured to permit blood flow in a first direction, e.g. atrial to ventricular, through an inflow end 132 of the valve 100 and block blood flow in a second direction, opposite the first direction, through an outflow end 134 of the valve 100.

The inner flow control component 130, like the outer annular frame 104, is foldable and compressible. The inner flow control component 130 comprises leaflet frame 231 with 2-4 flexible leaflets 258 mounted on the leaflet frame 231.

The flow control component 130, and thereby the leaflet frame 231, like the outer frame 104, is foldable along a z-axis (front to back) from a cylindrical configuration to a flattened cylinder configuration, where the fold lines are located on a distal side and on a proximal side, taking the leaflet frame 231 from a ring or cylinder shape, and flattening it from a ring to a two-layer band i.e. folded over on itself, or like a cylinder flattened into a rectangle or square joined along two opposing sides. This allows the outer frame 104 and the flow control component 130 to reduce the radius along z-axis until the side walls are in contact or nearly so. This also allows the outer frame 104 and the flow control component 130 to maintain the radius along the horizontal axis, the y-axis, to minimize the number of wire cells, which make up the outer and the inner, that are damaged by forces applied during folding and/or compression necessary for loading into the delivery catheter.

The flow control component 130, leaflet frame 231, and the outer frame 104 are also vertically (y-axis) compressible, reducing the height of the entire valve structure to fit within the inner diameter of a delivery catheter 138 (not shown in this Figure). By folding in the z-axis and vertically compressing in the y-axis, the valve structure is permitted to maintain a very large dimension along the horizontal, or x-axis. For example, a 60 mm or larger diameter valve can be delivered via transcatheter techniques. The length of the long axis of a valve, e.g. 60 mm, since it runs parallel to the central axis of the delivery catheter, is not limited by the large amount of wire frame and cover material necessary for such a large valve. This is not possible with existing center-axis delivery (axial) transcatheter valves. The use of a folded, compressed valve that is orthogonal to the traditional axial-delivery valves permits treatment options not available previously.

FIG. 1 also shows a distal anchoring tab 268 mounted on the distal side 118 of the annular outer support frame 102, and a proximal anchoring tab 270 mounted on the proximal side 114 of the annular outer support frame 102.

In a preferred embodiment, the horizontal x-axis of the valve is at an intersecting angle of between 45-135 degrees to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a height of about 5-60 mm and a diameter of about 25-80 mm.

Figure 2:
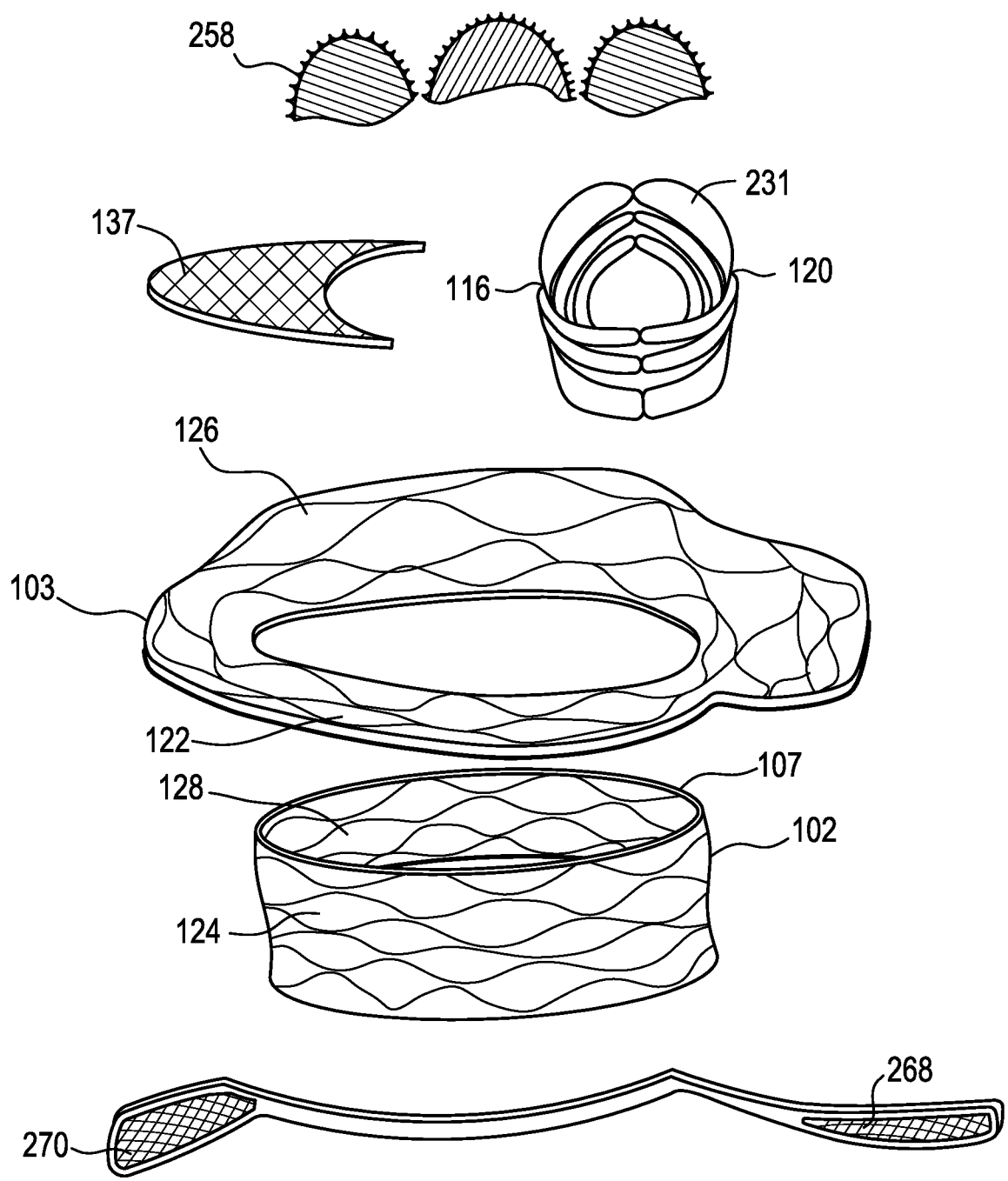

FIG. 2 is an illustration of a SIDE PERSPECTIVE view of an exploded view of an embodiment having three leaflet 258 cusps or pockets mounted within a foldable and compressible inner wire frame 231, with distal fold area 120 and proximal fold area 116, the inner 231 is mounted within an outer wire frame 102 which has a collar component 103 attached circumferentially at a top edge 107 of the outer wire frame 104, a dual tab component having a distal (RVOT) tab 268 and a proximal tab 270, and an optional mesh component of biocompatible material that may be used to cover the spacer element 137, to cover the collar 103, to cover the inner and outer aspect of the outer frame 102, and/or to cover the anchoring tabs 268, and 270, according to the invention.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

Figure 3:
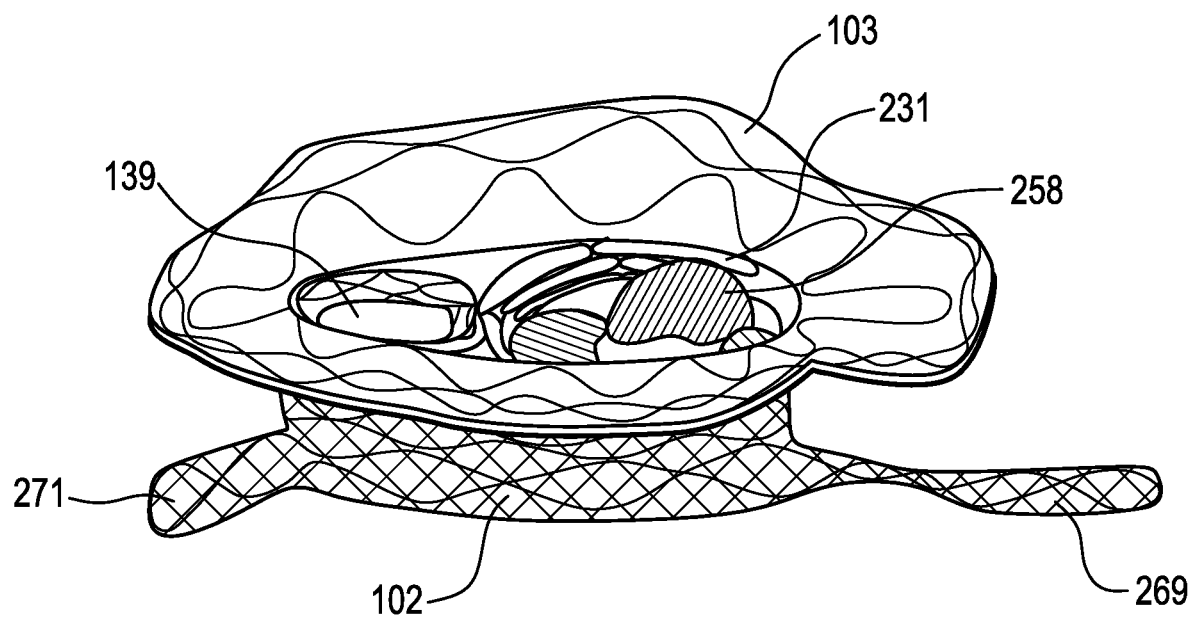

FIG. 3 is an illustration of a SIDE PERSPECTIVE view of a side delivered transcatheter heart valve 100 with a collapsible flow control component 130 mounted within the annular outer support frame 102, the collapsible (inner) flow control component 130 having leaflet frame 231 with 2-4 flexible leaflets 258 mounted thereon. The leaflet frame 231 is foldable along a z-axis from a cylindrical configuration to a flattened cylinder configuration and compressible along a vertical axis (y-axis) to a shortened configuration. The valve 100 also has a superelastic wire loop distal tab 268/269 and a superelastic wire loop proximal tab 270/271 according to the invention.

Figure 4:
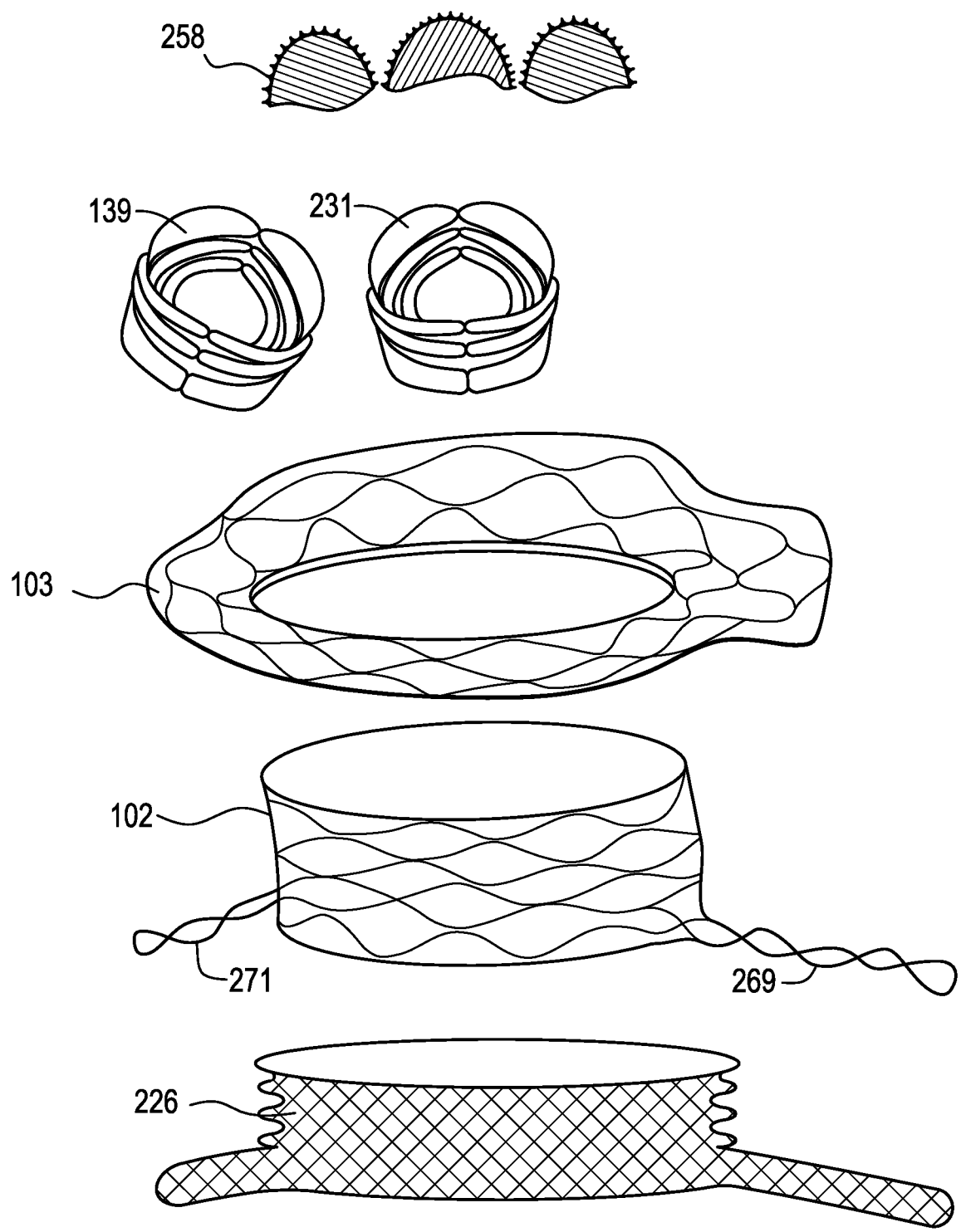

FIG. 4 is an illustration of a SIDE PERSPECTIVE view of an exploded view of an embodiment having three leaflet cusp or pockets 258 mounted within a foldable and compressible inner wire frame 231, the inner 231 is mounted within an outer wire frame 102 which has a collar component 103 attached circumferentially at a top edge 107 of the outer wire frame 102, an uncovered spacer 139, a pair of integrated, independent tab components 269, 270, and a mesh component 226, according to the invention.

Uncovered spacer 139 provides for controlled regurgitation of the valve. The uncovered spacer 139 can be later plugged with a later inserted stent or cover or plug, once regurgitation is no longer needed by the patient.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

Integrated tabs 269 and 271 are unitary construction with the body of the outer frame. The tabs may vary in size and shape. In a preferred embodiment, the RVOT tab, e.g. 269 may be longer to reach into the entry of the pulmonary artery (in the case of a tricuspid replacement). In above preferred embodiment, the shapes of the tabs are configured to confirm to the A1 and A3 commissural areas of the mitral valve.

Figure 5:
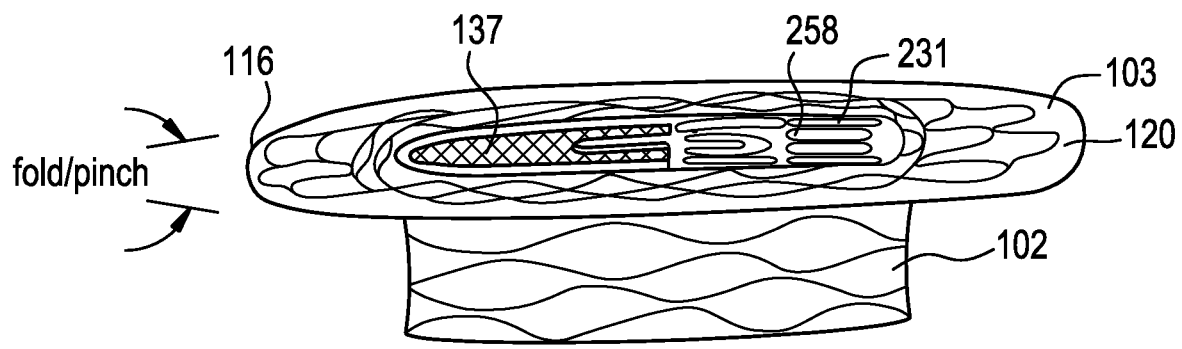
FIG. 5 is an illustration of a SIDE PERSPECTIVE view of a side delivered transcatheter heart valve in a folded configuration along the z-axis (front to back when viewed from the broader side) according to the invention.

FIG. 5 is an illustration of a SIDE PERSPECTIVE view of a side delivered transcatheter heart valve 100 in a folded configuration along the z-axis (front to back when viewed from the broader side) according to the invention. FIG. 5 shows folded (flattened) outer frame 102 with folded/flattened collar 103, hinge points 116, 120. FIG. 5 also shows folded/flattened spacer 137, and leaflets 258 mounted within folded/flattened inner frame 231.

Figure 6:
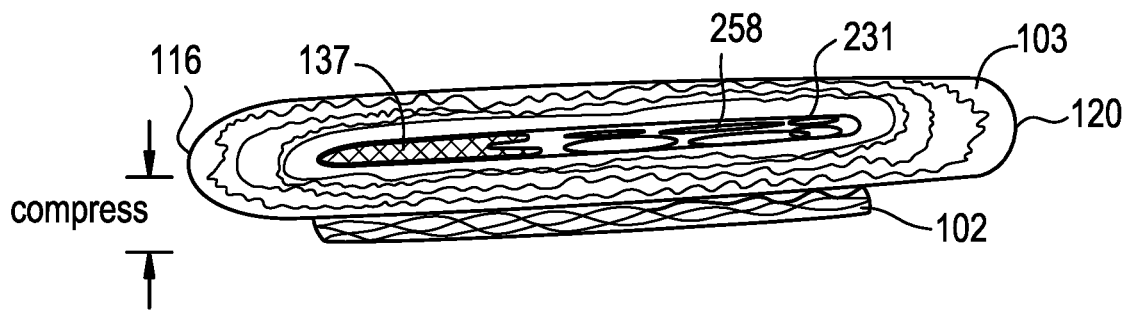
FIG. 6 is an illustration of a SIDE PERSPECTIVE view of a side delivered transcatheter heart valve in a vertically compressed configuration according to the invention.

FIG. 6 is an illustration of a SIDE PERSPECTIVE view of a side delivered transcatheter heart valve 100 in a vertically compressed configuration according to the invention. FIG. 6 shows outer frame 102 folded (z-axis) and compressed vertically (y-axis) with collar 103 folded (z-axis) and compressed (y-axis), along fold line between hinge points 116, 12o. FIG. 6 also shows spacer 137, and leaflets 258 mounted within inner frame 231.

Figure 7:
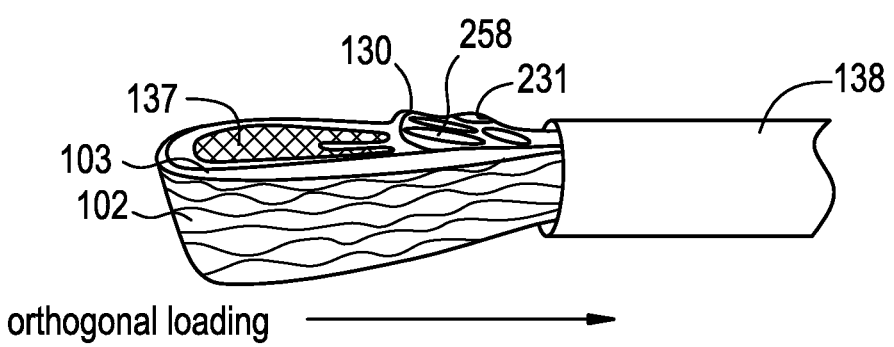
FIG. 7 is an illustration of a SIDE PERSPECTIVE view of a side delivered transcatheter heart valve partially loaded into a delivery catheter, according to the invention.

FIG. 7 is an illustration of a SIDE PERSPECTIVE view of a side delivered transcatheter heart valve 100 partially loaded into a delivery catheter 138, according to the invention. FIG. 7 shows outer frame 102, folded collar 103, spacer 137, and flow control component 130 having leaflets 258 and an inner frame 231.

Figure 8:
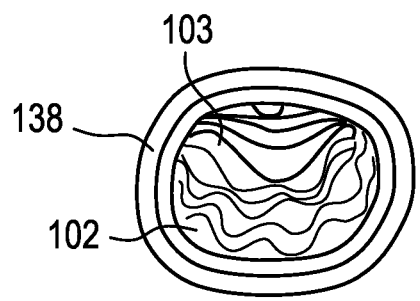
FIG. 8 is an illustration of an END view of a delivery catheter showing the loaded valve, according to the invention.

FIG. 8 is an illustration of an END view of a delivery catheter 138 showing the loaded valve 100 with outer frame 102 and collar 103 visible, according to the invention.

Figure 9:
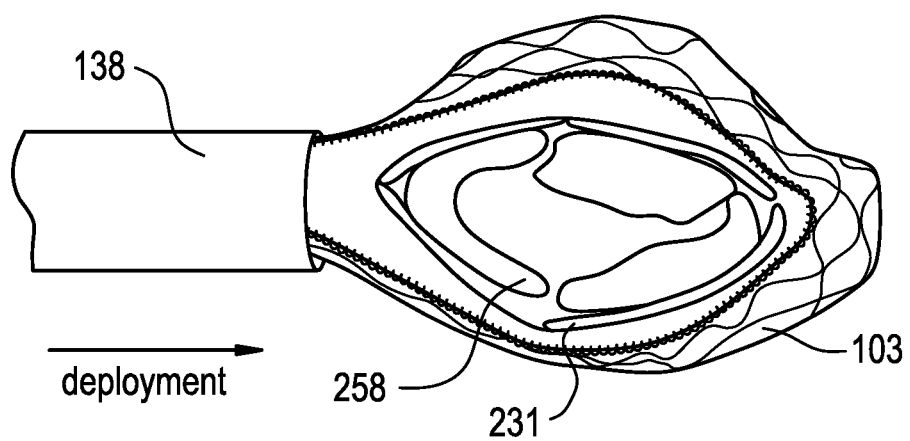
FIG. 9 is an illustration of a TOP view of the folded, compressed valve being expelled from the delivery catheter, in a partial position to allow expansion of the leaflets and the inner frame prior to seating in the native annulus.

FIG. 9 is an illustration of a TOP view of the folded, compressed valve being expelled from the delivery catheter 138, in a partial position to allow expansion of the leaflets 258, collar 103, and the inner frame 231 prior to seating in the native annulus.

Figure 10:
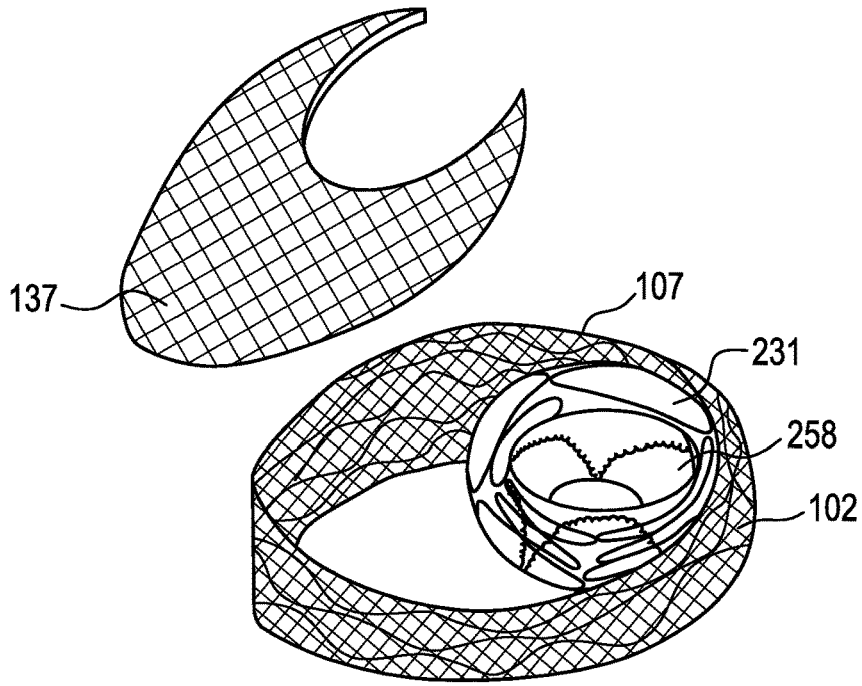
FIG. 10 is an illustration of a TOP PERSPECTIVE view of a valve without a collar having mesh spacer frame removed for viewing, an outer cylinder frame with a mesh sidewall cover, an inner frame, and leaflets sewn into the inner, according to the invention.

FIG. 10 is an illustration of a TOP PERSPECTIVE view of a valve without a collar having mesh spacer frame 137 removed for viewing, an outer cylinder frame 102 with a mesh sidewall cover 226, an inner frame 231, and leaflets 258 sewn into the inner 231, according to the invention.

Figure 11:
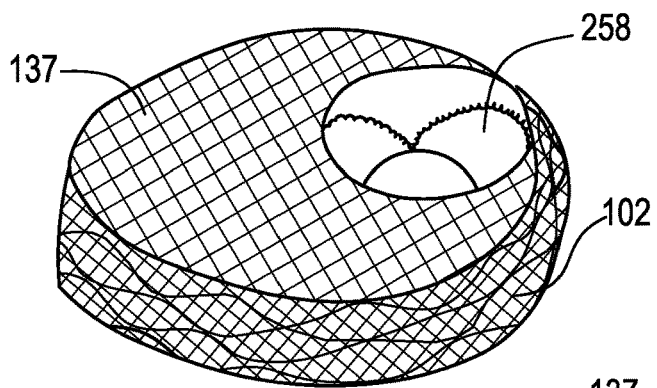
FIG. 11 is an illustration of a TOP PERSPECTIVE view of a valve without a collar having a mesh spacer frame mounted on the top edge of the outer cylinder frame, the outer frame also having a mesh sidewall cover, an inner frame, and leaflets sewn into the inner, according to the invention.

FIG. 11 is an illustration of a TOP PERSPECTIVE view of a valve without a collar having a mesh spacer frame 137 mounted on the top edge 107 of the outer cylinder frame 102, the outer frame 102 also having a mesh sidewall cover 226, an inner frame 231, and leaflets 258 sewn into the inner 231, according to the invention.

Figure 12:
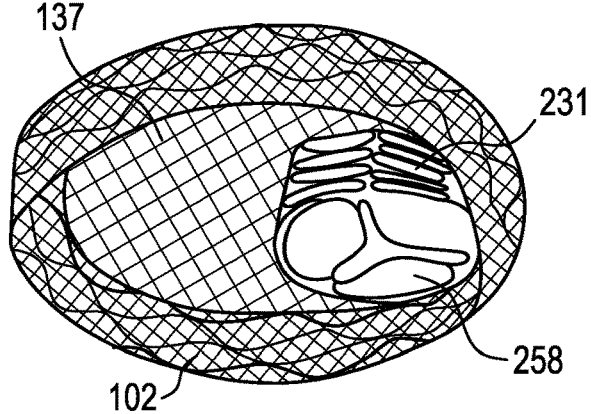
FIG. 12 is an illustration of a BOTTOM PERSPECTIVE view of a valve without a collar having a mesh spacer frame mounted on the top edge of the outer cylinder frame, the outer frame also having a mesh sidewall cover, an inner frame, and leaflets sewn into the inner, according to the invention.

FIG. 12 is an illustration of a BOTTOM PERSPECTIVE view of a valve without a collar having a mesh spacer frame 137 mounted on the top edge 107 of the outer cylinder frame 102, the outer frame 102 also having a mesh sidewall cover 226, an inner frame 231, and leaflets 258 sewn into the inner frame 231, according to the invention.

Figure 13:
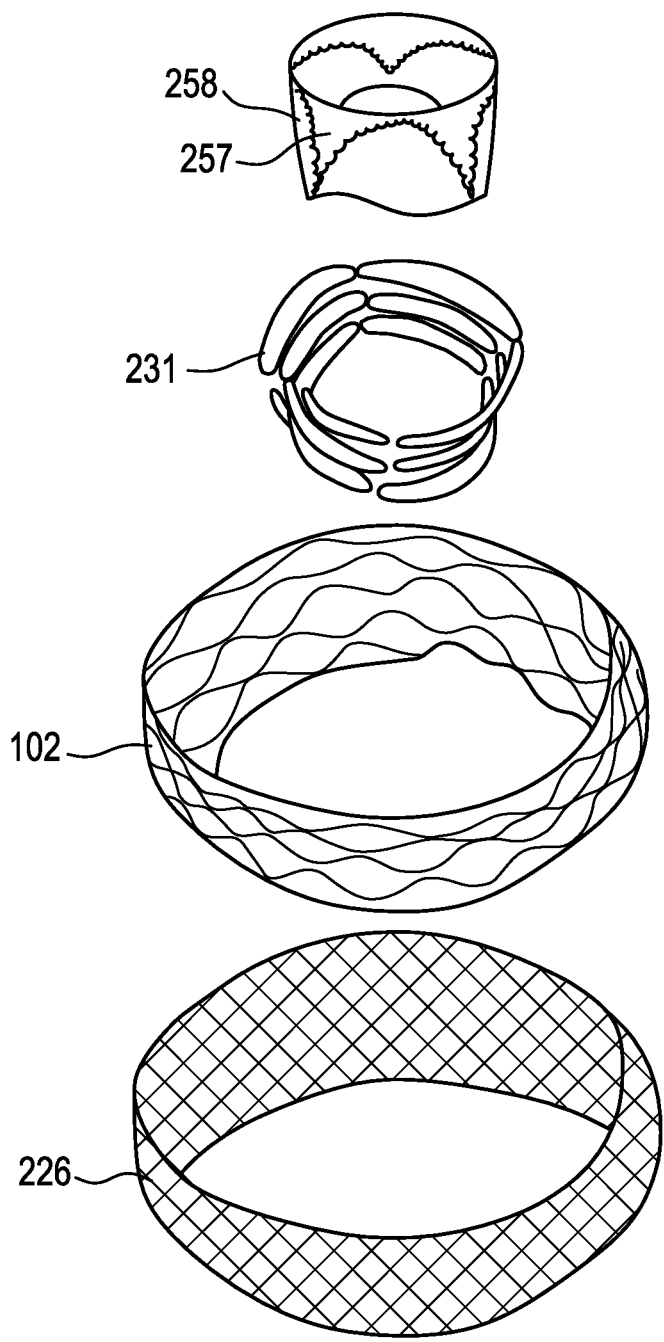
FIG. 13 is an illustration of an EXPLODED view of a valve without a collar having an outer cylinder frame, the outer frame having a mesh sidewall cover, an inner frame, and leaflets sewn into the inner, according to the invention.

FIG. 13 is an illustration of an EXPLODED view of a valve without a collar having an outer cylinder frame 102, the outer frame 102 having a mesh sidewall cover 226, an inner frame 231, and leaflets 258 mounted on a band 257 and sewn into the inner frame 231, according to the invention.

Figure 14:
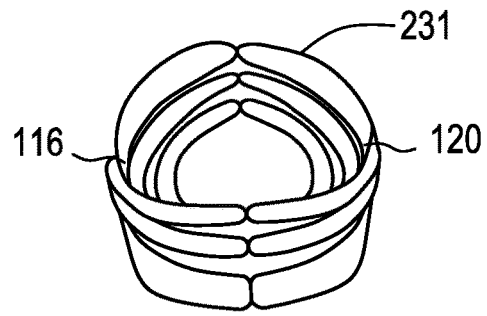
FIG. 14 is an illustration of a TOP PERSPECTIVE view of an inner leaflet frame in a cylinder configuration, shown at the beginning of a process permitting folding and compression of the inner frame, according to the invention.

FIG. 14 is an illustration of a TOP PERSPECTIVE view of an inner leaflet frame 231 in a cylinder configuration, shown at the beginning of a process permitting folding and compression of the inner frame, according to the invention.

Figure 15:
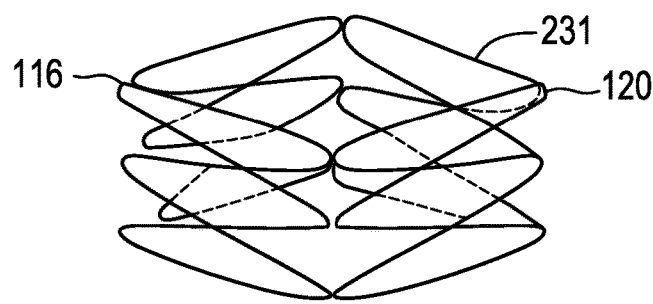
FIG. 15 is an illustration of a TOP PERSPECTIVE view of an inner leaflet frame in a partially folded configuration with the wireframe sidewalls rotating or hinging at their lateral connection points, shown as a partial first step in a process permitting folding and compression of the inner frame, according to the invention.

FIG. 15 is an illustration of a TOP PERSPECTIVE view of an inner leaflet frame 231 in a partially folded configuration with the wireframe sidewalls rotating or hinging at their lateral connection points 116, 120, shown as a partial first step in a process permitting folding and compression of the inner frame, according to the invention.

Figure 16:
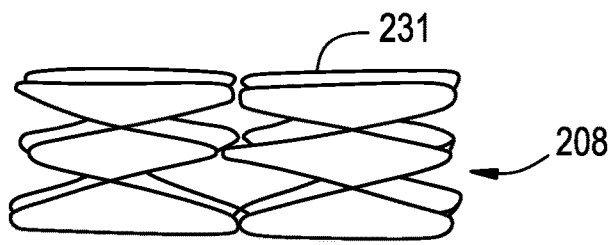
FIG. 16 is an illustration of a SIDE view of an inner leaflet frame in a completely folded configuration with the wireframe sidewalls rotated or hinged at their lateral connection points, shown as a completed first step in a process permitting folding and compression of the inner frame, according to the invention.

FIG. 16 is an illustration of a SIDE view of an inner leaflet frame 231 in a completely folded configuration 208 with the wireframe sidewalls rotated or hinged at their lateral connection points, shown as a completed first step in a process permitting folding and compression of the inner frame 231, according to the invention.

Figure 17:
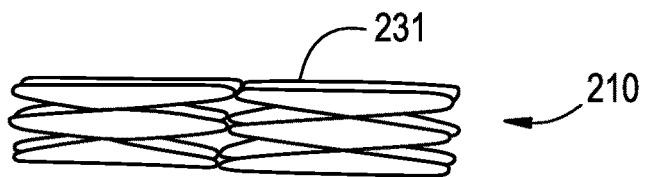
FIG. 17 is an illustration of a SIDE view of an inner leaflet frame in a folded and vertically compressed configuration with the wireframe sidewalls vertically compressed in a pleated or accordion configuration, shown as a second step in a process permitting folding and compression of the inner frame, according to the invention.

FIG. 17 is an illustration of a SIDE view of an inner leaflet frame 231 in a folded and vertically compressed configuration 210 with the wireframe sidewalls vertically compressed in a pleated or accordion configuration, shown as a second step in a process permitting folding and compression of the inner frame, according to the invention.

Figure 18:
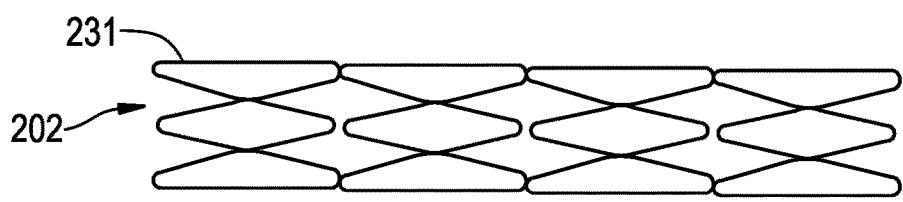
FIG. 18 is an illustration of a SIDE view of an inner leaflet frame as a linear wireframe sheet before further assembly into a cylinder structure, according to the invention.

FIG. 18 is an illustration of a SIDE view of an inner leaflet frame 231 as a linear wireframe sheet 202 before further assembly into a cylinder structure, according to the invention.

Figure 19:
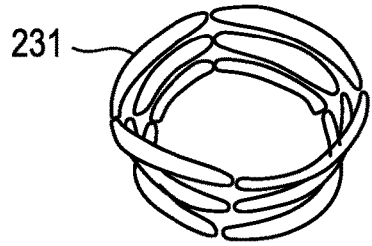
FIG. 19 is an illustration of a SIDE PERSPECTIVE view of an inner leaflet frame in a cylinder or cylinder-like (conical, etc.) configuration, according to the invention.

FIG. 19 is an illustration of a SIDE PERSPECTIVE view of an inner leaflet frame 231 in a cylinder or cylinder-like (conical, etc.) configuration, according to the invention.

Figure 20:
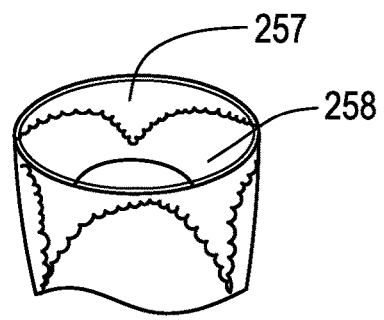
FIG. 20 is an illustration of a SIDE PERSPECTIVE view of a band of pericardial tissue that is configured in a cylinder shape with leaflet pockets sewn into a structural band, according to the invention.

FIG. 20 is an illustration of a SIDE PERSPECTIVE view of a band of pericardial tissue 257 that is configured in a cylinder shape with leaflet pockets 258 sewn into a structural band 257, according to the invention.

Figure 21:
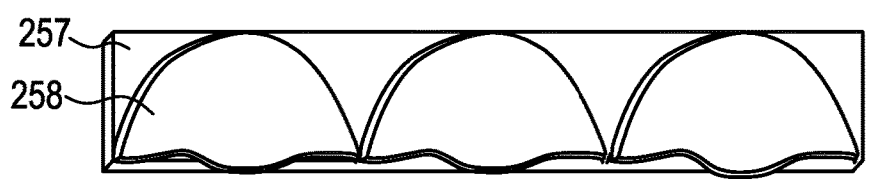
FIG. 21 is an illustration of a SIDE view of a band of pericardial tissue with leaflet pockets sewn into a structural band, before assembly into a cylindrical leaflet component and mounting on an inner frame to form a collapsible (foldable, compressible) flow control component, according to the invention.

FIG. 21 is an illustration of a SIDE view of a band of pericardial tissue 257 with leaflet pockets sewn into a structural band 257, before assembly into a cylindrical leaflet component and mounting on an inner frame to form a collapsible (foldable, compressible) flow control component, according to the invention.

Figure 22:
FIG. 22 is an illustration of a BOTTOM view of a band of pericardial tissue with leaflet pockets sewn into a structural band, before assembly into a cylindrical leaflet component and mounting on an inner frame to form a collapsible (foldable, compressible) flow control component, according to the invention.

FIG. 22 is an illustration of a BOTTOM view of a band of pericardial tissue 257 with leaflet pockets 258 sewn into a structural band 257, before assembly into a cylindrical leaflet component and mounting on an inner frame to form a collapsible (foldable, compressible) flow control component, according to the invention.

Figure 23:
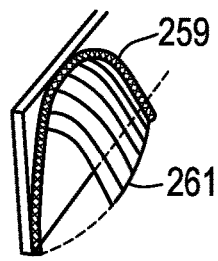
FIG. 23 is an illustration of a SIDE PERSPECTIVE view of part of a band of pericardial tissue with a single leaflet pocket sewn into a structural band, showing an open bottom edge and a sewn, closed top parabolic edge, according to the invention.

FIG. 23 is an illustration of a SIDE PERSPECTIVE view of part of a band of pericardial tissue with a single leaflet pocket sewn into a structural band, showing partial coaptation of a leaflet pocket 258 with open edge 261 extending out and sewn edge 259 as closed top parabolic edge providing attachment, according to the invention.

Figure 24:
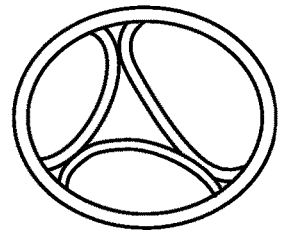
FIG. 24 is an illustration of a BOTTOM view of a cylindrical leaflet component showing partial coaptation of the leaflets to form a closed fluid-seal, according to the invention.

FIG. 24 is an illustration of a BOTTOM view of a cylindrical leaflet component 258 showing complete coaptation, to form a closed fluid-seal, according to the invention.

Figure 25:
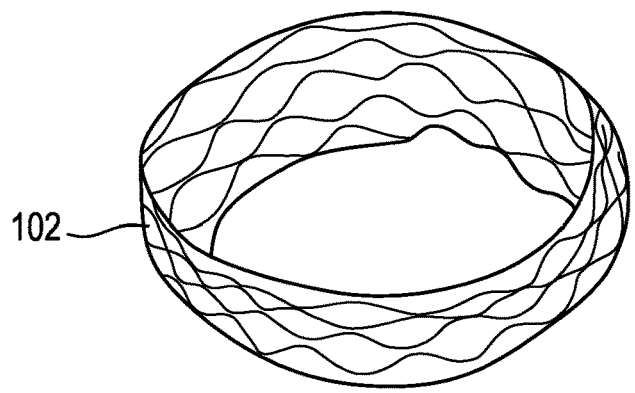
FIG. 25 is an illustration of a TOP PERSPECTIVE view of an outer wire frame in a cylinder configuration, shown at the beginning of a process permitting folding and compression of the OUTER frame, according to the invention.

FIG. 25 is an illustration of a TOP PERSPECTIVE view of an outer wire frame 102 in a cylinder configuration, shown at the beginning of a process permitting folding and compression of the OUTER frame 102, according to the invention.

Figure 26:
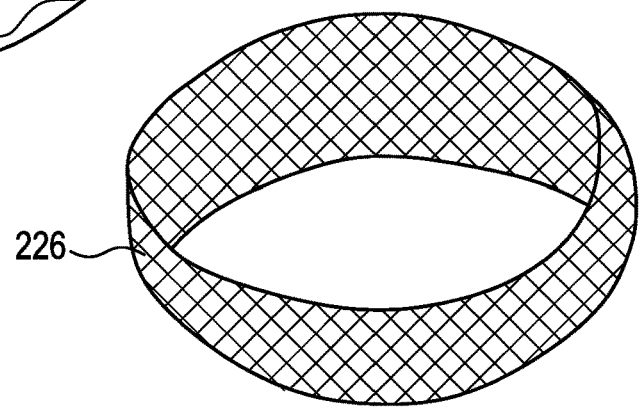
FIG. 26 is an illustration of a TOP PERSPECTIVE view of a mesh cover for the outer frame, according to the invention.

FIG. 26 is an illustration of a TOP PERSPECTIVE view of a mesh cover 226 for the outer frame 102, according to the invention.

Figure 27:
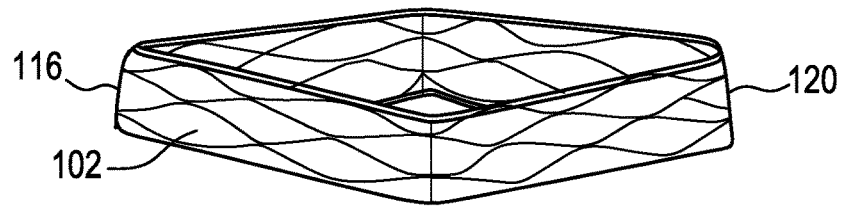
FIG. 27 is an illustration of a TOP PERSPECTIVE view of an outer frame in a partially folded configuration with the wireframe sidewalls rotating or hinging at their lateral connection points, shown as a partial first step in a process permitting folding and compression of the inner frame, according to the invention.

FIG. 27 is an illustration of a TOP PERSPECTIVE view of a partially folded configuration of the outer wireframe 102 with sidewalls rotating or hinging at their lateral connection points 116, 120, shown as a partial first step in a process permitting folding and compression of the outer frame 102, according to the invention.

Figure 28:
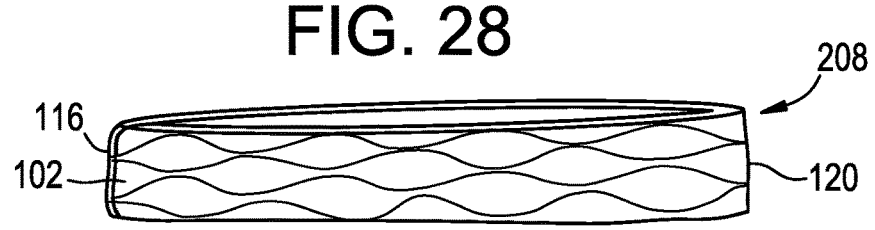
FIG. 28 is an illustration of a SIDE view of an outer frame in a completely folded flat configuration with the wireframe sidewalls rotated or hinged at their lateral connection points, shown as a completed first step in a process permitting folding and compression of the inner frame, according to the invention.

FIG. 28 is an illustration of a SIDE view of an outer frame 102 in a completely folded flat configuration 208 with the wireframe sidewalls rotated or hinged at their lateral connection points 116, 120, shown as a completed first step in a process permitting folding and compression of the outer frame 102, according to the invention.

Figure 29:
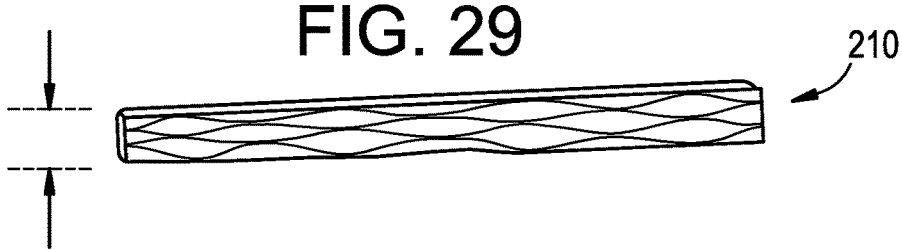
FIG. 29 is an illustration of a SIDE view of an outer frame in a folded and vertically compressed configuration with the wireframe sidewalls vertically compressed in a pleated or accordion configuration, shown as a second step in a process permitting folding and compression of the inner frame, according to the invention.

FIG. 29 is an illustration of a SIDE view of an outer frame 102 in a folded and vertically compressed configuration 210 with the wireframe sidewalls vertically compressed in a pleated or accordion configuration, shown as a second step in a process permitting folding and compression of the outer frame 102, according to the invention.

Figure 30:
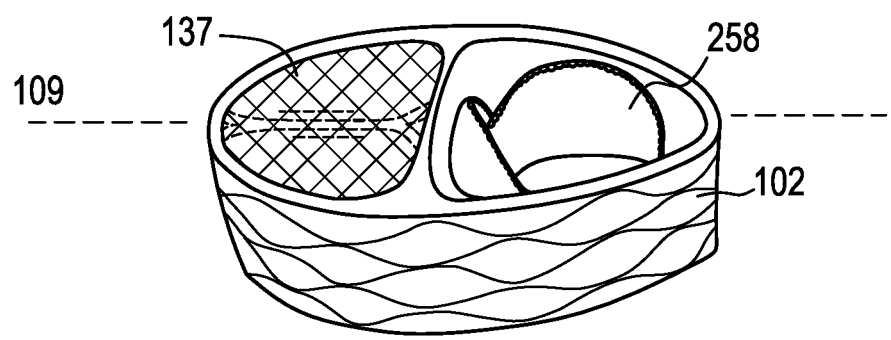
FIG. 30 is an illustration of a TOP PERSPECTIVE view of an assembled valve with an outer frame, a flow control component having an inner leaflet frame and three sewn leaflet pockets/cusps, an inner spacer frame, and a mesh cover over the spacer frame, fold-line is shown as a dashed line on the mesh cover, according to the invention.

FIG. 30 is an illustration of a TOP PERSPECTIVE view of an assembled valve with an outer frame 102, a flow control component 130 having an inner leaflet frame 231 and three sewn leaflet pockets/cusps 258, an inner spacer frame 137, and a mesh cover 141 over the spacer frame, fold-line 109 is shown as a dashed line, according to the invention.

FIG. 31 is an illustration of a TOP PERSPECTIVE view of an assembled valve with an outer frame 102, a first sub-annular anchoring/positioning tab 268 mounted on the outer frame 102 adjacent the flow control component 130, a second sub-annular anchoring/positioning tab 270 mounted on the outer frame in a different location, a flow control component 130 having an inner leaflet frame 231 and three sewn leaflet pockets/cusps 258, an inner spacer frame 137, and a mesh cover 141 over the spacer frame, fold-line 109 is shown as a dashed line and crosses the mesh cover, according to the invention.

FIG. 32 is an illustration of a BOTTOM PERSPECTIVE view of an assembled valve with an outer frame 102, a first sub-annular anchoring/positioning tab 268 mounted on the outer frame 102 adjacent the flow control component 130, a second sub-annular anchoring/positioning tab 270 mounted on the outer frame 102 in a different location, a flow control component 130 having an inner leaflet frame 231 and three sewn leaflet pockets/cusps 258, an inner spacer frame 137 and a mesh cover 141 over the spacer frame, fold-line 109 is shown as a dashed line, and hemodynamic washing cavity is shown under the covered inner spacer frame, according to the invention.

FIG. 33 is an illustration of a TOP view of an assembled valve with an outer frame 102, a flow control component 130 having an inner leaflet frame 231 and three sewn leaflet pockets/cusps 258, an inner spacer frame 137, and a mesh cover 141 over the spacer frame, according to the invention.

FIG. 34 is an illustration of a TOP view of an assembled valve with an outer frame 102, a first sub-annular anchoring/positioning tab 268 mounted on the outer frame 102 adjacent the flow control component 130, a second sub-annular anchoring/positioning tab 270 mounted on the outer frame 102 in a different location, a flow control component 130 having an inner leaflet frame 231 and three sewn leaflet pockets/cusps 258, an inner spacer frame 137, and a mesh cover 141 over the spacer frame, according to the invention.

FIG. 35 is an illustration of a front PLAN view of a non-tabbed valve with foldable and compressible wireframe construction 102 visible, according to the invention.

FIG. 36 is an illustration of a front PLAN view of a tabbed valve with sub-annular anchoring and/or positioning tab 268 extending towards the viewer, and with foldable and compressible wireframe construction 102 visible, according to the invention.

FIG. 37 is an illustration of a front anterior PLAN view of a non-tabbed valve with foldable and compressible wireframe construction 102 visible, according to the invention.

FIG. 38 is an illustration of a front anterior PLAN view of a tabbed valve with sub-annular anchoring and/or positioning tab 268 extending towards the viewer, and second sub-annular tab extending away 270, and with foldable and compressible wireframe construction 102 visible, according to the invention.

FIG. 39 is an illustration of a front septal PLAN view of a non-tabbed valve with foldable and compressible wireframe 102 construction visible, and with inner flow control component 130 in a distal position and mesh-covered inner spacer frame 137 in a proximal location, according to the invention.

FIG. 40 is an illustration of a front septal PLAN view of a tabbed valve with sub-annular RVOT anchoring and/or positioning tab 268 extending left, and second sub-annular proximal tab extending right 270, and with foldable and compressible wireframe construction 102 visible, and with inner flow control component 130 in a distal position and mesh-covered inner spacer frame 137 in a proximal location, according to the invention.

FIG. 41 is an illustration of a side septal PLAN view of a tabbed valve 100 with sub-annular anchoring and/or positioning tab 268 extending towards a distal side, and second sub-annular tab 270 extending away to a proximal side, and with foldable and compressible wireframe construction visible, including inner frame 231, leaflets 258, and spacer 137, according to the invention.

FIG. 42 is an illustration of a TOP view of an assembled valve with an outer frame 102, a first sub-annular anchoring/positioning tab 268 mounted on the outer frame 102 adjacent the flow control component 130, a second sub-annular anchoring/positioning tab 270 mounted on the outer frame 102 in a different location, a flow control component 130 having an inner leaflet frame 231 and three sewn leaflet pockets/cusps 258, an inner spacer frame 137, and a mesh cover 141 over the spacer frame, according to the invention.

FIG. 43 is an illustration of a BOTTOM view of an assembled valve with an outer frame 102, a first sub-annular anchoring/positioning tab 268 mounted on the outer frame 102 adjacent the flow control component 130, a second sub-annular anchoring/positioning tab 270 mounted on the outer frame 102 in a different location, a flow control component 130 having an inner leaflet frame 231 and three sewn leaflet pockets/cusps 258, an inner spacer frame 137, and a mesh cover 141 over the spacer frame 137, according to the invention.

FIG. 44 is an illustration of a TOP view of a valve partially expelled from a delivery catheter 138, with a distal tab 268 leading the valve (along guide wire not shown) to the deployment location, with distal flow control component 130 beginning to open and showing two of three leaflets 258 opening from a folded, lie-flat configuration with the third leaflet opening from a folded configuration where it is folded back on itself when in the delivery catheter 138.

FIG. 45 is an illustration of a TOP view of a valve compressed 136 (orthogonally loaded) within a delivery catheter 138 with an outer frame 102 having a first tab 268 extending forward along a x-axis and a second trailing tab 270 extending backwards along the x-axis.

FIG. 46 is an illustration of a TOP view of a valve having an outer frame 102, an off-center inner flow control component 130 (leaflet in frame) and an irregularly shaped spacer/support frame 137, according to the invention.

FIG. 47 is an illustration of a TOP view of a valve having an outer frame 102, a centrally located inner flow control component 130 (leaflet in frame) and a pair of irregularly shaped spacer/support frames 135, 137 on opposing sides of the inner flow control component 130, according to the invention.

FIG. 48 is an illustration of a TOP view of a valve having an outer frame 102, and an inner flow control component 130 (leaflet in frame) and a plurality of sewn attachment points 129 where the inner 130 is sewn to the outer 102, according to the invention.

FIG. 49 is an illustration of a TOP PERSPECTIVE view of a valve with a minimal collar or without a collar having mesh spacer frame 141 removed for viewing, an outer cylinder frame 102 with a mesh sidewall cover, a flow control component 130 made of an inner frame 231 and leaflets 258 sewn into the inner 231, and a cylindrical spacer 137 that is foldable along the same x-axis 109 as the flow control component 130 and the outer frame 102, and where the spacer 137 is also vertically compressible along the y-axis like the flow control device 130 and the outer frame 102, according to the invention.

FIG. 50 is an illustration of a TOP PERSPECTIVE view of a valve without a collar having a mesh spacer frame 141 covering the non-leaflet areas and mounted on the top edge 107 of the outer cylinder frame 102, the outer frame 102 also having a mesh sidewall cover, a flow control component 130 made of an inner frame 231 and leaflets 258 sewn into the inner 231, and a cylindrical spacer 137 that is foldable along the same x-axis as the flow control component 130 and the outer frame 102, and where the spacer is also vertically compressible along the y-axis like the flow control device and the outer frame, according to the invention.

FIG. 51 is an illustration of a BOTTOM PERSPECTIVE view of a valve without a collar having a mesh spacer frame 141 covering the non-leaflet areas and mounted on the top edge of the outer cylinder frame 102, the outer frame 102 also having a mesh sidewall cover, a flow control component 130 made of an inner frame 231 and leaflets 258 sewn into the inner 231, and a cylindrical spacer 137 that is foldable along the same x-axis as the flow control component 130 and the outer frame 102, and where the spacer 137 is also vertically compressible along the y-axis like the flow control device 130 and the outer frame 102, according to the invention.

FIG. 52 is an illustration of a TOP view of a valve having an outer frame 102, an off-center inner flow control component 130 having frame 231 and leaflets 258, and an inner spacer frame 137, all three structures foldable along the same x-axis 109, according to the invention.

FIG. 53 is an illustration of a TOP view of a valve having an outer frame 102, a centrally positioned inner flow control component 130 having frame 231 and leaflets 258, and a pair of smaller cylindrical inner spacer frames 135, 137 mounted on opposing sides of the inner flow control component 231 to provide support within the interior dimension of the outer frame 102, all four structures foldable along the same x-axis 109, according to the invention.

FIG. 54 is an illustration of a TOP view of a valve having an outer frame 102, a proximally located off-set inner flow control component 130 having frame 231 and leaflets 258, and a distal-side inner spacer frame 137, all three structures foldable along the same x-axis 109, according to the invention.

FIG. 55 is an illustration of a SIDE view of a section of wireframe 231 showing that cell geometries can be variable from top to bottom and along the perimeter, with this figure showing a uniform configuration 233, according to the invention.

FIG. 56 is an illustration of a SIDE view of a section of wireframe 231 showing that cell geometries can be variable from top to bottom and along the perimeter, with this figure showing a non-uniform (height) configuration 235 with wire cells having increasing cell height from top (least) to bottom (most), according to the invention.

FIG. 57 is an illustration of a SIDE view of a section of wireframe 231 showing that cell geometries 237 can be variable from top to bottom and along the perimeter, with this figure showing a non-uniform configuration with non-uniform cell geometries 237 where the individual cells are varying in size and shape, according to the invention.

FIG. 58 is an illustration of a SIDE view of a section of wireframe 231 showing that, during an elongation phase of a compressive cycle, e.g. when the valve is in deployed in a heart and subjected to compressive forces, the cell geometries can be tailored to work dynamically with leaflet structure along the sewn edge 259 to dampen the forces and to increase coaptation of the prosthetic leaflets along the open edge 261, according to the invention.

FIG. 59 is an illustration of a SIDE view of a section of compressed wireframe 239 showing that, during a compression phase of a compressive cycle, e.g. when the valve is in deployed in a heart and subjected to compressive forces, the cell geometries can be tailored to work dynamically with leaflet structure along the sewn edge 259 to dampen the forces and to increase coaptation of the prosthetic leaflets, according to the invention.

FIG. 60 is an illustration of a SIDE view of a wire frame cell features, such as eyelets 243 at a lower part of the diamond cell, that allow for consistent commissure attachment and valve compressibility, according to the invention.

FIG. 61 is an illustration of a SIDE view of a wire frame cell features, such as eyelets 243 at a lateral part of the diamond cell, that allow for consistent commissure attachment and valve compressibility, according to the invention.

FIG. 62 is an illustration of a SIDE view of a wire frame cell features, such as laser-cut tabbed part 245 of the diamond cell, that allow for consistent commissure attachment and valve compressibility, according to the invention.

FIG. 63 is an illustration of a SIDE view of a section of wireframe 231 showing that, during an elongation phase of a compressive cycle, e.g. when the valve is in deployed in a heart and subjected to compressive forces, the suture attachment line 259 for mounting the leaflet 258 on the inner frame 231 can be tailored to work dynamically with leaflet structure to reduce damage to the prosthetic leaflets during valve delivery, according to the invention.

FIG. 64 is an illustration of a SIDE view of a section of compressed wireframe 239 showing that, during a compression phase of a compressive cycle, e.g. when the valve is in deployed in a heart and subjected to compressive forces, the suture attachment line 259 for mounting the leaflet 258 on the inner frame can be tailored to work dynamically with leaflet structure to reduce damage to the prosthetic leaflets during valve delivery, according to the invention.

FIG. 65 is an illustration of a TOP view of a leaflet free edge 261 bowing open during expansion, the edge 261 that is not mounted on the inner wire frame 231, according to the invention.

FIG. 66 is an illustration of a TOP view of a leaflet free edge 261 laying flat during compression, the edge that is not mounted on the compressed inner wire frame 239, according to the invention.

FIG. 67 is an illustration of a TOP view of a leaflet 258 showing that leaflet shape is optimized at multiple planes between the free edge 261 of the leaflet and the sewn 259, belly portion, and is based on the dynamic foreshortening of the inner wire frame, according to the invention.

FIG. 68 is an illustration of a TOP view of a flow control component 231, and shows that the location of the commissures 289 of the prosthetic leaflets 258 are adjustable to allow for optimized leaflet shape and commissure attachment, according to the invention. FIG. 68 also shows hinge 285 as a design element for successful folding the inner wire frame 231.

FIG. 69 is another illustration of a TOP view of a flow control component 231, and shows that the location of the commissures 289 of the prosthetic leaflets 258 are adjustable to allow for optimized leaflet shape and commissure attachment, according to the invention. FIG. 69 also shows hinge 285 as a design element for successful folding the inner wire frame 231.

FIG. 70 is an illustration of a SIDE view of a part of a flow control component 231, and shows that the location of the commissures 289 of the prosthetic leaflets 258 are adjustable to allow for optimized leaflet shape and commissure attachment, according to the invention.

FIG. 71 is another illustration of a SIDE view of a part of a flow control component 231, and shows that the location of the commissures 289 of the prosthetic leaflets 258 are adjustable to allow for optimized leaflet shape and commissure attachment, according to the invention.

FIG. 72 is an illustration of a SIDE view of a non-cylindrical embodiment of an inner frame 231 having a flared cuff-like portion 227 in the atrial-facing section to allow for better blood flow and smooth transition from the outer frame component 102 (not shown). Fold line 109 shows how the flared embodiment is designed to fold flat for size reduction necessary for trans-catheter delivery, according to the invention.

FIG. 73 is an illustration of a TOP view of a non-cylindrical embodiment of an inner frame 231 with leaflet cusps 258 mounted therein, according to the invention.

FIG. 74 is an illustration of a TOP view of a non-cylindrical embodiment of an inner frame 231 having an oval shape with the leaflet cusps 258 attached by additional support tabs or structures 287, and the non-leaflet areas of the interior aspect of the inner frame 231 filled or covered with mesh 143, according to the invention.

FIG. 75 is an illustration of a SIDE EXPLODED view of a valve having an oval outer frame 102, with a smaller oval inner frame 231, with tissue or polymer supports 264 attached to a smaller tissue leaflet component 258, which is blocked in on opposing sides with mesh spacers 143, according to the invention.

FIG. 76 is an illustration of a SIDE view of a human heart having a trans-septal (trans-femoral/IVC or SVC) delivery catheter 138 crossing from the right atrium to the left atrium for access to the mitral valve, according to the invention.

FIG. 77 is an illustration of a CROSS-SECTIONAL view of a human heart showing the relative locations of the mitral valve, the tricuspid valve, the aortic valve, and the pulmonary valve, according to the invention.

FIG. 78 is an illustration of a TOP view of a mitral valve and shows guide wire 434 directing the replacement valve 100 to the A1 leaflet with the valve 100 in a compressed intra-catheter configuration, according to the invention. Distal tab 268 is shown with guide wire 434 threaded through the end of the distal tab 268, to guide the distal tab 268 is over the guide wire 434, and lead the valve 100 into the correct deployment location.

FIG. 79 is an illustration of a TOP view of a mitral valve and prosthetic valve 100 with distal tab 268 attached to the outer frame 102 and guide wire 434 threaded through the end of the distal tab 268, such that when the guide wire 434 is pre-positioned into the A1 location, the distal tab 268 is fed over the guide wire 434 leading the valve 100 into the correct deployment location. The valve 100 is in a partial deployment stage being partially expelled from delivery catheter 138, according to the invention.

FIG. 80 is an illustration of a TOP PERSPECTIVE view of a prosthetic valve 100 having collar 103, outer frame 102, inner frame 231, and spacer component 137. Distal tab 268 is attached to the outer frame 102 and guide wire 434 is threaded through the end of the distal tab 268, such that when the guide wire 434 is pre-positioned into the A1 location, the distal tab 268 is fed over the guide wire 434 leading the valve 100 into the correct deployment location. FIG. 80 shows the valve 100 fully expelled from delivery catheter 138 and positioned temporarily at an upwards angle with a distal anchoring tab 268 in the A1 area, and a proximal A3 anchoring tab 270 above the mitral valve. This angled positioning avoids a pop-off effect and allows for the new prosthetic valve 100 to engage the blood flow while the native mitral valve continues to operate, just prior to the proximal side being shoe-horned into place with the A3 tab 270 anchoring the proximal side of the valve, for a non-traumatic transition from native valve to prosthetic valve 100, according to the invention.

FIG. 81 is an illustration of a TOP view of a prosthetic valve deployed in the native annulus (not visible—in dashed line), according to the invention.

FIG. 82 is an illustration of a SIDE PERSPECTIVE view of a prosthetic valve deployed in the native annulus (not visible), according to the invention.

FIG. 83 is an illustration of a SIDE PERSPECTIVE view of an embodiment of a prosthetic valve having an A2 clip 314 integrated into the sidewall 110 of the A2 facing side of the outer frame 102 of the valve, according to the invention.

FIG. 84(a)-(d) is an illustration of a TOP PERSPECTIVE view of a close-up view of a sequence showing an A2 clip 314 being actuated from (a) a stowed position against the sidewall 110 of the prosthetic valve outer frame 102, to (b) an open tab-capture position by extending the A2 clip positioning tool 316, to (c) an open tab-A2 leaflet in capture range-position, to (d) a closed position with the A2 leaflet captured between the clip 314 and the outer frame sidewall 110, according to the invention.

FIG. 85 is an illustration of a SIDE PERSPECTIVE view of an inner wire frame 231 and shows 3 cells per side in two rows for a total of six cells per side and twelve (12) cells 233 total as a preferred embodiment for mounting three (3) leaflet cusps.

FIG. 86 is an illustration of a SIDE PERSPECTIVE view of an inner wire frame 231 and shows 6 cells per side in two rows for a total of twelve cells per side and twenty-four (24) cells 233 total as a preferred embodiment for mounting three (3) leaflet cusps.

FIG. 87 is an illustration of a SIDE view of a detail of an inner wire frame 231 during diastole (leaflet opening) showing how leaflet tissue 258 is sutured and critical leaflet-frame attachment or connection points 289 are positioned during (lateral) cell expansion.

FIG. 88 is an illustration of a SIDE view of a detail of an inner wire frame 231 during systole (leaflet 258 closing) showing how leaflet tissue 258 is sutured and critical leaflet-frame attachment or connection points 289 are positioned during cell contraction, and how the cell geometry 233 reduces leaflet failure at known commissure failure points 289.

FIG. 89 is an illustration of a TOP view of valve leaflets 258 during diastole.

FIG. 90 is an illustration of a TOP view of valve leaflets 258 during systole.

FIG. 91 is an illustration of a SIDE view of a detail of inner wire frame 231 showing how a nitinol or other semi-rigid (semi-flexible) arch 264 can be mounted on the inner wire frame 231 to provide an additional surface for suturing the leaflet cusp 258 to the wire frame 231.

Additional Definitions and Parts List

Below is provided a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets.

100 A dual-tab side delivered transcatheter prosthetic heart valve.
102 a self-expanding annular (outer) support frame.
103 Collar structure.
104 Central channel.
106 Outer perimeter wall.
107 Top edge of outer support frame.
108 Central vertical axis.
109 Z-axis, front to back, fold line axis.
110 Front wall portion of perimeter wall.
112 Back wall portion of perimeter wall.
114 Proximal side.
116 Proximal fold area.
117 Secondary proximal fold areas.
118 Distal side.
120 Distal fold area.
121 secondary distal fold areas.
122 Front upper collar portion.
124 Front lower body portion of outer frame.
126 Back upper collar portion.
128 Back lower body portion.
129 Sewn attachment points for inner to outer.
130 Flow control component, made of an inner frame having tissue leaflets mounted therein, collapsible (foldable and compressible), the inner mounted within the annular outer support frame and configured to permit blood flow in a first direction through an inflow end and block blood flow in the opposite, second direction, through the outflow end.
132 Inflow end.
134 Outflow end.
135 Second spacer component.
136 a compressed configuration
137 (First) inner spacer component.
138 Delivery catheter.
139 Uncovered spacer, engineered (therapy) partial regurg
140 X-axis, a horizontal axis, parallel to delivery. catheter central axis
141 Spacer cover, mesh.
142 Intersecting angle 45-135 degrees, X-axis to Y-axis.
143 Inner frame cover, top cover, mesh.
144 Expanded configuration.
146 Length-wise cylindrical axis of delivery catheter.
148 Height of about 5-60 mm.
150 Diameter of about 25-80 mm.
202 Plurality of compressible wire cells—outer frame.
204 Orientation and cell geometry substantially orthogonal, perpendicular, to the central vertical axis to minimize wire cell strain when the annular support frame is compressed.
206 Vertical compressed configuration.
208 Folded configuration.
210 Folded and compressed configuration.
212 Inner frame or outer frame shape selected from a funnel, cylinder, flat cone, or circular hyperboloid.
220 Braided matrix.
222 Wire frame matrix.
224 Laser-cut wire frame.
226 Biocompatible material.
227 Flared cuff on INNER frame.
228 Side profile of inner frame as a flat cone shape.
229 Non-cylindrical inner frame, e.g. elliptical section.
230 Diameter R of 40-80 mm.
231 INNER frame, for mounting leaflets.
232 Diameter r of 20-60 mm.
233 Set of uniform wire frame cells of INNER.
234 Height of 5-60 mm.
235 Non-uniform variable height cells of INNER.
236 Interior surface of annular outer support frame.

237 Non-uniform cell geometries, sizes in wire frame.
238 Exterior surface of annular outer support frame.
239. Compressed INNER.
240 Pericardial tissue for covering valve surfaces.
241 Diamond or eye-shaped wire cells.
242 Woven synthetic polyester material.
243 Eyelets on inner wire frame, consistent commissure attachment.
244 Outer support frame with an hourglass shape.
245 Laser cut attachment feature on inner frame.
246 Top diameter R1 of 40-80 mm.
248 Bottom diameter R2 of 50-70 mm.
250 Internal diameter r of 20-60 mm.
252 Height of 5-60 mm.
254 Internal diameter of 20-60 mm.
256 Height of 10-40 mm.
257 Leaflet band, mounting band for leaflet pockets.
258 LEAFLETS, plurality of leaflets, pericardial material.
259 Sewn edge of leaflet.
260 Rounded cylinder at an inflow end.
261 Open edge of leaflet
262 Flat closable aperture at an outflow end.
264 Longitudinal supports in/on flow control component, selected from rigid or semi-rigid posts, rigid or semi-rigid ribs, rigid or semi-rigid battens, rigid or semi-rigid panels, and combinations.
266 (any) Tab or tension arm extending from a distal side of the annular support frame.
268 DISTAL SUB-ANNULAR ANCHORING TAB, can be RVOT or other, comprised of wire loop or wire frame, integrated frame section, or stent, extending from about 10-40 mm away from the annular support frame.
269 Independent RVOT tab.
270 PROXIMAL SUB-ANNULAR ANCHORING TAB.
271 Independent proximal tab.
272 Distal upper edge of the annular support frame.
273 Upper atrial tension arm, comprised of wire loop or wire frame extending from about 2-20 mm away from the annular support frame.
274 Lower tension arm comprised of wire loop or wire frame, integrated frame section, or stent, extending from about 10-40 mm away from the annular support frame.
276 Distal side of the annular support frame.
278 Tissue anchors connected to the annular support frame for engaging native tissue.
280 Front wall portion of frame is a first flat panel.
282 Back wall portion of frame is a second flat panel.
284 Sewn seam.
285 Hinge.
286 Flexible fabric span without any wire cells.
287 Fabric panel.
288 Braided-wire cells.
289 Commissure attachment—leaflet to frame.
290 Laser-cut wire cells.
302 a compressed configuration.
304 Bilaterally rolled compressed configuration.
306 Flattened annular support frame into parallel panels
308 Compressed annular support frame along a vertical axis
310 Rigid elongated pushing rod/draw wire
311 Guide wire.
312 Steerable catheter for rotating the prosthesis
314 A2 Clip for attachment to mitral A2 leaflet
316 A2 Clip Deployment Tool
434 Guide wire Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. An inner flow control component for a side delivered heart valve, comprising:
a leaflet frame with 2-4 flexible leaflets mounted thereon, the leaflet frame comprising two or more panels of diamond-shaped or eye-shaped wire cells made from heat-set Nitinol and configured to be foldable along a z-axis from a rounded or cylindrical configuration to a flattened cylinder configuration, and compressible along a vertical y axis to a shortened configuration,
wherein the 2-4 flexible leaflets are configured to permit blood flow in a first direction through an inflow end of the inner flow control component and block blood flow in a second direction, opposite the first direction, through an outflow end of the inner flow control component.

2. The inner flow control component of claim 1, wherein the inner flow control component has a diameter R of 20-30 mm, and a height of 5-20 mm.

3. The inner flow control component of claim 1, wherein the inner flow control component is mounted in a side delivered transcatheter prosthetic heart valve, the valve comprising:
(i) a self-expanding annular (outer) support frame, the annular support frame having a central channel and an outer perimeter wall circumscribing a central vertical axis in an expanded configuration, the annular support frame having a distal side and a proximal side,
(ii) the inner flow control component mounted within the annular support frame and configured to permit blood flow in the first direction through an inflow end of the valve and block blood flow in the second direction, opposite the first direction, through an outflow end of the valve,
(iii) a distal anchoring tab mounted on the distal side of the annular support frame, and
(iv) a proximal anchoring tab mounted on the proximal side of the annular support frame,
wherein the valve is compressible to a compressed configuration for introduction into the body using a delivery catheter for implanting at a desired location in the body, the compressed configuration is oriented along a horizontal x-axis at an intersecting angle of between 45-135 degrees to the central vertical y-axis, and expandable to an expanded configuration having a horizontal x-axis at an intersecting angle of between 45-135 degrees to the central vertical y-axis, wherein the horizontal x-axis of the compressed configuration of the valve is substantially parallel to a lengthwise cylindrical axis of the delivery catheter,
wherein the valve has a height of about 5-60 mm and a diameter of about 25-80 mm.

4. The valve of claim 3, wherein the annular support frame is comprised of a plurality of compressible wire cells having an orientation and cell geometry substantially orthogonal to the central vertical y-axis to minimize wire cell strain when the annular support frame is configured in a vertical compressed configuration, a rolled compressed configuration, or a folded compressed configuration.

5. The valve of claim 3, wherein the annular support frame has a lower body portion and an upper collar portion, wherein the lower body portion in an expanded configuration forms a shape selected from a funnel, cylinder, flat cone, or circular hyperboloid.

6. The valve of claim 3, wherein the annular support frame is comprised of a braided, wire, or laser-cut wire frame, and the annular support frame is covered with a biocompatible material.

7. The valve of claim 3, wherein the annular support frame has a diameter R of 40-80 mm, a diameter r of 20-60 mm, and a height of 5-60 mm.

8. The valve of claim 3, wherein the annular support frame has an inner surface and an outer surface, the inner surface and the outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

9. The valve of claim 3, wherein the valve in an expanded configuration has a central vertical y-axis that is substantially parallel to the first direction.

10. The valve of claim 3, wherein the inner flow control component is supported with one or more longitudinal supports integrated into or mounted upon the inner flow control component, the one or more longitudinal supports selected from rigid or semi-rigid posts, rigid or semi-rigid ribs, rigid or semi-rigid battens, rigid or semi-rigid panels, and combinations thereof.

11. The valve of claim 3, wherein the distal anchoring tab is comprised of a wire loop, a wire frame, a laser-cut frame, an integrated frame section, or a stent, and the distal anchoring tab extends from about 10-40 mm away from the distal side of the annular support frame.

12. The valve of claim 3, wherein the proximal anchoring tab is comprised of a wire loop, a wire frame, a laser-cut frame, an integrated frame section, or a stent, and the proximal anchoring tab extends from about 10-40 mm away from the proximal side of the annular support frame.

13. The valve of claim 3, wherein the distal anchoring tab is a lower distal anchoring tab, the valve further comprising:
an upper distal anchoring tab attached to a distal upper edge of the annular support frame, the upper distal anchoring tab comprised of a wire loop, a wire frame, a laser-cut frame, an integrated frame section, or a stent, and the upper distal anchoring tab extends from about 2-20 mm away from the distal upper edge of the annular support frame.

14. The valve of claim 3, further comprising:
at least one tissue anchor connected to the annular support frame for engaging native tissue.

15. The valve of claim 3, wherein the annular support frame is comprised of compressible wire cells selected from the group consisting of braided-wire cells, laser-cut wire cells, photolithography produced wire cells, 3D printed wire cells, wire cells formed from intermittently connected single strand wires in a wave shape, a zig-zag shape, or spiral shape, and combinations thereof.

* * * * *